(12) United States Patent
Mazed et al.

(10) Patent No.: US 10,540,704 B2
(45) Date of Patent: Jan. 21, 2020

(54) SYSTEM AND METHOD FOR MACHINE LEARNING BASED USER APPLICATION

(71) Applicants: Mohammad A. Mazed, Chino Hills, CA (US); Sayeeda Mazed, Yorba Linda, CA (US)

(72) Inventors: Mohammad A. Mazed, Chino Hills, CA (US); Sayeeda Mazed, Yorba Linda, CA (US)

(*) Notice: Subject to any disclaimer, the term of this patent is extended or adjusted under 35 U.S.C. 154(b) by 472 days.

(21) Appl. No.: 15/530,996

(22) Filed: Apr. 5, 2017

(65) Prior Publication Data
US 2017/0221032 A1     Aug. 3, 2017

Related U.S. Application Data

(63) Continuation-in-part of application No. 14/999,601, filed on Jun. 1, 2016, now Pat. No. 9,923,124, which
(Continued)

(51) Int. Cl.
| | |
|---|---|
| *G06Q 30/06* | (2012.01) |
| *G06Q 20/20* | (2012.01) |
| *G06N 3/08* | (2006.01) |
| *G06Q 20/32* | (2012.01) |
| *G06Q 20/12* | (2012.01) |

(Continued)

(52) U.S. Cl.
CPC ........... *G06Q 30/0631* (2013.01); *G06N 3/08* (2013.01); *G06N 10/00* (2019.01); *G06N 20/00* (2019.01); *G06Q 20/12* (2013.01); *G06Q 20/20* (2013.01); *G06Q 20/3278* (2013.01);
(Continued)

(58) Field of Classification Search
CPC .... G06Q 20/12; G06Q 20/20; G06Q 20/3278; G06Q 30/02; G06Q 30/0222; G06Q 30/0251; G06Q 30/026; G06Q 30/06; G06Q 30/0631; G06Q 30/0633; G06Q 30/0639;
(Continued)

(56) References Cited

U.S. PATENT DOCUMENTS

| | | | | |
|---|---|---|---|---|
| 7,370,276 B2 * | 5/2008 | Willis | ................. | G06F 16/9535 715/747 |
| 2002/0147645 A1 * | 10/2002 | Alao | ................. | G06Q 30/0209 705/14.54 |

(Continued)

OTHER PUBLICATIONS

Leppaniemi, et al., Mobile Marketing: From Marketing Strategy to Mobile Marketing Campaign Implementation, Journal of Mobile Marketing (Year: 2008).*

*Primary Examiner* — Charles Guiliano

(57) ABSTRACT

The invention synthesizes a social network, electronic commerce (including performance based advertisement and electronic payment), a mobile internet device and a machine learning algorithm(s), utilizing a classical computer or a quantum computer enhanced machine learning algorithm(s), utilizing a quantum computer. The synthesized social commerce further dynamically integrates stored information, real time information and real time information/data/image(s) from an object/array of objects (Internet of Things (IoT)). The machine learning algorithm(s), utilizing a classical computer can include a software agent, a fuzzy logic algorithm, a predictive algorithm, an intelligence rendering algorithm and a self-learning (including relearning) algorithm.

24 Claims, 49 Drawing Sheets

Related U.S. Application Data is a continuation-in-part of application No. 13/448,378, filed on Apr. 16, 2012, now Pat. No. 9,697,556, which is a continuation-in-part of application No. 12/931,384, filed on Jan. 31, 2011, now Pat. No. 8,548,334, which is a continuation-in-part of application No. 12/238,286, filed on Sep. 25, 2008, now abandoned, and a continuation-in-part of application No. 11/952,001, filed on Dec. 6, 2007, now Pat. No. 8,073,331.

(60) Provisional application No. 62/230,249, filed on Jun. 1, 2015, provisional application No. 61/517,204, filed on Apr. 15, 2011, provisional application No. 61/404,504, filed on Oct. 5, 2010, provisional application No. 60/970,487, filed on Sep. 6, 2007.

(51) Int. Cl.
*G06Q 30/02* (2012.01)
*G06Q 50/00* (2012.01)
*G06N 10/00* (2019.01)
*G06N 20/00* (2019.01)

(52) U.S. Cl.
CPC .............. *G06Q 30/02* (2013.01); *G06Q 30/06* (2013.01); *G06Q 30/0639* (2013.01); *G06Q 50/01* (2013.01)

(58) Field of Classification Search
CPC ........ G06Q 50/01; G06N 10/00; G06N 20/00; G06N 3/08
USPC ..... 705/14.23, 14.66, 26.8, 14.49, 26.7, 26.9
See application file for complete search history.

(56) References Cited

U.S. PATENT DOCUMENTS

| | | | |
|---|---|---|---|
| 2003/0126146 A1* | 7/2003 | Van Der Riet | G06Q 30/02 |
| 2004/0003096 A1* | 1/2004 | Willis | G06F 16/9535 709/228 |
| 2004/0103024 A1* | 5/2004 | Patel | G06Q 30/02 705/14.53 |
| 2007/0053513 A1* | 3/2007 | Hoffberg | G06K 9/00369 380/201 |
| 2007/0162337 A1* | 7/2007 | Hawkins | G06Q 30/02 705/14.27 |
| 2008/0307034 A1* | 12/2008 | Fleet | G06Q 30/0603 709/202 |
| 2012/0179516 A1* | 7/2012 | Fakhrai | G06Q 30/0207 705/14.1 |
| 2012/0265596 A1* | 10/2012 | Mazed | G06Q 30/02 705/14.23 |
| 2013/0024360 A1* | 1/2013 | Ballout | G06Q 20/04 705/39 |

* cited by examiner

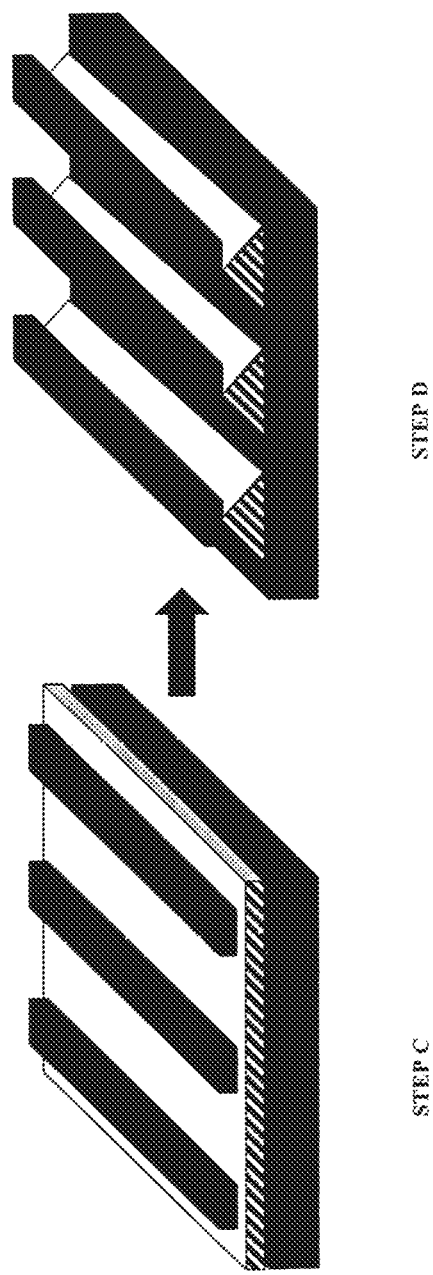

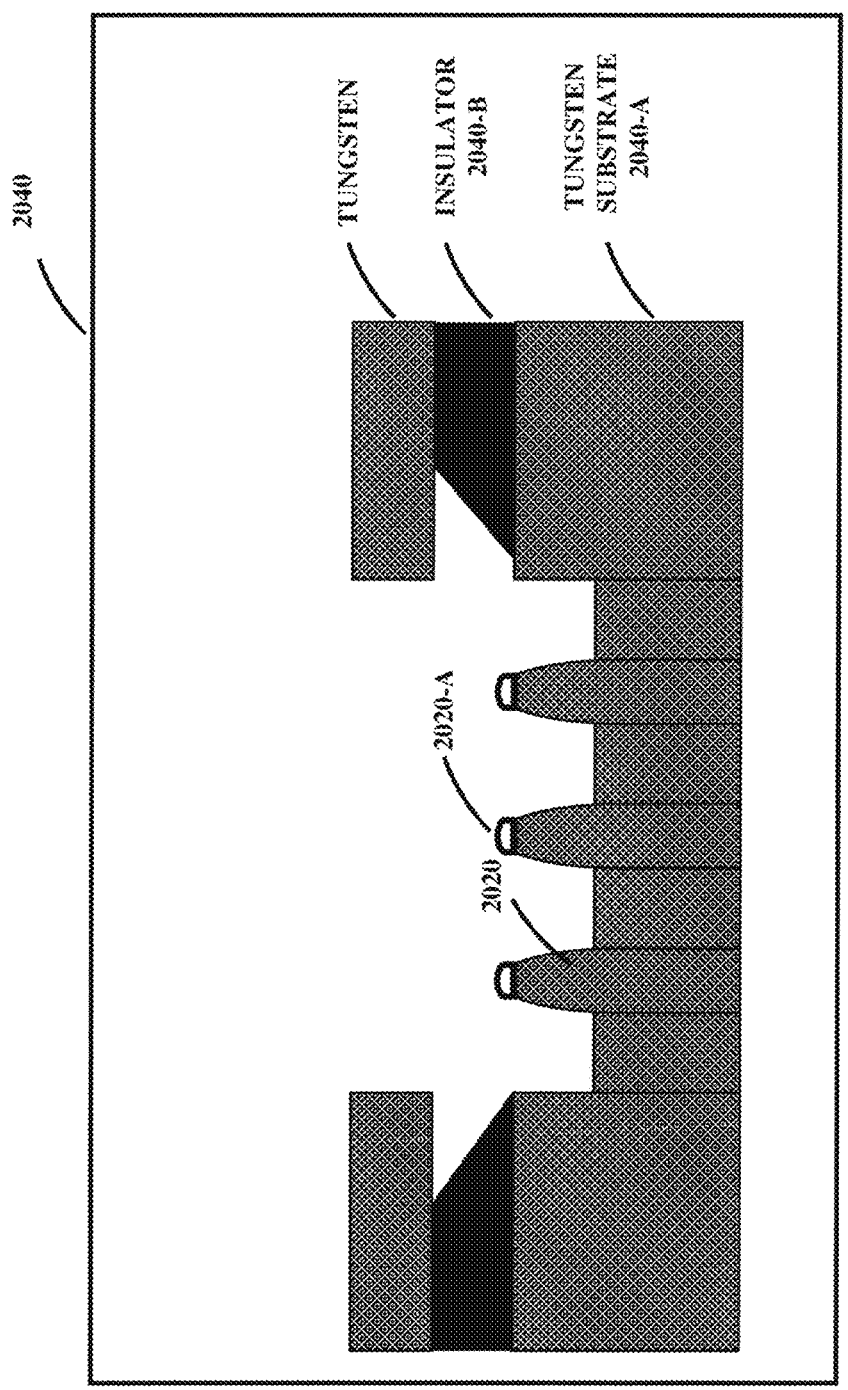

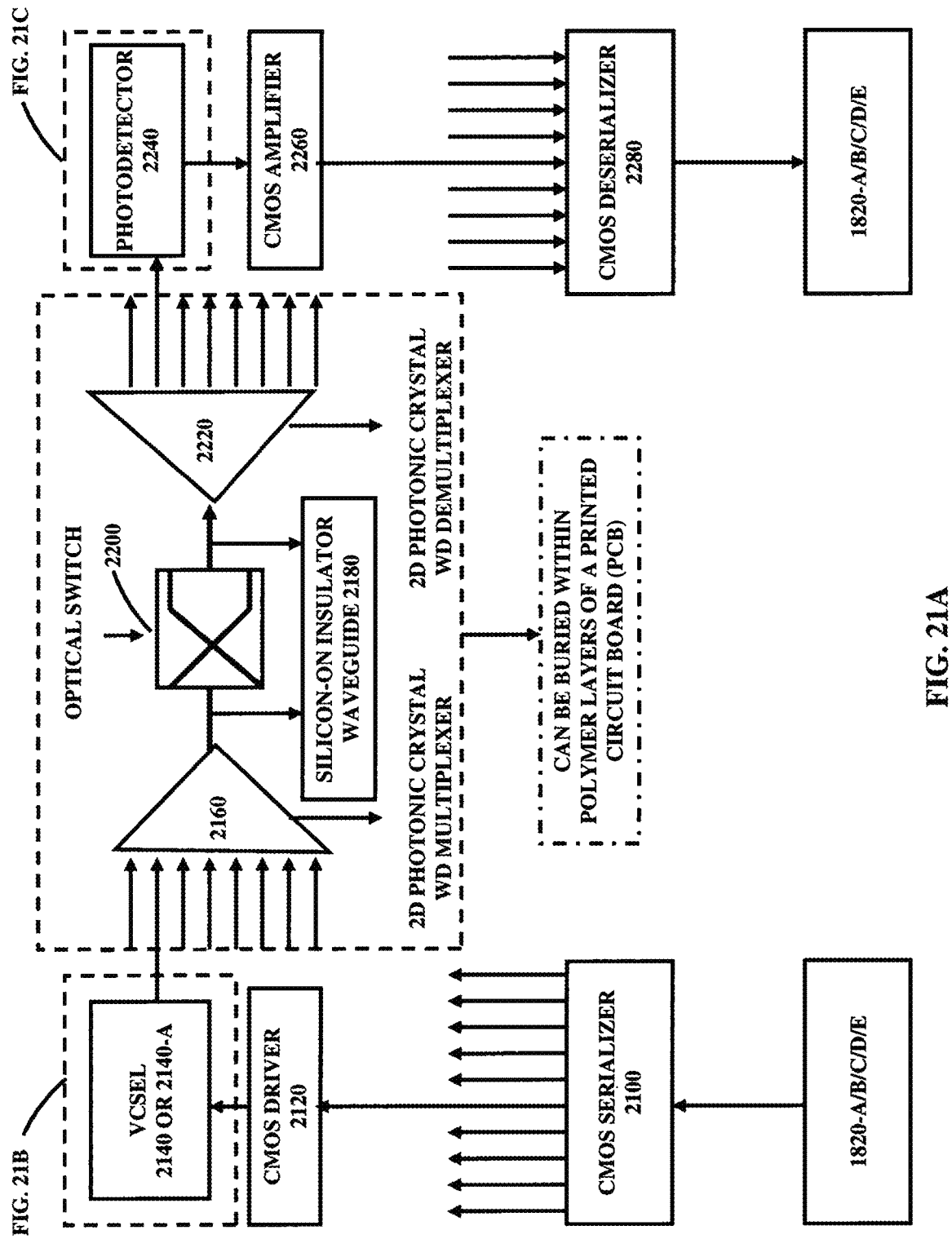

SYSTEM AND METHOD FOR MACHINE LEARNING BASED USER APPLICATION

CROSS REFERENCE OF RELATED APPLICATIONS

The present application is a continuation-in-part (CIP) of (a) U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 (which claims benefit of priority to: U.S. Provisional Patent Application No. 62/230,249 entitled "SYSTEM AND METHOD OF AMBIENT/PERVASIVE USER/HEALTHCARE EXPERIENCE", filed on Jun. 1, 2015).
(b) U.S. Non-Provisional patent application Ser. No. 13/448,378 entitled "SYSTEM AND METHOD FOR MACHINE LEARNING BASED USER APPLICATION", filed on Apr. 16, 2012 (which claims benefit of priority to U.S. Provisional Patent Application No. 61/517,204 entitled "INTELLIGENT SOCIAL E-COMMERCE" filed on Apr. 15, 2011).
(c) U.S. non-provisional patent application Ser. No. 12/931,384 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Jan. 31, 2011 (now U.S. Pat. No. 8,548,334, issued on Oct. 1, 2013), which claims the benefit of priority to U.S. provisional application Ser. No. 61/404,504 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Oct. 5, 2010, which (c) is a continuation-in-part (CIP) of
(d) U.S. non-provisional patent application Ser. No. 12/238,286 entitled "PORTABLE INTERNET APPLIANCE", filed on Sep. 25, 2008, and
(e) U.S. non-provisional patent application Ser. No. 11/952,001, entitled "DYNAMIC INTELLIGENT BIDIRECTIONAL OPTICAL AND WIRELESS ACCESS COMMUNICATION SYSTEM" filed on Dec. 6, 2007 (now U.S. Pat. No. 8,073,331, issued on Dec. 6, 2011), which claims the benefit of priority to
  (i) U.S. provisional patent application Ser. No. 60/970,487 entitled "INTELLIGENT INTERNET DEVICE", filed on Sep. 6, 2007,
  (ii) U.S. provisional patent application Ser. No. 60/883,727 entitled "WAVELENGTH SHIFTED DYNAMIC BIDIRECTIONAL SYSTEM", filed on Jan. 5, 2007,
  (iii) U.S. provisional patent application Ser. No 60/868,838 entitled "WAVELENGTH SHIFTED DYNAMIC BIDIRECTIONAL SYSTEM", filed on Dec. 6, 2006.

The entire contents of all Non-Provisional Patent Applications and Provisional Patent Applications as listed in the previous paragraph and the filed Application Data Sheet (ADS) are hereby incorporated by reference.

FIELD OF THE INVENTION

The present invention generally relates to the integration of a social network, electronic commerce (including performance based advertisement and electronic payment) and a mobile internet device (MID).

Furthermore, synthesized social electronic commerce dynamically integrates stored information, information (preferably real time information), communication with an object/array of objects (where the object can be coupled with a wireless (or radio) transmitter and/or a sensor)—Internet of Things (IoT) and a unified algorithm.

The unified algorithm can include a software agent, a fuzzy logic algorithm, a predictive algorithm, an intelligence rendering algorithm and a self-learning (including relearning) algorithm. It should be noted that real time information is near real time information in practice.

BACKGROUND OF THE INVENTION

Social networking is no longer just about making social connections online. User experience can be enhanced not only by connecting with people, but also by connecting with information (preferably real time information) and communicating with the object/array of objects.

The cornerstone of today's electronic commerce is based on converting a probable click (in a search engine) into an actual sale.

By synthesizing social networking with the electronic commerce, one can deliver consistent user experience across all touch-points (e.g., social, mobile and in-store).

Furthermore, synthesized social electronic commerce can also integrate stored information, real time information, data from the mobile internet device and real time information/data/image(s) from the object/array of objects, where the object can be coupled with a wireless (or radio) transmitter and/or a sensor.

However, the mobile internet device can preferably communicate with a node, which can further communicate with the object/array of objects for spatial and time averaged information/data/image(s) from the object/array of objects.

The integration of social networking with (real time) user location information from a user's mobile internet device and information/data/image(s) from the object/array of objects can embed physical reality into an internet space and an internet reality into a physical space.

Furthermore, the unified algorithm (integrating a software agent, a fuzzy logic algorithm, a predictive algorithm, an intelligence rendering algorithm and a self-learning (including relearning) algorithm can add a new dimension to user experience.

Furthermore, by designing a system-on-chip (SoC) (an advanced microprocessor integrated with a security algorithm) for the mobile internet device, intelligence can also be rendered to the mobile internet device.

SUMMARY OF THE INVENTION

The invention synthesizes the social network, electronic commerce (including the performance based advertisement and electronic payment) and mobile internet device (intelligence is achieved utilizing advanced algorithm(s) and/or advanced microprocessor design(s) for the mobile internet device).

The synthesized social electronic commerce further dynamically integrates stored information, real time information, information/data/image(s) from the object/array of objects (where the object can be coupled with a wireless (or radio) transmitter and/or a sensor) and the unified algorithm (which includes a software agent, a fuzzy logic algorithm, a predictive algorithm, an intelligence rendering algorithm and a self-learning (including relearning) algorithm).

DETAILED DESCRIPTION OF THE INVENTION

Figure 1A:
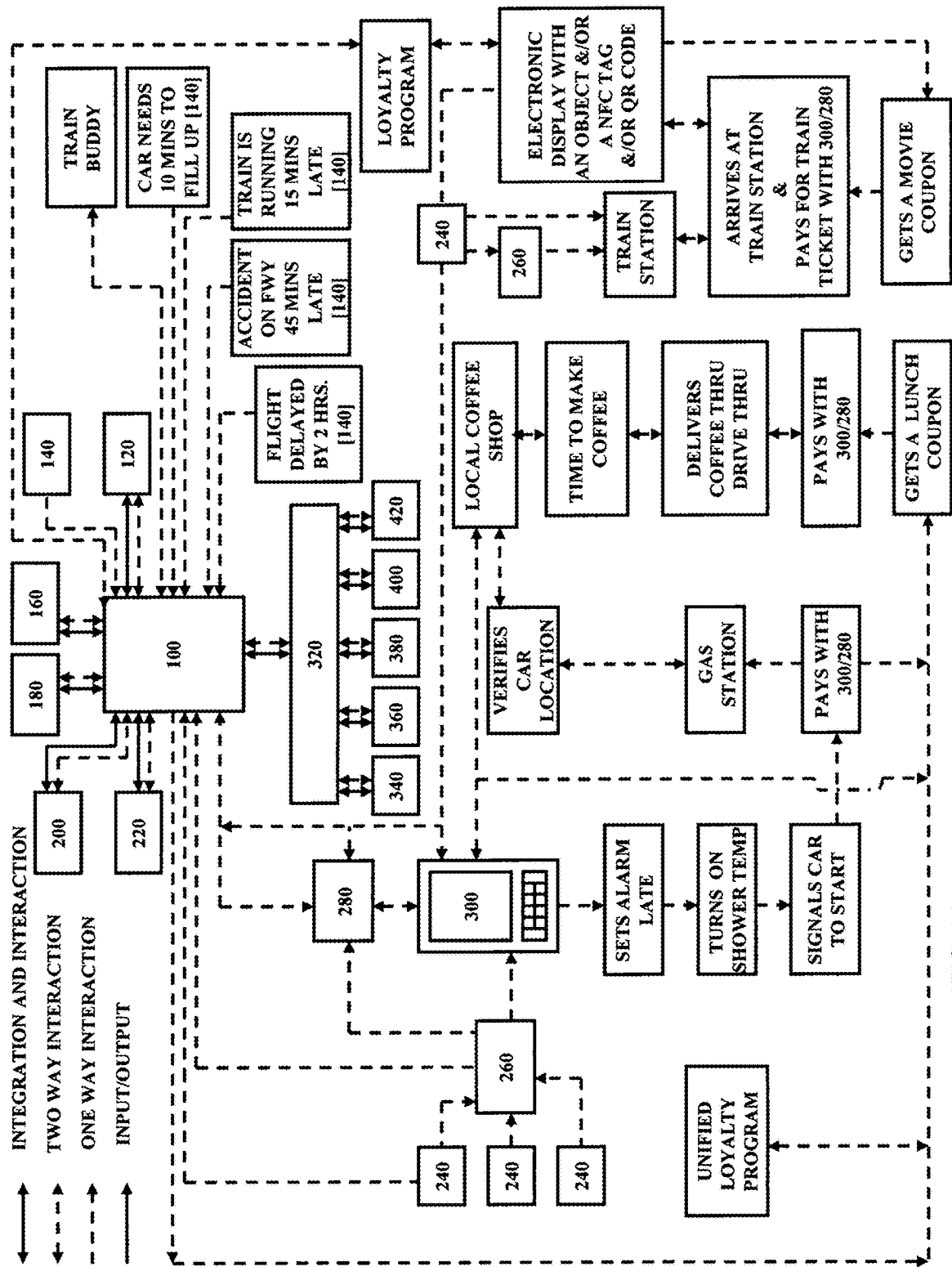
FIGS. 1 (A and B) illustrates an integrated application flow chart of a social wallet, according to one embodiment of the present invention.

FIG. 1A illustrates an integrated application flow chart of a social wallet 100. The social wallet 100 can be a social networking web portal and it can typically reside at a cloud based secure server, which can be coupled or integrated with a learning (including relearning) classical/quantum computer. The learning (including relearning) classical computer integrates one or more microprocessors, or one or more neural network based microprocessors, executing computer readable instructions and machine learning algorithm(s), stored on a non-transitory computer readable medium of the cloud based secure server to implement the social wallet 100. The social wallet 100 can connect/access stored information from a data storage (preferably a cloud based secure data storage) component(s) 120, can connect/access with information (preferably real time information) from an information source(s) (preferably real time information) 140, can connect with a user(s) 160, can connect with a merchant(s) 180, can connect with a deposit account(s) 200, can connect with a payment account(s) 220, can connect with an object/array of objects 240s, can connect with a node(s) 260, can connect with a social wallet electronic module(s) 280, can connect with a mobile internet appliance(s) 300. Furthermore, the social wallet 100 can connect/access with a unified algorithm 320 and connect with the user 160 via an automated agent/bot (e.g., a chat bot/search bot), enhanced by the unified algorithm 320. The user 160 could type/talk with the social wallet 100 via the mobile internet appliance 300: "Hi, should I renegotiate my car lease?" Instead of a search result, a lease bot enhanced by the unified algorithm 320 would pop up suggesting a better deal and close it for the user 160 in exchange for a small commission.

It should be noted that the mobile internet appliance 300 can be a mobile wearable device, but the mobile wearable device is generally in a smaller form factor with respect to the mobile internet appliance 300. Details of the mobile wearable device have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 (which claims benefit of priority to: U.S. Provisional Patent Application No. 62/230,249 entitled "SYSTEM AND METHOD OF AMBIENT/PERVASIVE USER/HEALTHCARE EXPERIENCE", filed on Jun. 1, 2015).

The unified algorithm 320 can consist of a software agent 340, a fuzzy logic algorithm 360, a predictive algorithm 380, an intelligence rendering algorithm 400 and a self-learning (including relearning) algorithm 420. It should be noted that the self-learning (including relearning) algorithm 420 can include a self-learning artificial intelligence algorithm and/or a self-learning neural network algorithm and/or a quantum computer enhanced machine learning algorithm.

At the heart of a quantum computer is a quantum bit (qubit)—a basic unit of information analogous to a classical bit 0/1 represented by a transistor in a classical computer. The qubit is exponentially more powerful than the classical bit 0/1, because of its two unique properties: it can represent both 1 and 0 at the same time. But for qubit to be useful, it must achieve both quantum superposition (like being in two physical states simultaneously) and quantum entanglement (like what happens to one qubit can instantly affect the other qubit, even when they are physically separated) and these two unique properties can be easily upset by a slightest disturbance (e.g., a material defect/vibration/fluctuating electric fields/noise). Therefore, qubits are extremely susceptible to error, without operating at an extremely low temperature. A quantum computer enhanced machine learning algorithm is an approach that enables a quantum computer to learn/re-learn and to make predictions-by combining machine learning with quantum computation. A quantum computer enhanced machine learning algorithm can be compiled on one or more microprocessors, or one or more neural network based microprocessors and downloaded onto the quantum computer-classical computer interface for execution. An application of the quantum computer enhanced machine learning algorithm can be hyper personalized advertising.

An example-application of the social wallet 100, can allow the user 160 to get (a) his/her favorite coffee, as he/she approaches a Starbucks without placing an order, or (b) the object/array of objects 240s can notify the user 160 that his/her train is running late, or (c) the object/array of objects 240s can turn on room temperature, as the user 160 approaches his/her home, or (d) the user 160 can get a relevant coupon(s), when the user 160 is engaging with an electronic display, where the electronic display is embedded with the object/array of objects 240s and/or near-field communication (NFC) tags and/or one-dimensional (1-D)/two-dimensional (2-D) quick response (QR) codes (e.g., a smart poster).

Furthermore, the social wallet 100 can connect with a location measurement component of the mobile internet appliance(s) 300.

The social wallet 100 can act as an ultimate integrator (e.g., a Trusted Service Manager (TSM)) of many needs of the user 160, connecting with other users 160s for various information and needs, transferring information between the other users 160s, securely transferring money to the deposit account 200 (e.g., a bank), securely transferring money to the payment account 220 (e.g., a bill payment account) and securely transferring money (e.g., a microloan) between the other users 160s.

The social wallet 100 can integrate a blockchain, instead of the Trusted Service Manager. A blockchain is a global distributed ledger/database running on millions of devices and open to anyone, where not just information, but anything of value. In essence it is a shared, trusted public ledger that everyone can inspect, but which no single user controls. A blockchain creates a distributed document of (outputs/transactions) in the form of a digital ledger, which can be available on a network of computers/mobile internet devices 300s. When a transaction happens, the users 160s propose a record to the ledger. Records are bundled into blocks (groups for processing) and each block receives a unique fingerprint derived from the records it contains. Each block includes the fingerprint of the prior block, creating a robust and unbreakable chain. It's easy to verify the integrity of the entire chain and nearly impossible to falsify historic records. In summary, a blockchain is a public ledger of transactions, which critically provides trust, based upon mathematics rather than human relationships/institutions. A blockchain can replace the historically designed Trusted Service Manager.

Additionally, a blockchain can be integrated with the object/array of objects 240s and/or near-field communication tags and/or one-dimensional/two-dimensional quick response codes and such integration with a blockchain can build trust, reduce cost and accelerate smart (automated) transaction.

Figure 1B:
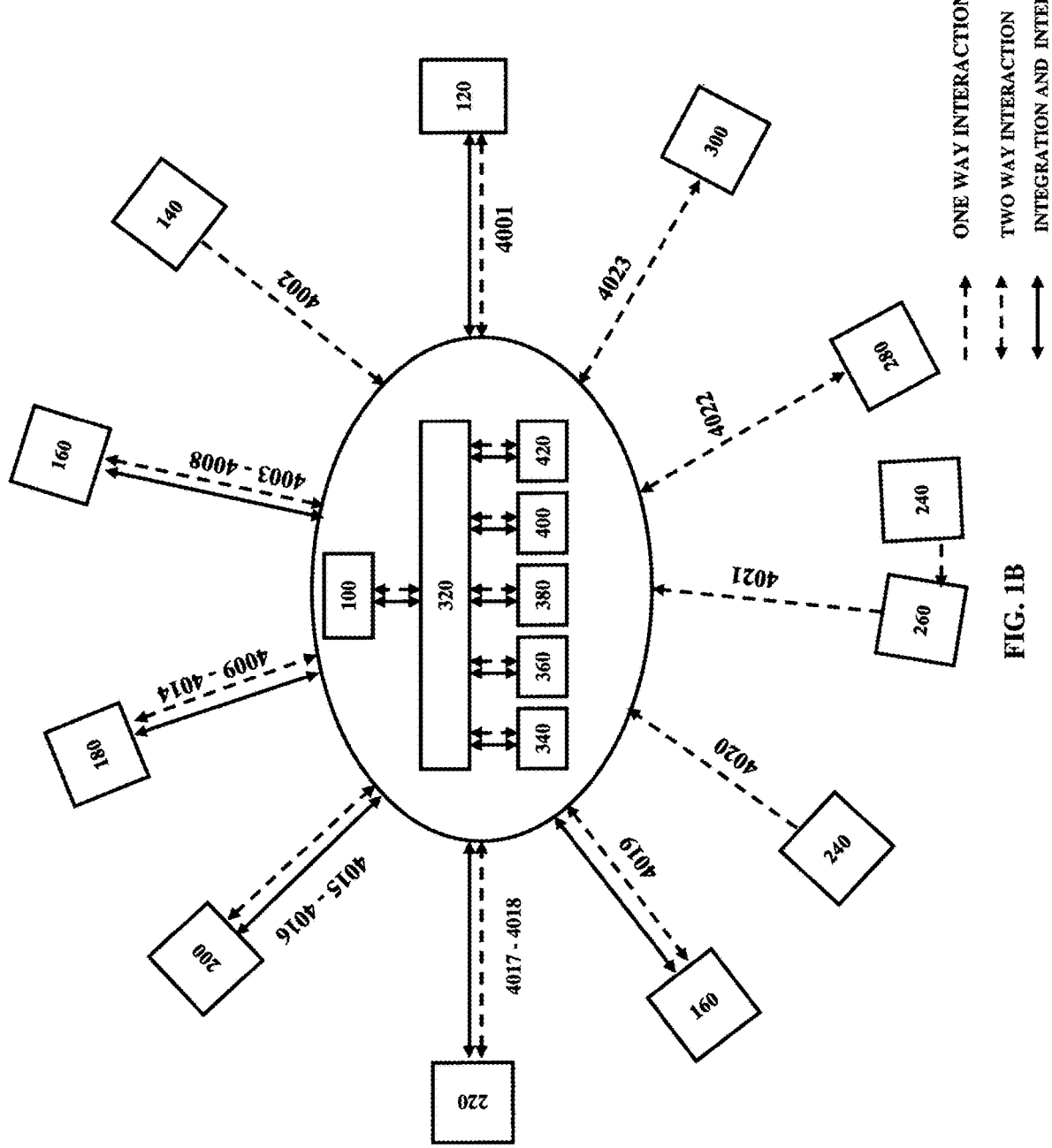

FIG. 1B illustrates steps from 4001 to 4025. In step 4001, the social wallet 100 can connect/access stored information from the data storage (preferably the cloud based secure data storage) component(s) 120. In step 4002, the social wallet 100 can connect/access to the information source (preferably real time information) 140.

In step 4003, the social wallet 100 can connect to the user 160 via a profile. In step 4004, the social wallet 100 can connect to the user 160 via online/offline message. In step 4005, the social wallet 100 can connect to the user 160 via chat message. In step 4006, the social wallet 100 can connect to the user 160 via broadcast message. In step 4007, the social wallet 100 can connect to the user 160 via like/dislike vote. In step 4008, the social wallet 100 can connect to the other users 160s for a collaborative purchase of a product and/or service.

In step 4009, the social wallet 100 can connect to the merchant 180 via profile. In step 4010, the social wallet 100 can connect to the merchant 180 via online/offline message. In step 4011, the social wallet 100 can connect to the merchant 180 via chat message. In step 4012, the social wallet 100 can connect to the merchant 180 via broadcast message. In step 4013, the social wallet 100 can connect to the merchant 180 via bid. In step 4014, the social wallet 100 can connect to the merchant 180 via bid in real time. Furthermore, the bid/bid in real time can be based on game theory/evolutionary game theory. An example of the user 160 and N merchants 180s is described here. Using descending price [second price] for the product or service, the price starts high and continues to fall until one merchant 180 is left. Using ascending price [first price] for the product and/or service, the price starts low and continues to increase until one merchant 180 accepts. The user 160 can also suggest a price for the product and/or service to N merchants 180s in a time period and buy from the merchant 180, who accepts the user 160's bid. The number of bidding rounds is determined by how frequently the user 160 can make an offer.

In step 4015, the user 160 can deposit money (electronic scan of a money order and/or a check) and/or legally approved electronic cash (e.g., Bitcoins, digital gold currency and webmoney with traceable serial numbers) to the deposit account 200 via the social wallet 100. In step 4016, the user 160 can withdraw money from the deposit account 200 via the social wallet 100.

In step 4017, the user 160 can pay money to the payment account 220 via the social wallet 100. In step 4018, the user 160 can transfer/consolidate many payment accounts to the payment account 220 via the social wallet 100.

In step 4019, the user 160 can transfer money (e.g., a microloan) to the other users 160s via the social wallet 100. In step 4020, the social wallet 100 can communicate with the object 240.

Furthermore, the objects 240s, near-field communication tags and/or one-dimensional/two-dimensional quick response codes can be embedded on an electronic display Such communication with the objects 240s and/or near-field communication tags and/or one-dimensional/two-dimensional quick response codes can generate loyalty points in real time and can create personalized customer loyalty program, when they are connected with the social wallet 100.

In step 4021, the social wallet 100 can communicate with the node 260. Furthermore, the node 260 can communicate with the object/array of objects 240s.

In step 4022, the social wallet 100 can communicate with the social wallet electronic module 280.

In step 4023, the social wallet 100 can communicate with the mobile internet device 300.

In step 4024, the social wallet 100 can communicate with the unified algorithm 320. The unified algorithm 320 can consist of a software agent 340, a fuzzy logic algorithm 360, a predictive algorithm 380, an intelligence rendering algorithm 400 and a self-learning (including relearning) algorithm 420. In step 4025, a software agent 340, a fuzzy logic algorithm 360, a predictive algorithm 380, an intelligence rendering algorithm 400 and a self-learning (including relearning) algorithm 420 can communicate or couple with the said algorithms.

The intelligent rendering algorithm 400 can include algorithms such as: artificial intelligence, data interpretation, data mining, machine vision, natural language processing, neural network, pattern recognition and reasoning modeling.

Additionally, a neural network can approximate a function, but it is impossible to interpret the result in terms of a natural language. But an integration of the neural network and fuzzy logic in a neuro-fuzzy algorithm can provide both learning and readability. The neuro-fuzzy algorithm can use a fuzzy inference engine (with fuzzy rules) for modeling uncertainties, which is further enhanced through learning the various situations with a radial basis function. The radial basis function consists of an input layer, a hidden layer and an output layer with an activation function of hidden units. A normalized radial basis function with unequal widths and equal heights can be written as:

$$\psi_i(x)(softmax) = \frac{\exp(h_i)}{\sum_{i=1}^{n} \exp(h_i)}$$

$$h_i = \left(-\sum_{l=1}^{2} \frac{(X_l - u_{il})^2}{2\sigma_l^2}\right)$$

X is the input vector, uil is the center of the ith hidden node (i=1, . . . , 12) that is associated with the lth (l=1, 2) input vector, σi is a common width of the ith hidden node in the layer and softmax (hi) is the output vector of the ith hidden node. The radial basis activation function is the softmax activation function. First, the input data is used to determine the centers and the widths of the basis functions for each hidden node. Second, is a procedure to find the output layer weights that minimize a quadratic error between predicted values and target values. Mean square error can be defined as:

$$MSE = \frac{1}{N} \sum_{k=1}^{N} ((TE)_k^{exp} - (TE)_k^{cal})^2$$

FIGS. 2 (A, B, C, D, E, F and G) illustrates a method flow chart of integration of the social wallet (the social networking web portal) 100 and electronic commerce in the following steps:

In step 4026, the user 160 can log into the social wallet 100. In step 4027, the user 160 can set a privacy control in the social wallet 100. In step 4028, the user 160 can input his/her profile (e.g., gender, age group, income range, zip code, family members/friends' contacts) in the social wallet 100.

In step 4029, the unified algorithm 320 in the social wallet 100 can estimate the personal score of the user 160 by analyzing the profile, message history, chat history and data patterns (including purchase patterns). In step 4030, the unified algorithm 320 in the social wallet 100 can set the personal score of the user 160. The personal score of the user 160 can vary with time. In step 4031, the social wallet 100 can record the personal score of the user 160 over time.

In step 4032, the user 160 can authenticate in the social wallet 100, utilizing multi-level passwords and personalized questions. In step 4033, the user 160 can authenticate in the social wallet 100, by placing the social wallet electronic module 280, at a proximity to the near-field communication terminal (e.g., the near-field communication terminal of a computer/point-of-sale terminal) or by placing the mobile internet device 300, at a proximity to the near-field communication terminal (e.g., the near-field communication terminal of a computer/point-of-sale terminal), where the mobile internet device 300 also integrates the social wallet electronic module 280. It should be noted that by placing the social wallet electronic module 280 at a proximity to the near-field communication terminal of a computer, the social wallet 100/social wallet electronic module 280/user 160's profile/user 160 can be securely authenticated. Details of such secure authentication have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 (which claims benefit of priority to: U.S. Provisional Patent Application No. 62/230,249 entitled "SYSTEM AND METHOD OF AMBIENT/PERVASIVE USER/HEALTHCARE EXPERIENCE", filed on Jun. 1, 2015), In step 4034, the user 160 can also link the information about the product and/or service in the social wallet 100.

Alternatively, in step 4035, the user 160 can write a wanted ad for the product and/or service in the social wallet 100.

In step 4036, the unified algorithm 320 in the social wallet 100 can determine the location of the user 160 in real time by communicating with a location measurement component/miniature electronic module 1440 of the mobile internet device 300 of the user 160.

In step 4037, the unified algorithm 320 (in particular the software agent 340) in the social wallet 100 can send out queries to the location specific merchants 180s for the product and/or service, wanted by the user 160. If no offers from the location specific merchants 180s are found, then in step 4038, the unified algorithm 320 can send out queries to the location specific merchants in an increment of some distance (e.g., 20 Km) from the current location of the user 160 in order to secure the product and/or service, wanted by the user 160.

In step 4039, the unified algorithm in the social wallet 100 can forward the offers (e.g., in the form of a text/e-mail link/picture mail/video mail) from the merchants 180s into the mobile internet device 300 of the user 160, in real time (preferably via the user 160's profile in the social wallet 100).

In step 4040, the user 160 can optionally share the offers from the merchants 180s with the mobile internet devices 300s of the other users 160s, who are connected with the profile of the user 160, in real time (preferably via the other users 160s' profiles in the social wallet 100).

In step 4041, the other users 160s' connected with the profile of the user 160 vote for like/dislike vote (like quorum sensing). In step 4042, the user 160 can connect with the other users 160s for the collaborative purchase. In step 4043, the unified algorithm 320 in the social wallet 100 can input the result of the like/dislike vote, in real time. In step 4044, the unified algorithm 320 in the social wallet 100 can estimate a merchant score of the merchant 180 by analyzing many like/dislike votes.

Like or dislike votes can be computed by an algebraic equation (e.g., Fraction Likes=Number Like Votes/(Number Like Votes+Number Dislikes Votes). For example, if the Fraction Likes is below 0.2, then the merchant score is one star, if Fraction Likes is at least 0.2 but less than 0.4, then the merchant score is two stars and so on, if Fraction Likes is more than 0.8, then the merchant score is five stars.

Alternatively, the merchant score can be determined by (a) a statistical method (e.g., like/dislike vote distribution within segments of the users 160s) or (b) a quorum sensing clustering (QSC) algorithm or (c) a quorum sensing molecule (QSM) algorithm.

Quorum sensing is a biological process, by which a community of bacteria interacts and coordinates with neighboring bacteria locally with no awareness of global information. In quorum sensing, bacteria do not communicate with each other directly, yet they influence and sense from a local environment, which assures local decision making optimization simultaneously. As an example of quorum based decision making, assuming the number of users 160s is N in number and the user 160 has one of the two options (like (X) or dislike (Y)) with a constant probability r per time step. Probability r is independent of any actions taken by other users 160s. If the user 160 makes an option X, without the other users 160s, then the probability is $aP_x$ for option X and similarly, $aP_y$ for option Y. But, if the user 160 makes an option, wherein the other users 160s are present, then the probability is denoted as $P_x[a+(m-a)*\{x^k/(T^k+x^k)\}]$, wherein "a" and "m" are minimum and maximum probability respectively for making an option. T is the quorum threshold at which the above probability is halfway between "a" and "m". "k" determines the steepness of $P_x[a+(m-a)*\{x^k/(T^k+x^k)\}]$. If k is equal to 1, then the user 160 making an option is proportional to the number of the users 160s who made that option. If k is greater than 1, then $P_x[a+(m-a)*\{x^k/(T^k+x^k)\}]$ can act as a step-like switch at the threshold T.

Quorum sensing enables a clustering algorithm. The quorum sensing clustering algorithm can define a cluster as a local region, where density is high and continually distributed. Thus, the quorum sensing clustering algorithm is capable of clustering datasets that are not linearly separable. By mimicking quorum sensing, the quorum sensing clustering algorithm can be decentralized, so that it is suitable for high speed parallel and distributed computing. Quorum sensing can enable a self-learning algorithm (inspired by a dynamic biological process), which, can be immune to noise and outliers.

The quorum sensing molecule algorithm is at least based on non-linear dynamics observed at a population scale of a $node_i$, calculating quorum sensing level/information sharing at the $node_i$ and then making use of the $node_i$'s quorum sensing level/information to calculate/influence the level/information at neighboring nodes such as, $node_j \ldots node_k$.

The merchant score of the merchant 180 can vary over time. In step 4045, the social wallet 100 can record the merchant score. In step 4046, the social wallet 100 can display the merchant score of the merchant 180.

Furthermore, in step 4047, if the estimated personal score of the user 160 exceeds a certain pre-determined value set by the social wallet 100, then in step 4048, the unified algorithm 320 (in particular the fuzzy logic algorithm 360) in the social wallet 100 can determine other relevant products and/or services for the user 160. In step 4049, the social wallet 100 can send a coupon(s) (e.g., in the form of a text/e-mail link/picture mail/video mail) for the other relevant products and/or services from the merchants 180s to the mobile internet device 300 of the user 160, in real time. In step 4050, the user 160 can share the coupon(s) with the other users 160s by simply forwarding the coupon(s) to the other users 160s' mobile internet devices 300s, in real time (preferably via the other users 160s+ profiles in the social wallet 100.

In step 4051, the user 160 can pay for the product and/or service via the social wallet 100, or by the social wallet electronic module 280, or by the mobile internet device 300.

Furthermore, in step 4052, the unified algorithm 320 (in particular the predictive algorithm 380) in the social wallet 100 can initially determine a set of relevant users for a targeted advertisement for a specified product and/or service.

In step 4053, the unified algorithm 320 in the social wallet 100 can send a coupon(s) (e.g., in the form of a text/e-mail link/picture mail/video mail) related to the specified product and/or service from the merchants 180s to the profiles of the above set of relevant users 160s.

In step 4054, the above set of relevant users can share the coupon(s) (e.g., in the form of a text/e-mail link/picture mail/video mail) related to the specified product and/or service from the merchants 180s with the other users 160s' mobile internet devices 300s, in real time (preferably via the other users 160s' profiles in the social wallet 100).

If a targeted advertisement campaign does not receive a response greater than at a pre-determined % (e.g., 10%), then in step 4055, the unified algorithm 320 (in particular the predictive algorithm 380, the intelligence rendering algorithm 400 and the self-learning (including relearning) algorithm 420) in the social wallet 100 can iterate (fine-tune) to find another set of relevant users for the targeted advertisement, until the targeted advertisement would be concluded successful to stop, when the targeted advertisement campaign receives the response greater than at the pre-determined % (e.g., 10%).

Figure 2A:
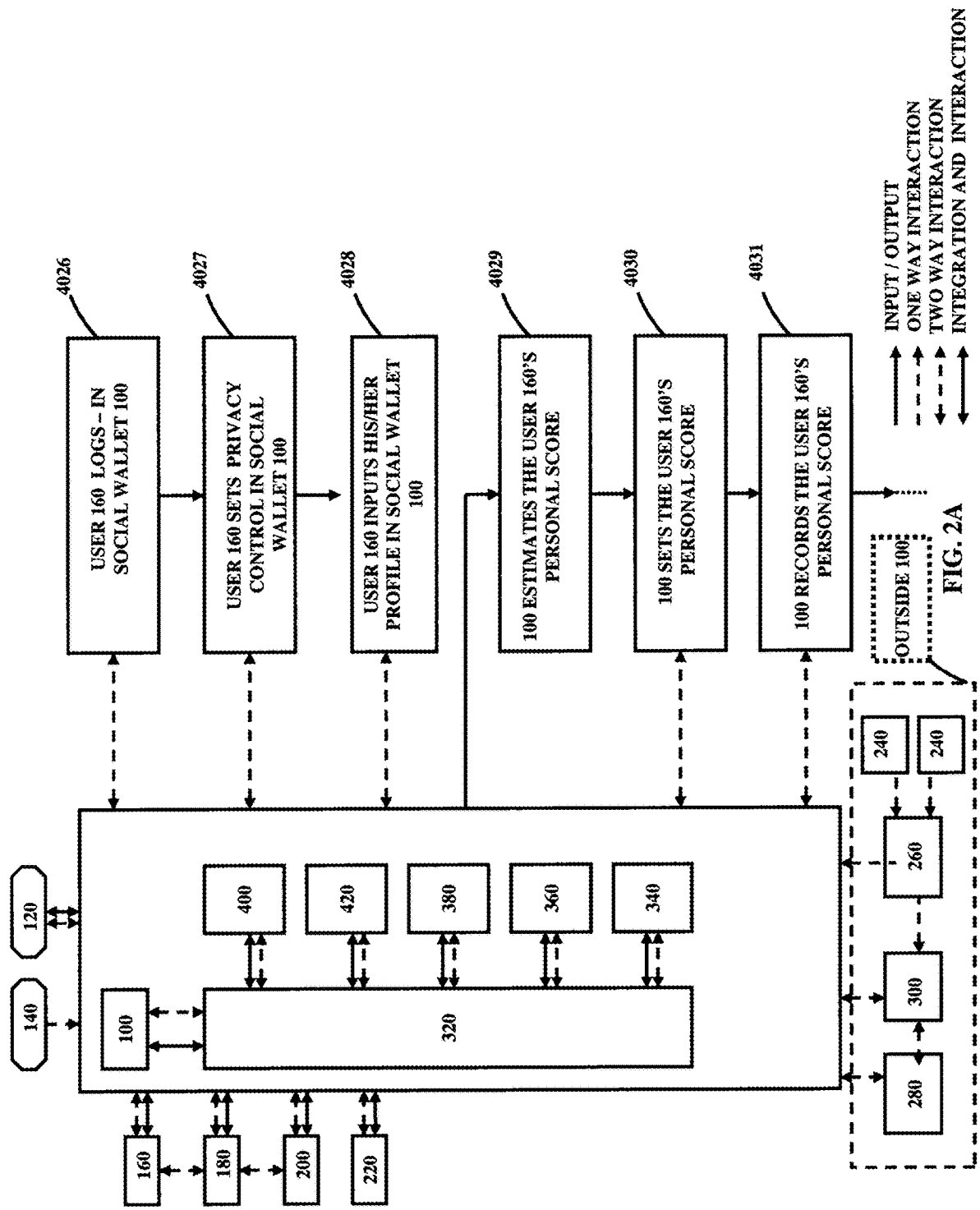
FIGS. 2 (A, B, C, D, E, F, G and H) illustrates a method flow chart of integration of the social wallet, electronic commerce and performance based advertisement, according to one embodiment of the present invention.
Figure 2B:
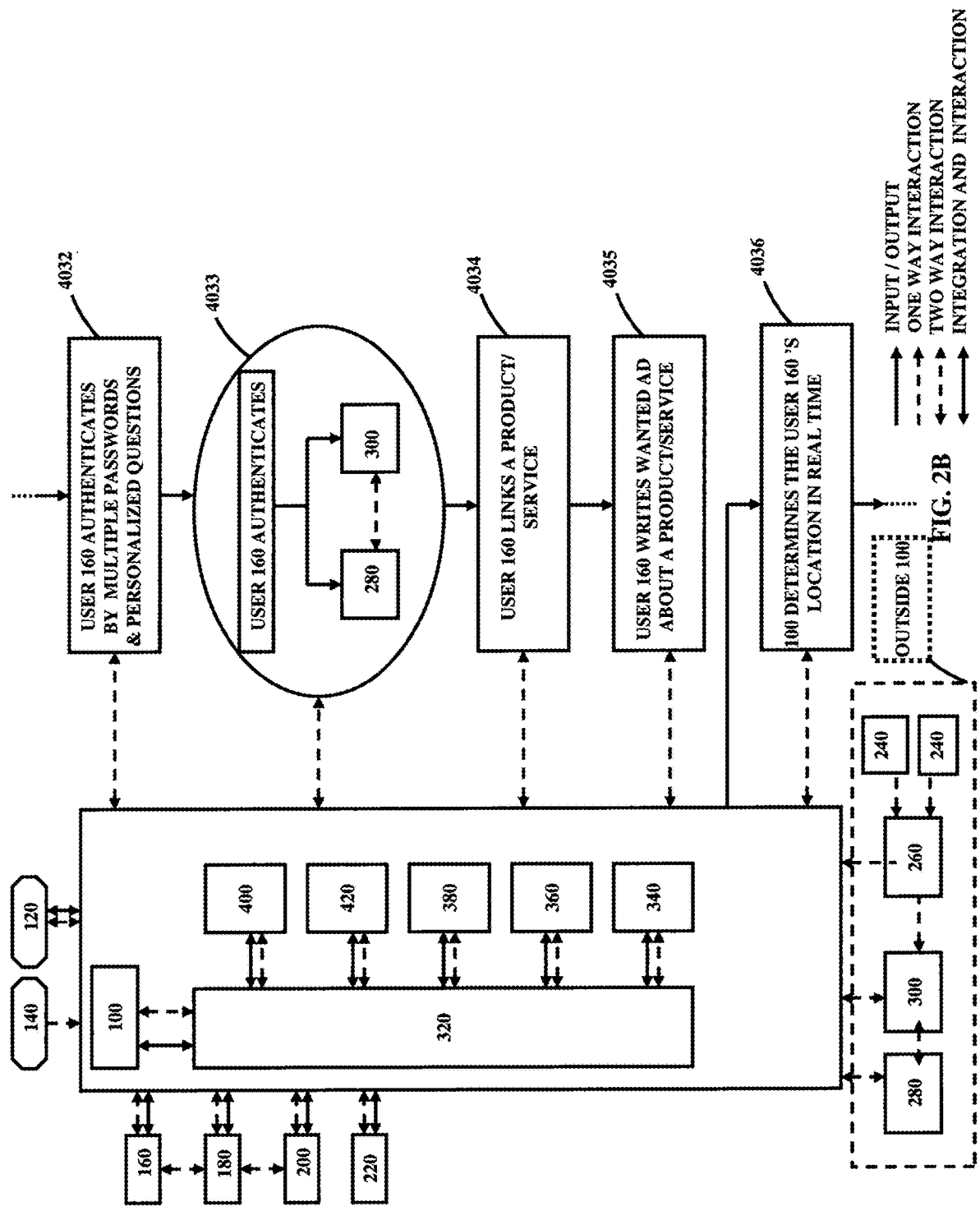
Figure 2C:
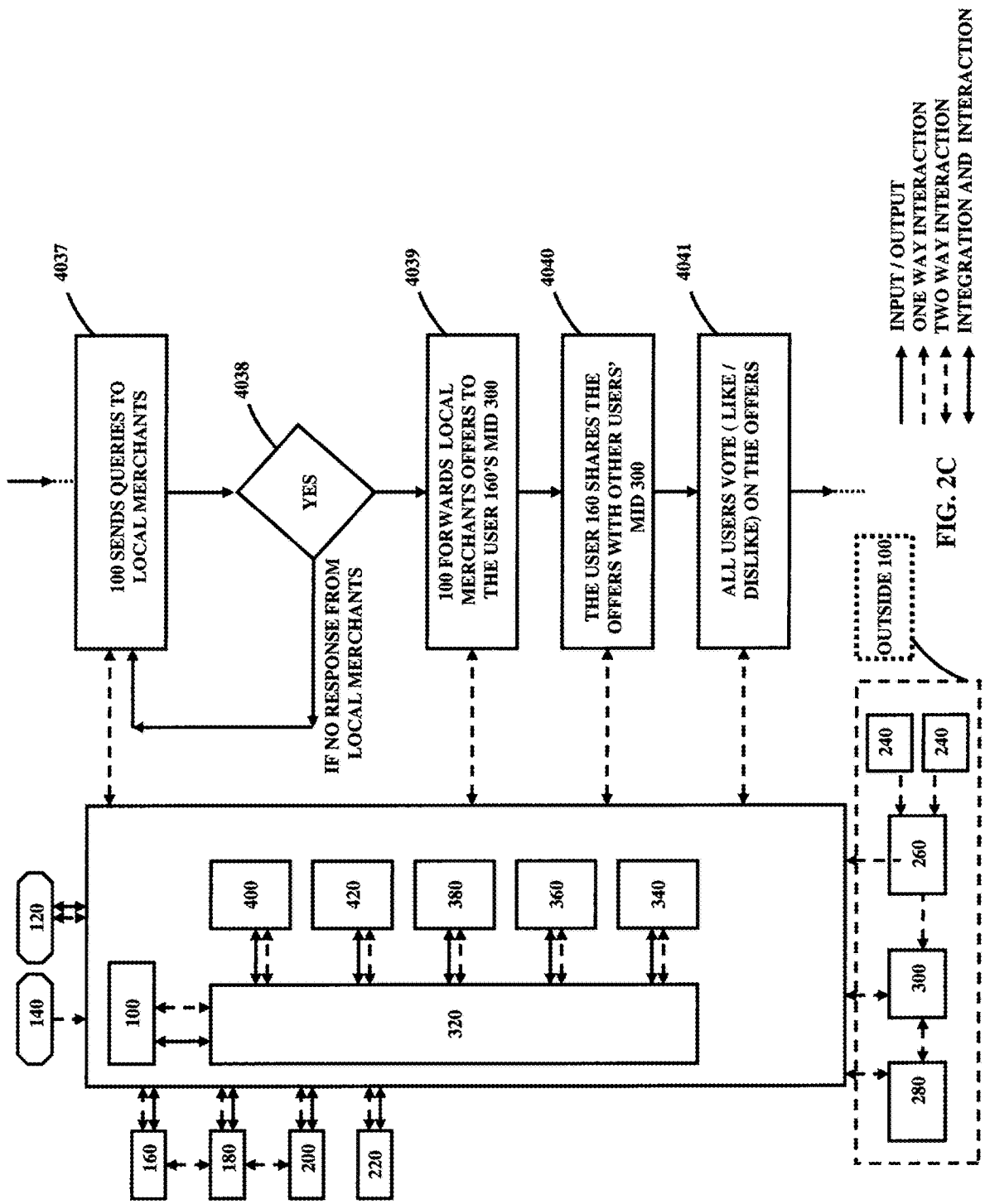
Figure 2D:
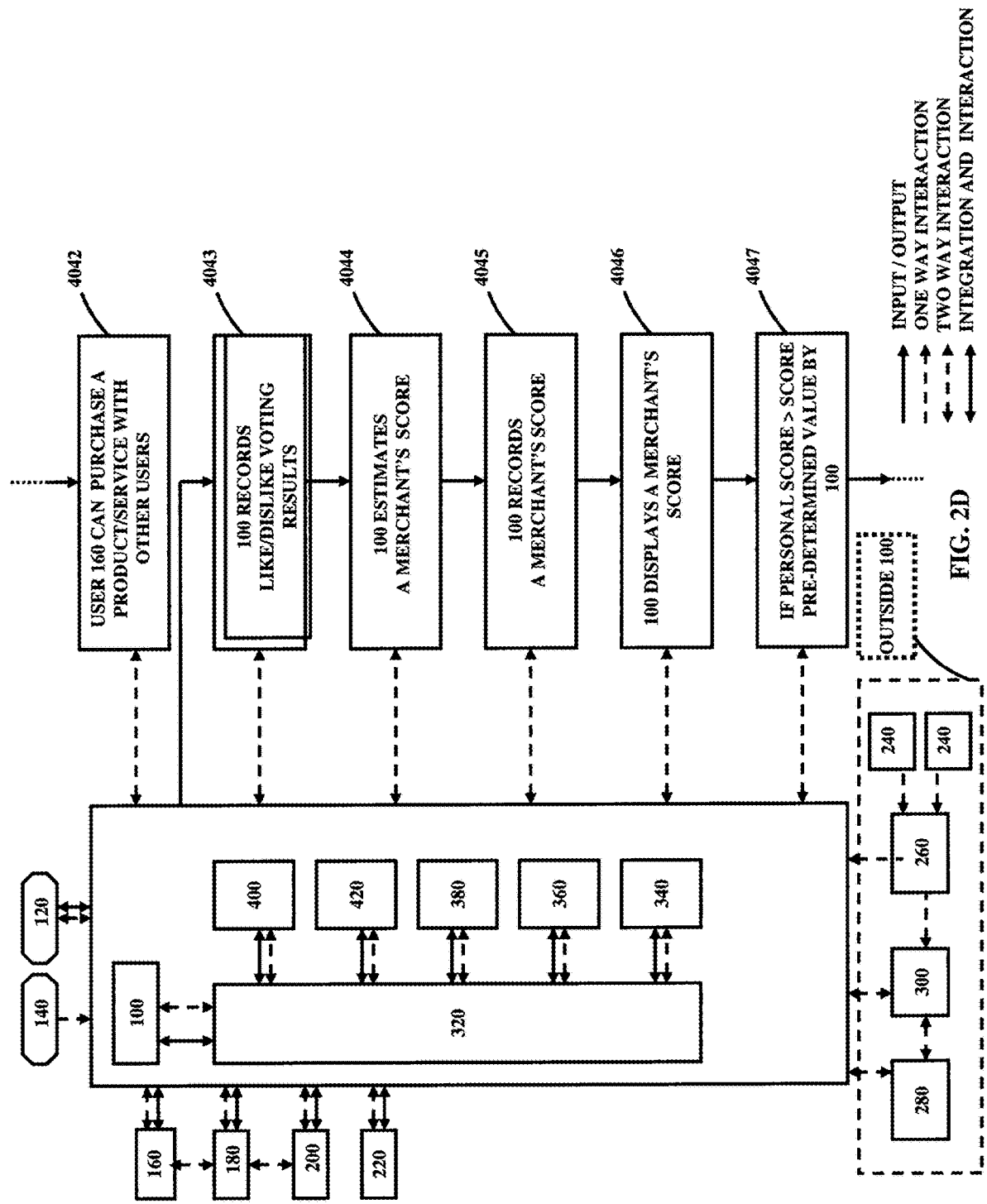
Figure 2E:
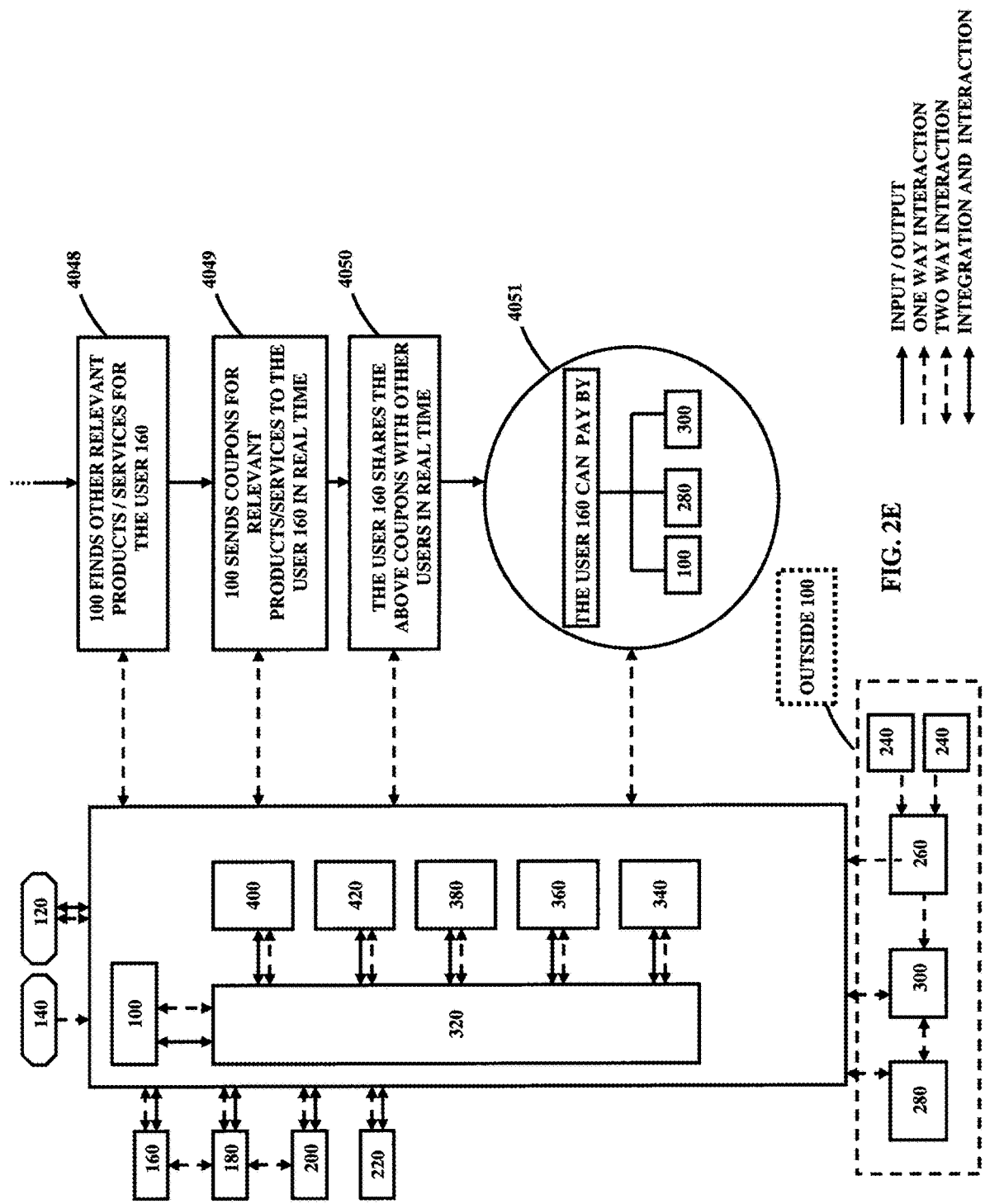
Figure 2F:
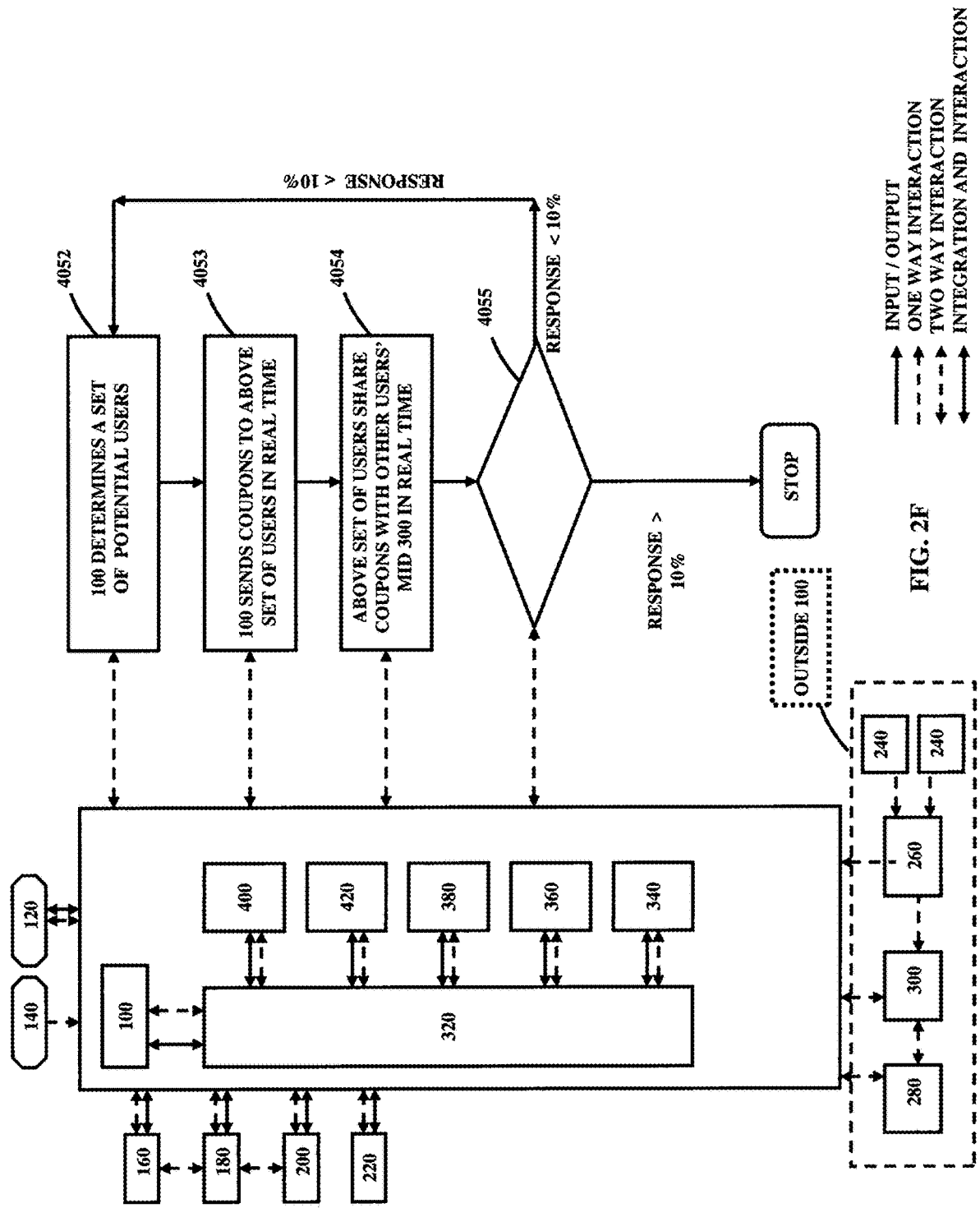
Figure 2G:
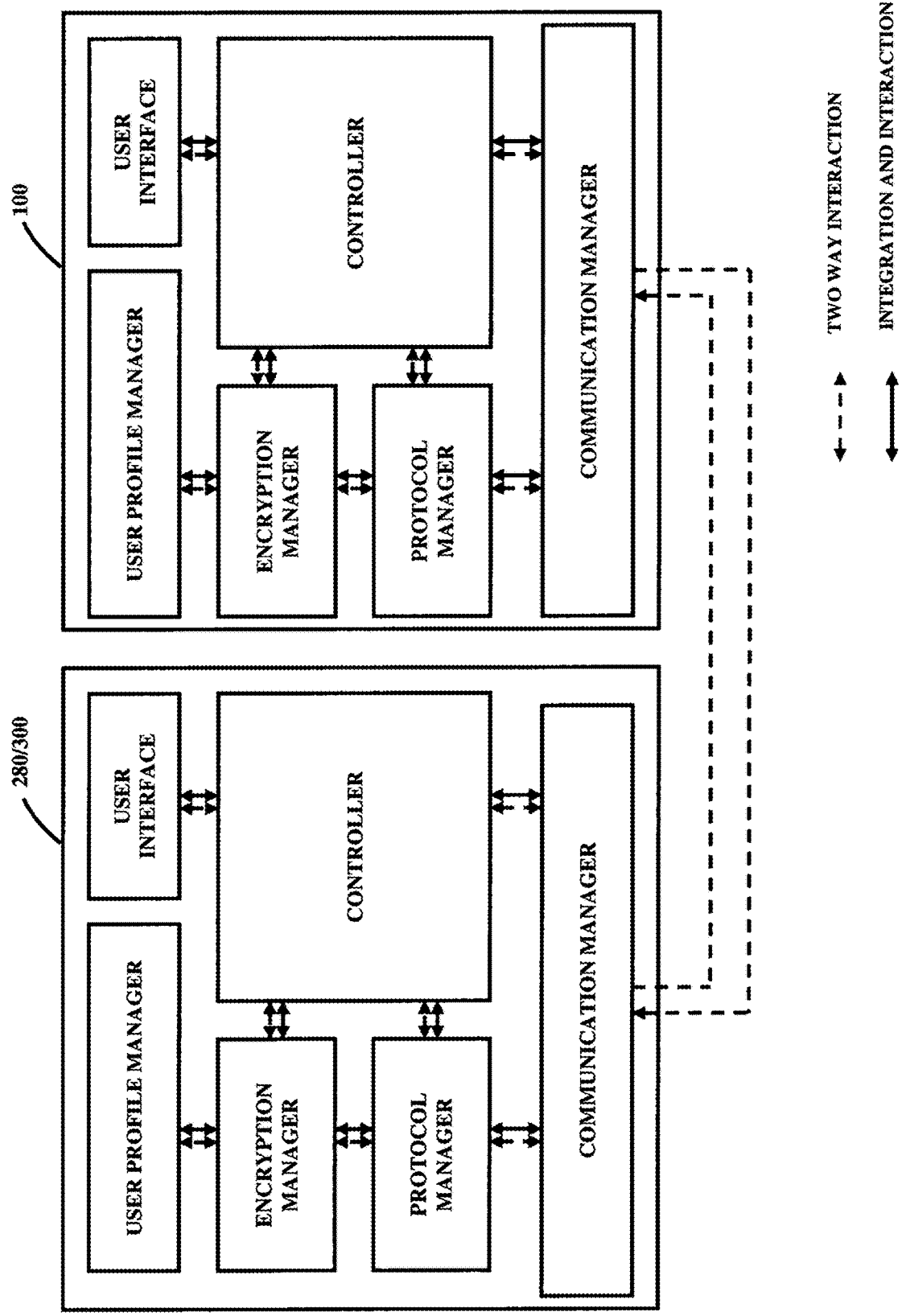

FIG. 2G illustrates how the social wallet electronic module 280 and/or mobile internet device 300 can communicate symmetrically with the social wallet 100 utilizing a controller, a user interface layer, a user profile management layer, an encryption management layer, a protocol management layer and a communication management layer.

The Trusted Service Manager can consolidate/integrate/ simplify various services with service providers (e.g., banks, phone companies and service providers).

Figure 2H:
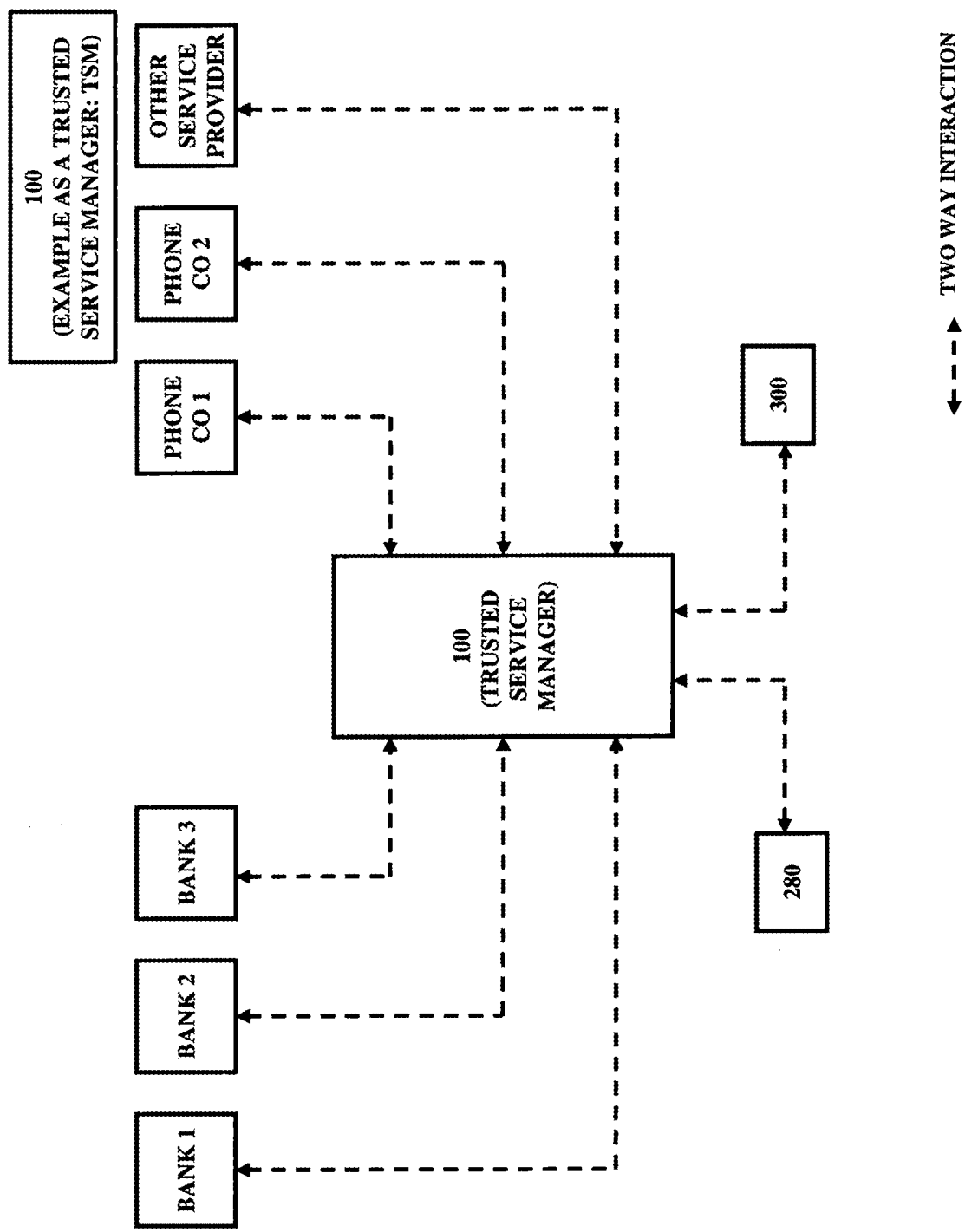

FIG. 2H illustrates how the social wallet 100 can function as the Trusted Service Manager to enable social electronic commerce, utilizing the social wallet electronic module 280 and/or the mobile internet device 300. The Trusted Service Manager can be coupled with various service providers such as: banks, phone companies and service providers.

Figure 3A:
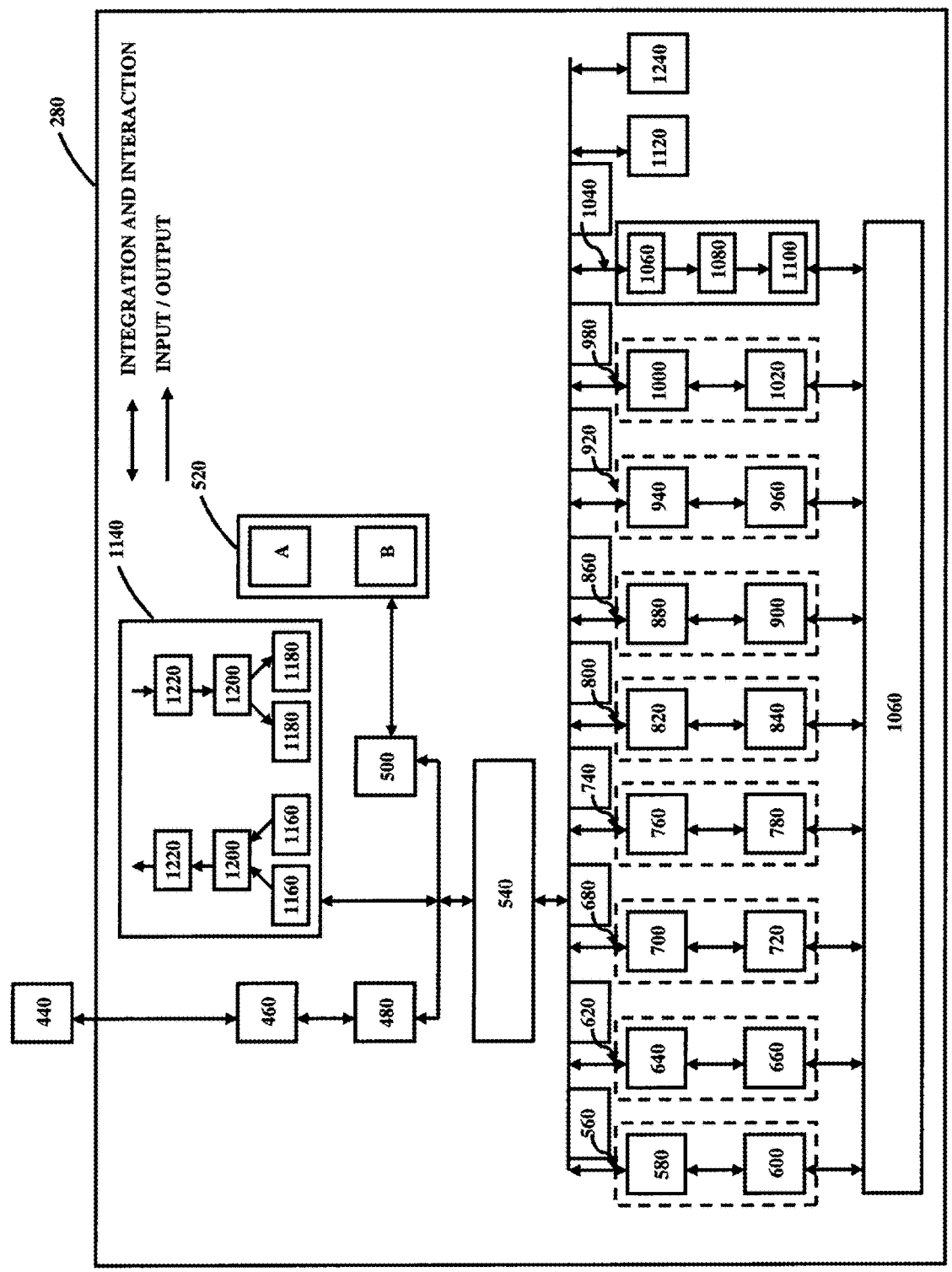
FIG. 3A illustrates a block diagram of a social wallet electronic module, according to one embodiment of the present invention.

FIG. 3A illustrates a block diagram of the social wallet electronic module 280 (preferably in a small form factor e.g., a SD/mini SD).

An external universal serial bus port 440 can connect with a universal serial bus (USB) connector 460. The universal serial bus connector 460 can be electrically coupled with a universal serial bus interface 480. The universal serial bus interface 480 can be electrically coupled with a computer readable medium (CRM) interface 500.

The computer readable medium interface 500 can be electrically coupled with a solid state non-volatile (e.g., a flash/memristor based ReRAM) storage/memory 520 to store information. The solid state non-volatile storage/ memory 520 can be partitioned to have both a private password protected storage/memory section (520-A) and a publicly viewable storage/memory section (520-B).

Furthermore, the solid state non-volatile memory 520 can store legally approved electronic cash (e.g., Bitcoins, digital gold currency and webmoney with traceable serial numbers).

Both the universal serial bus interface 480 and computer readable medium interface 500 can be electrically coupled with a microcontroller 540.

A biometric (e.g., a finger print/retinal scan) sensor miniature electronic module 560 (an interface 580 and a component 600) can be electrically coupled with the microcontroller 540. The biometric sensor miniature electronic module 560 can enhance the security of the social wallet electronic module 280 or the user 160 by matching the stored biometric scan and an instant biometric scan at a point of presence or at a point of use for both online (Internet purchase) and off line (retail purchase) applications.

An advanced finger print sensor module can be fabricated/ constructed by combining a silica colloidal crystal with a rubber, wherein the silica colloidal crystal can be dissolved in dilute hydrofluoric (HF) acid, leaving air voids in the rubber and thus creating an elastic photonic crystal. The elastic photonic crystal emits an intrinsic color, displaying three-dimensional (3-D) shapes of ridges, valley and pores of a finger print, when a finger is pressed onto the advanced finger print sensor. Details on the advanced finger print sensor have been described/disclosed in U.S. Non-Provisional patent application Ser. No. 11/952,001, entitled "DYNAMIC INTELLIGENT BIDIRECTIONAL OPTICAL AND WIRELESS ACCESS COMMUNICATION SYSTEM", filed on Dec. 6, 2007 (now U.S. Pat. No. 8,073,331, issued on Dec. 6, 2011).

A near-field communication miniature electronic module 620 (an interface 640 and a component 660) can be electrically coupled with the microcontroller 540. Near-field communication is a close proximity range 13.56 MHz wireless (or radio) protocol.

Near-field communication has two key components: an initiator and a target. The initiator actively generates a radio frequency (RF) field that can electrically power a passive target without a battery.

A near-field communication tag contains simple data to perform a task (e.g., paying for the product and/or service and exchanging data between users). The near-field communication tag can securely store data (e.g., a personal identification number, debit/credit card information, loyalty card information, health record, physical access information, logical access information and digital rights access for local digital rights storage). But the near-field communication tag can also be re-writeable and be used as a proximity based wireless charger.

A Wibree (a low electrical power, short-range wireless (or radio) protocol) miniature electronic module 680 (an interface 700 and a component 720) can be electrically coupled with the microcontroller 540.

A DASH7 (a low electrical power, -moderate-range wireless (or radio) protocol) miniature electronic module 740 (an interface 760 and a component 780) can be electrically coupled with the microcontroller 540. DASH7's electrical power requirements are about 10% of its next closest competitor (IEEE 802.15.4) and an even smaller fraction of WiFi and Bluetooth. With DASH7 miniature electronic module 720, the user 160 passing by a restaurant at a low velocity (e.g., about 5 mph) could simply click a "get info" button to seek a customer review (or the merchant score) of the restaurant, before the user 160 decides to eat at the restaurant or not.

A Bluetooth miniature electronic module 800 (an interface 820 and a component 840) can be electrically coupled with the microcontroller 540 to transmit and/or receive data.

A WiFi miniature electronic module 860 (an interface 880 and a component 900) can be electrically coupled with the microcontroller 540 to transmit and/or receive data.

An ultra wideband miniature electronic module 920 (an interface 940 and a component 960) can be electrically coupled with the microcontroller 540 to transmit and/or receive a vast quantity of data (e.g., a movie) in a short period of time.

A 60 GHz millimeter wave miniature electronic module 980 (an interface 1000 and a component 1020) can be electrically coupled with the microcontroller 540 to transmit and/or receive a vast quantity of data (e.g., a movie) in a short period of time. The 60 GHz millimeter wave miniature electronic module 980 can enable applications such as (a) wireless docking and (b) distributed storage.

A software-defined radio 1040 can be fabricated/constructed by integrating a tunable antenna 1060, a carbon nanotube tunable filter 1080 and an analog to digital converter 1100.

The tunable antenna 1060 can tune in between 2 GHz and 3 GHz by utilizing a carbon nanotube. The tunable antenna 1060 can merge/integrate many antennas into one single antenna.

The software-defined radio 1040 and tunable antenna 1060 can be electrically coupled with the microcontroller 540.

Additionally, a sensor (e.g., a wireless sensor-radio frequency identification (RFID)) 1120 can be electrically coupled with the microcontroller 540.

Furthermore, a line-of-sight optical transceiver 1140 (integrating an array of multi-color light source modulators 1160, an array of photodiodes 1180, two (2) waveguide combiner/decombiner 1200 and two (2) lenses 1220) can be electrically coupled with the microcontroller 540. The optical transceiver 1140 can transmit and/or receive a vast quantity of data (e.g., a movie) in a short period of time.

Additionally, an electrical power provider component (a thick-film/thin-film battery/solar cell/micro fuel-cell/supercapacitor) 1240 can be electrically coupled with the microcontroller 540. It should be noted that the electrical power provider component 1240 can be enabled for wireless (e.g., near-field communication based) charging.

Furthermore, the microcontroller 540 can be replaced by a high-performance microprocessor 1360.

Figure 3B:
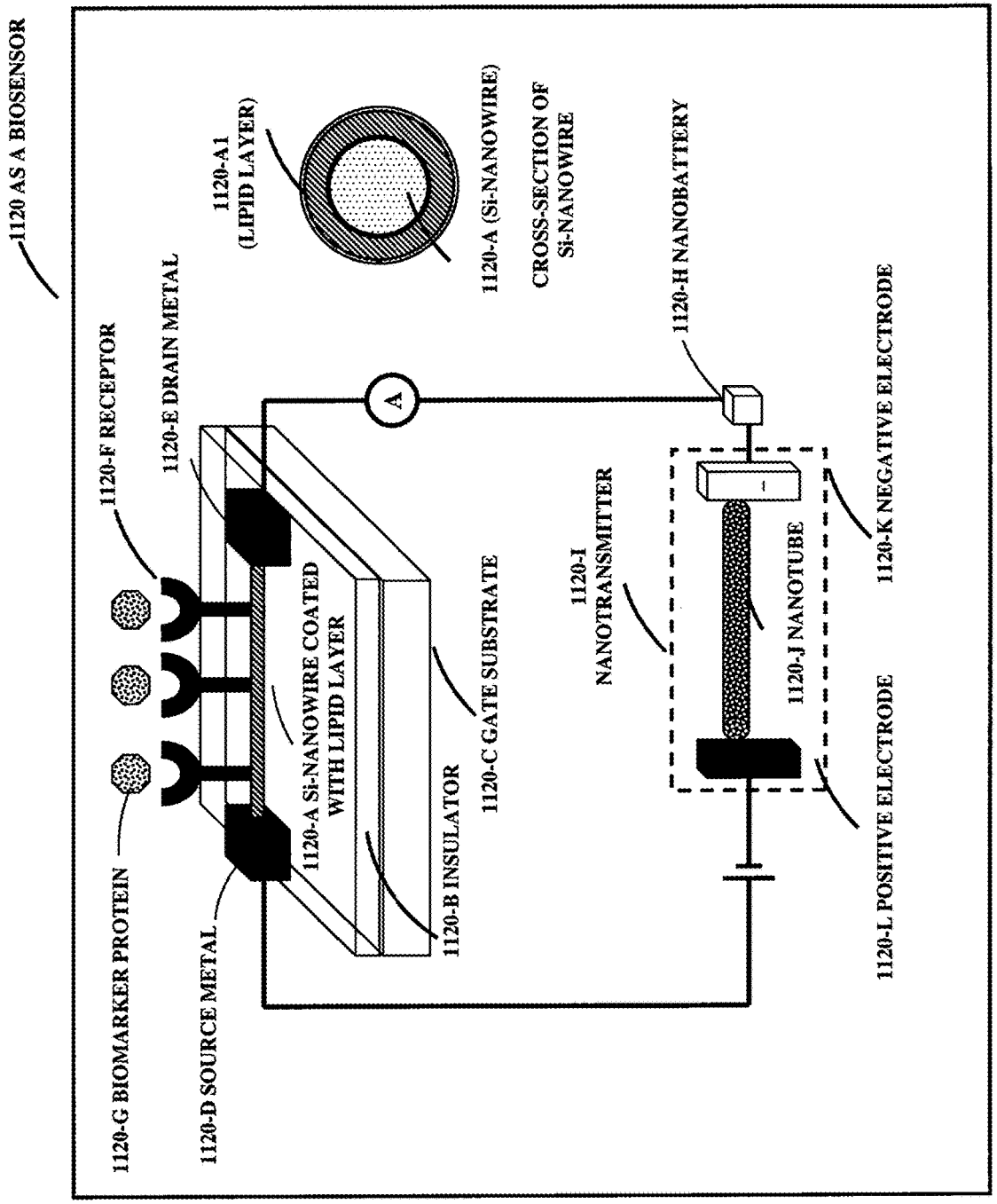
FIGS. 3B and 3C illustrate a block diagram of an application of a biosensor (as a sensor) of the social wallet electronic module, according to one embodiment of the present invention.
Figure 3C:
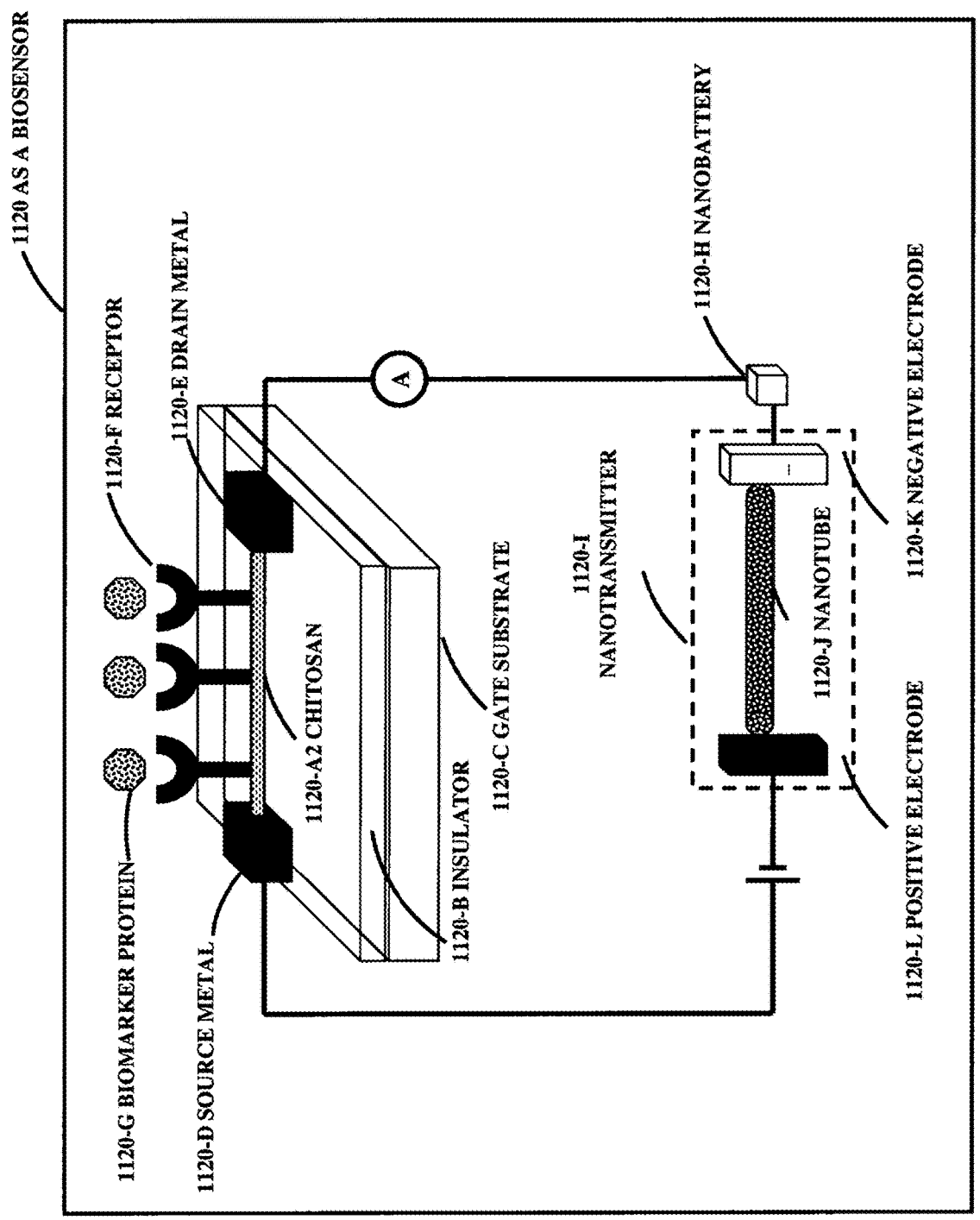

Furthermore, the sensor 1120 can be a biosensor, wherein two embodiments of the biosensor are described in FIGS. 3B and 3C along with the Table-1 and Table-2:

TABLE 1

| FIG. 3B Legend | Description |
| --- | --- |
| 1120-A | Silicon Nanowire |
| 1120-A1 | Lipid Layer |
| 1120-B | Insulator (e.g., Silicon Dioxide) |
| 1120-C | Gate (e.g., Silicon Substrate) |
| 1120-D | Source Metal |
| 1120-E | Drain Metal |
| 1120-F | Receptor (e.g., Antibody Or Aptamer) |
| 1120-G | Biomarker Protein |
| 1120-H | Nanobattery |
| 1120-I | Nanotransmitter |
| 1120-J | Nanotube (e.g., Carbon Nanotube) |
| 1120-K | Negative Electrode |
| 1120-L | Positive Electrode |

TABLE 2

| FIG. 3C Legend | Description |
| --- | --- |
| 1120-A2 | Chitosan |
| 1120-B | Insulator (e.g., Silicon Dioxide) |
| 1120-C | Gate (e.g., Silicon Substrate) |
| 1120-D | Source Metal |
| 1120-E | Drain Metal |
| 1120-F | Receptor (e.g., Antibody Or Aptamer) |
| 1120-G | Biomarker Protein |
| 1120-H | Nanobattery |
| 1120-I | Nanotransmitter |
| 1120-J | Nanotube (e.g., Carbon Nanotube) |
| 1120-K | Negative Electrode |
| 1120-L | Positive Electrode |

FIG. 3B illustrates an application of the sensor 1120, as the biosensor, which can be integrated with the social wallet electronic module 280. In the sensor 1120, a silicon nanowire field effect transistor (FET), a source is identified by S, a drain is identified by D and a gate is identified by G. Furthermore, the silicon nanowire can be coated with a lipid layer and integrated with receptors on the lipid layer. The receptors can chemically bind with a biomarker protein (e.g., a disease biomarker protein) thus giving rise to electrical signals (due to changes in the electrical properties of the silicon nanowire), further transmitted by a nanotube (e.g., a carbon nanotube) based wireless (or radio) transmitter. The nanotube based wireless (or radio) transmitter can be electrically powered with a nanobattery.

FIG. 3C illustrates a disease detection application of the sensor 1120, as the biosensor, which can be integrated with the social wallet electronic module 280. In 1120, chitosan proton (ionic) field effect transistor ($H^+$ FET), a source is identified by S, a drain is identified by D and a gate is identified by G. Furthermore, chitosan can be integrated with receptors. The receptors can chemically bind with a biomarker protein (e.g., a disease biomarker protein)—thus giving rise to electrical signals (due to changes in the electrical properties of chitosan), further transmitted by a nanotube (e.g., a carbon nanotube) based wireless (or radio) transmitter. The nanotube based wireless (or radio) transmitter can be electrically powered with the nanobattery.

Furthermore, the sensor 1120, as the biosensor can be integrated with the near-field communication miniature electronic module 620 on a human body to enable a smart biosensor, to transmit vital health data to a near-field communication terminal. Alternatively, at least the sensor 1120, as the biosensor can be implanted within a human body, utilizing a biocompatible outer case.

Figure 3D:
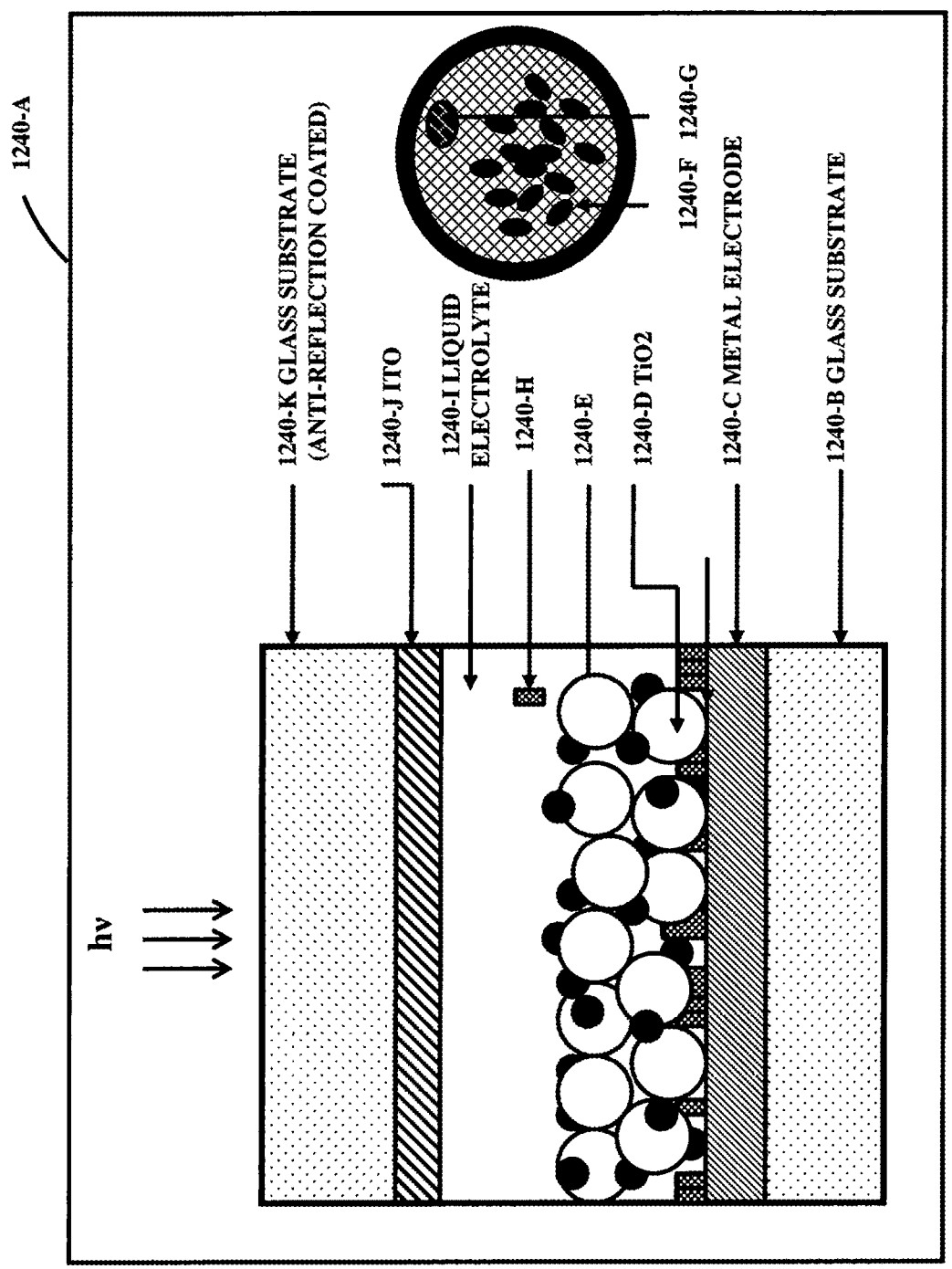
FIGS. 3D, 3E and 3F illustrate cross-sections of various configurations of a solar cell (an electrical power provider component) of the social wallet electronic module and/or mobile internet device, according to one embodiment of the present invention.

FIG. 3D illustrates a solar cell 1240-A as an electrical power provider component. About 2 microns thick meso-porous $TiO_2$ thin-film 1240-D can be coated with nanocrystals/nanoshells 1240-E. The nanocrystals/nanoshells 1240-E can cage/encapsulate light-absorbing organic dye molecules (e.g., porphyrins and/or phthalocyanines) 1240-F. Furthermore, the nanocrystals/nanoshells 1240-E can contain another specific molecule 1240-G for energy transfer upon excitation.

The nanocrystals/nanoshells 1240-E can be also varied in diameter to have an absorption over wider wavelength range in order for the solar cell 1240-A to be more efficient (for light to electricity conversion).

Furthermore, the solar cell 1240-A could be made more efficient (for light to electricity conversion) with an addition of an array of nanotubes (e.g., carbon or boron nitride nanotubes) 1240-H.

The meso-porous $TiO_2$ thin-film 1240-D can be sandwiched between two electrodes: indium tin oxide transparent front electrode 1240-J and back metal (e.g., aluminum, silver or platinum) electrode 1240-C.

Furthermore, the back metal electrode 1240-C can be fabricated/constructed with nanocorrugated plasmonic reflectors to trap more residual light inside the solar cell 1240-A.

The meso-porous $TiO_2$ thin-film 1240-D can be immersed within a liquid ionic electrolyte solution 1240-I.

Figure 3E:
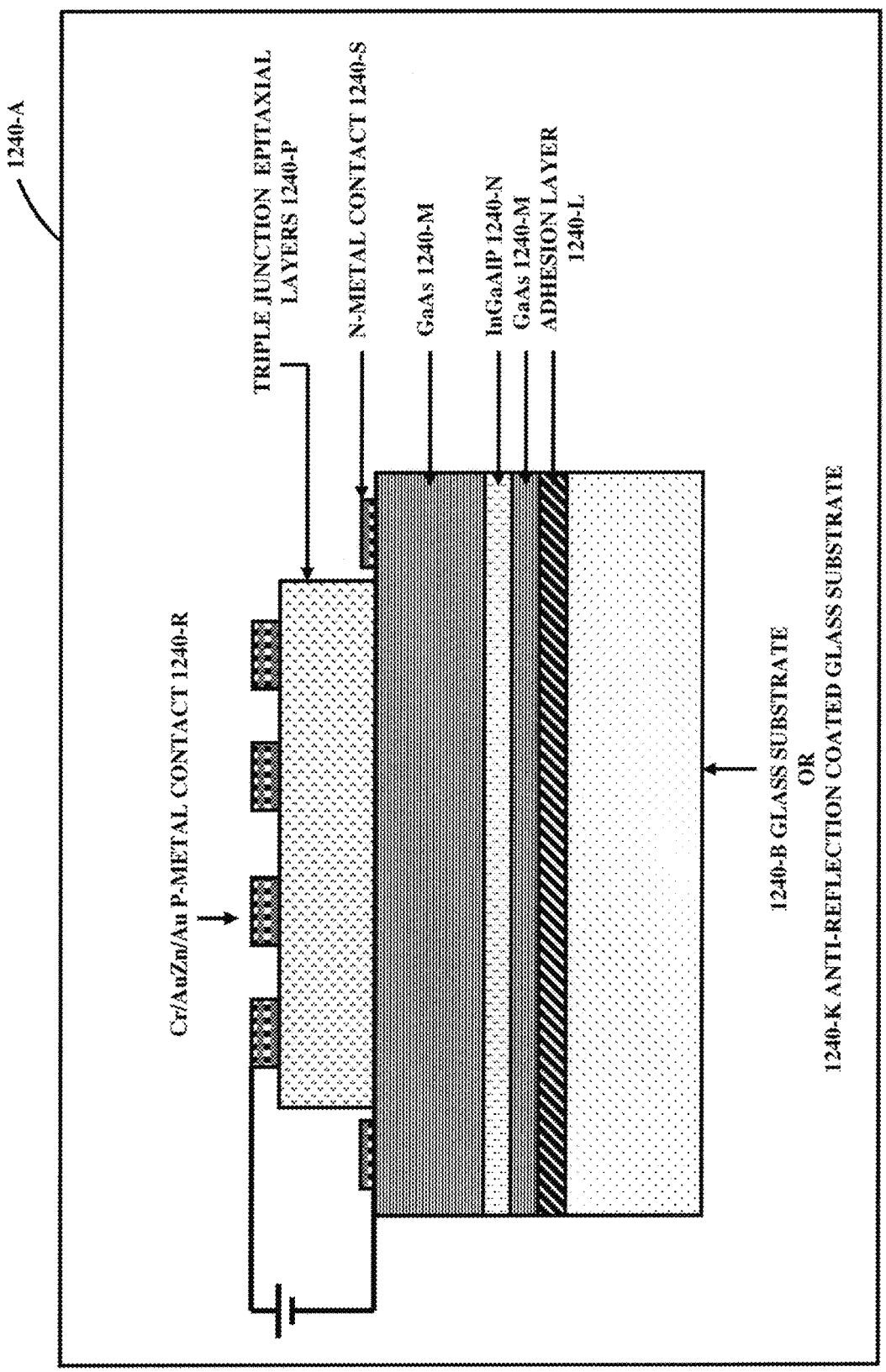

FIG. 3E illustrates the solar cell 1240-A as the electrical power provider component. Triple junction semiconductor epitaxial layers 1240-P can be purchased from Microlink Devices. The critical element of this embodiment is (a) chemically separating (by selectively etching 50 nanometers thick AlAs layer in hydrofluoric acid), (b) lifting (by covering the patterned front device side with a black wax) triple junction semiconductor epitaxial layers 1240-P, all other relevant layers (such as GaAs layer 1240-M and InGaAlP layer 1240-N), p-metallization 1240-R and n-metallization 1240-S, (c) bonding onto the glass substrate 1240-B with an adhesion layer 1240-L and (d) finally dissolving the black wax in trichloroethylene (TCE).

Figure 3F:
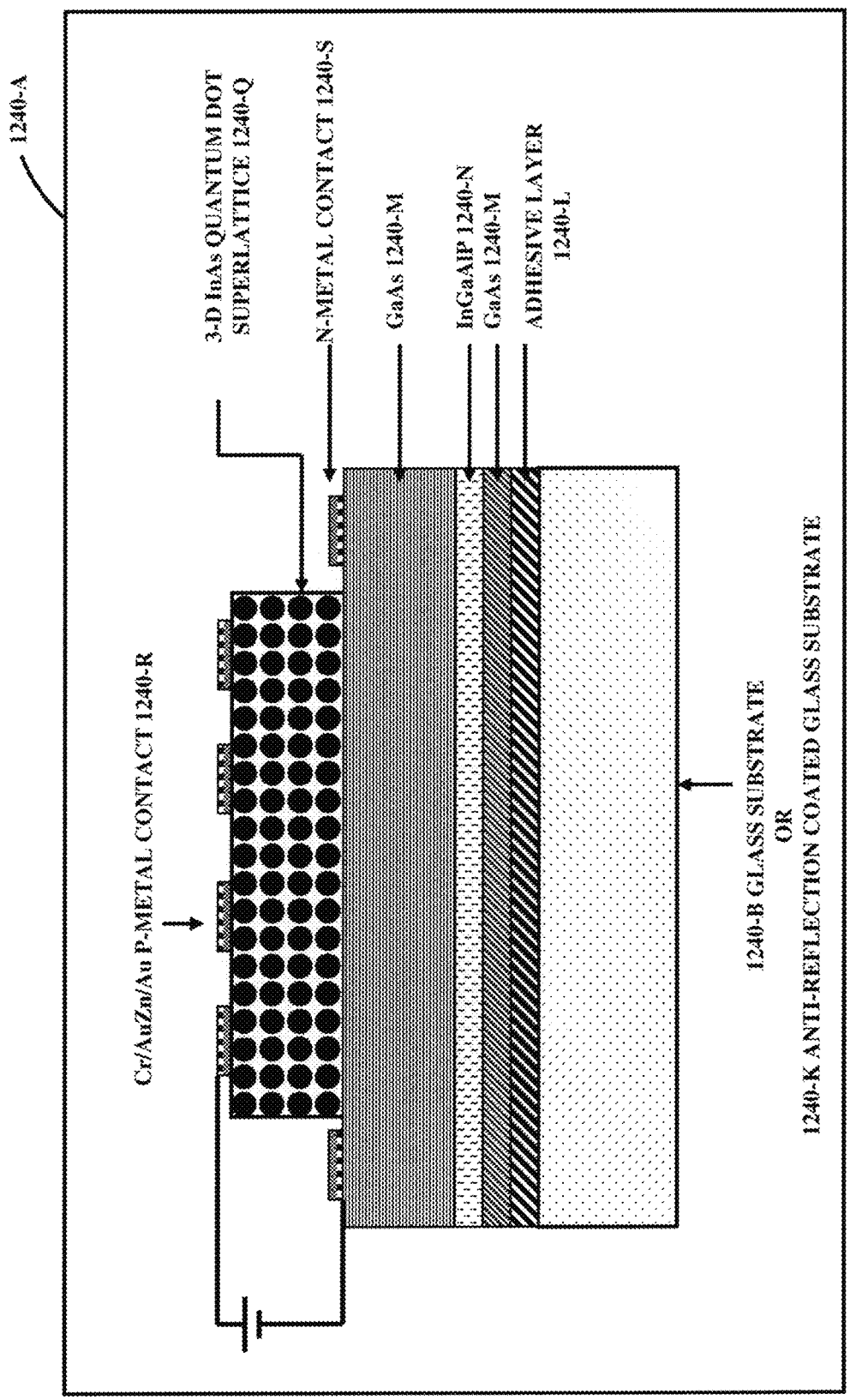

FIG. 3F illustrates a cross-section of the solar cell 1240-A as the electrical power provider component. The critical element of this embodiment is (a) chemically separating (by selectively etching 50 nanometers thick AlAs layer in hydrofluoric acid), (b) lifting (by covering the patterned front device side with a black wax) three-dimensional quantum dot superlattice of InAs 1240-Q, all other relevant layers (such as GaAs layer 1240-M and InGaAlP layer 1240-N), p-metallization 1240-R and n-metallization 1240-S, (c) bonding onto the glass substrate 1240-B with an adhesion layer 1240-L and (d) finally dissolving the black wax in trichloroethylene.

Figure 3G:
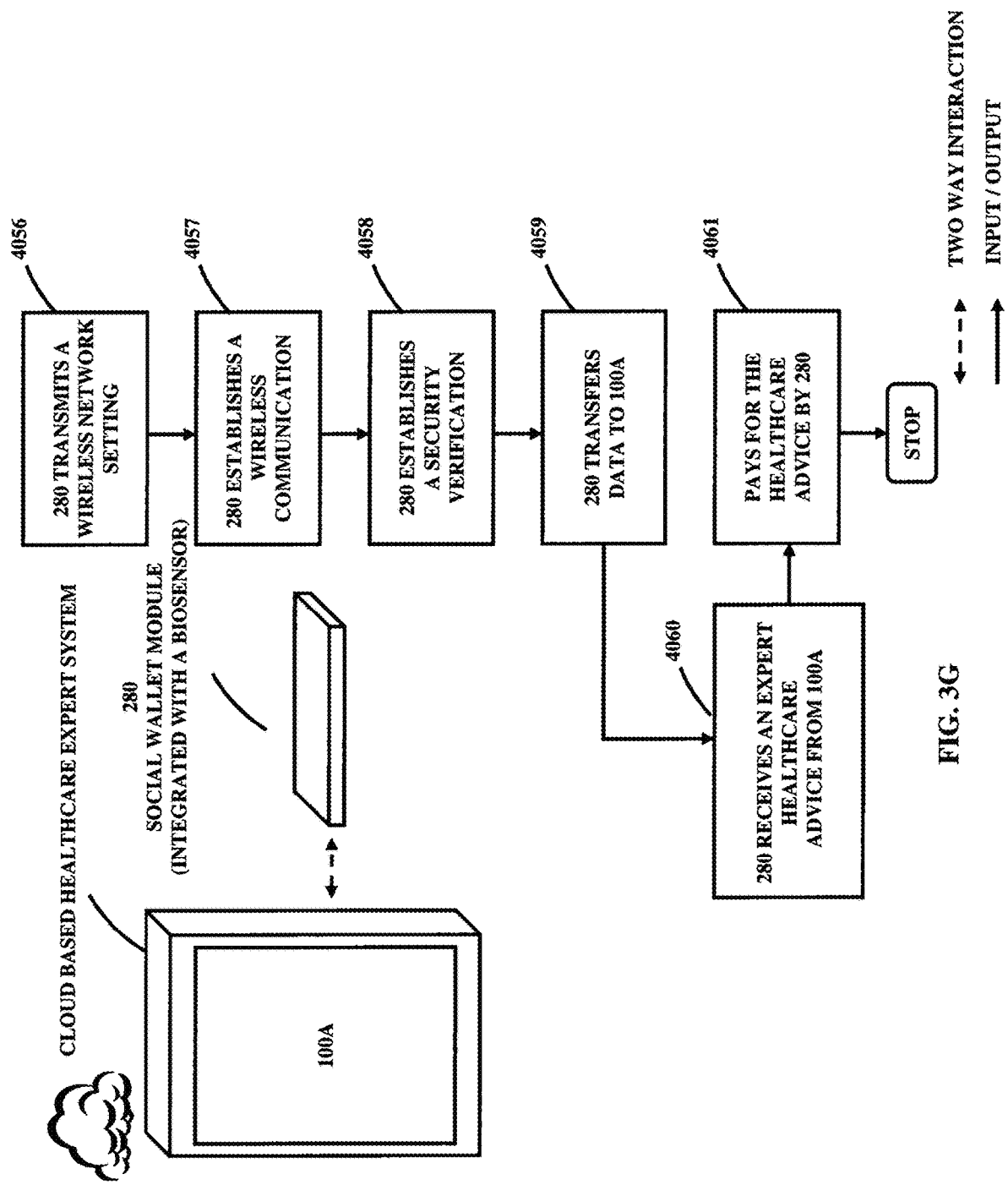
FIG. 3G illustrates a healthcare (as a virtual doctor) related application of the social wallet electronic module, according to one embodiment of the present invention.

FIG. 3G illustrates a healthcare related application of the social wallet electronic module 280: how the social wallet electronic module 280 can be utilized to obtain healthcare related advice from a healthcare expert system (a virtual doctor) at a cloud server. The social wallet electronic module 280 can be integrated with the sensor 1120 as the biosensor or a point-of-care diagnostic device. In step 4056, the social wallet electronic module 280 transmits wireless (or radio) network settings to the cloud based healthcare expert system (the virtual doctor) 100A. In step 4057, the social wallet electronic module 280 establishes wireless (or radio) connection with the cloud based healthcare expert system (the virtual doctor) 100A. In step 4058, the social wallet electronic module 280 establishes security verification with the cloud based healthcare expert system (the virtual doctor) 100A. In step 4059, the social wallet electronic module 280 transfers the user's health related data to the cloud based healthcare expert system (the virtual doctor) 100A. In step 4060, the social wallet electronic module 280 receives expert healthcare advice from the cloud based healthcare expert system (the virtual doctor) 100A. In step 4061, the user 160 pays by the social wallet electronic module 280 for the expert advice received from the cloud based healthcare expert system (the virtual doctor) 100A. Various embodiments of the point-of-care diagnostic device have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 (which claims benefit of priority to: U.S. Provisional Patent Application No. 62/230,249 entitled "SYSTEM AND METHOD OF AMBIENT/PERVASIVE USER/HEALTHCARE EXPERIENCE", filed on Jun. 1, 2015), U.S. Non-Provisional patent application Ser. No. 14/120,835 entitled "AUGMENTED REALITY PERSONAL ASSISTANT APPARATUS", filed on Jul. 1, 2014 and U.S. Non-Provisional patent application Ser. No. 13/663,376 entitled "OPTICAL BIOMODULE FOR DETECTION OF DISEASES", filed on Oct. 29, 2012 (or "OPTICAL BIOMODULE FOR DETECTION OF DISEASES", U.S. Pat. No. 9,557,271, issued on Jan. 31, 2017).

Figure 3H:
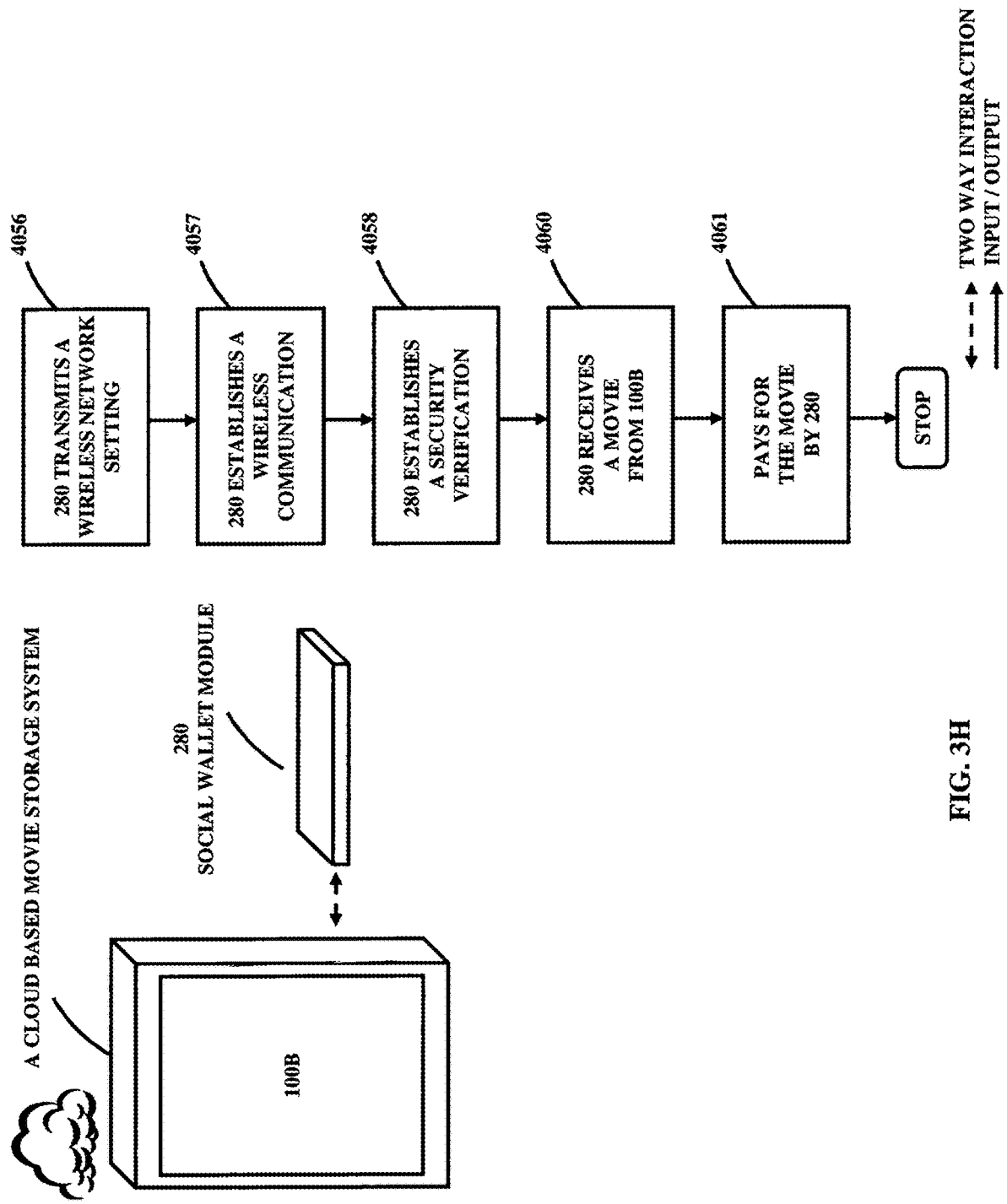
FIG. 3H illustrates a consumer related application of the social wallet electronic module, according to one embodiment of the present invention.

FIG. 3H illustrates a consumer related application of the social wallet electronic module 280: how the social wallet electronic module 280 can be utilized to obtain a movie from the cloud based movie storage system 100B. In step 4056, the social wallet electronic module 280 transmits a wireless (or radio) network setting(s) to the cloud based movie storage system 100B. In step 4057, the social wallet electronic module 280 establishes a wireless (or radio) connection with the cloud based movie storage system 100B. In step 4058, the social wallet electronic module 280 establishes a security verification with the cloud based movie storage system 100B. In step 4060, the social wallet electronic module 280 receives (downloads) a movie from the cloud based movie storage system 100B. In step 4061, the user 160 pays for the movie received (downloaded) from the cloud based movie storage system 100B by the social wallet electronic module 280 for a specified period of time, after the specified period of time, the received (downloaded) movie can be automatically disabled by a set of instructions (e.g., computer codes).

Alternatively, a movie storage system can be located at widely distributed (and conveniently located) kiosks, instead of the cloud based movie storage system 100B.

Figure 4:
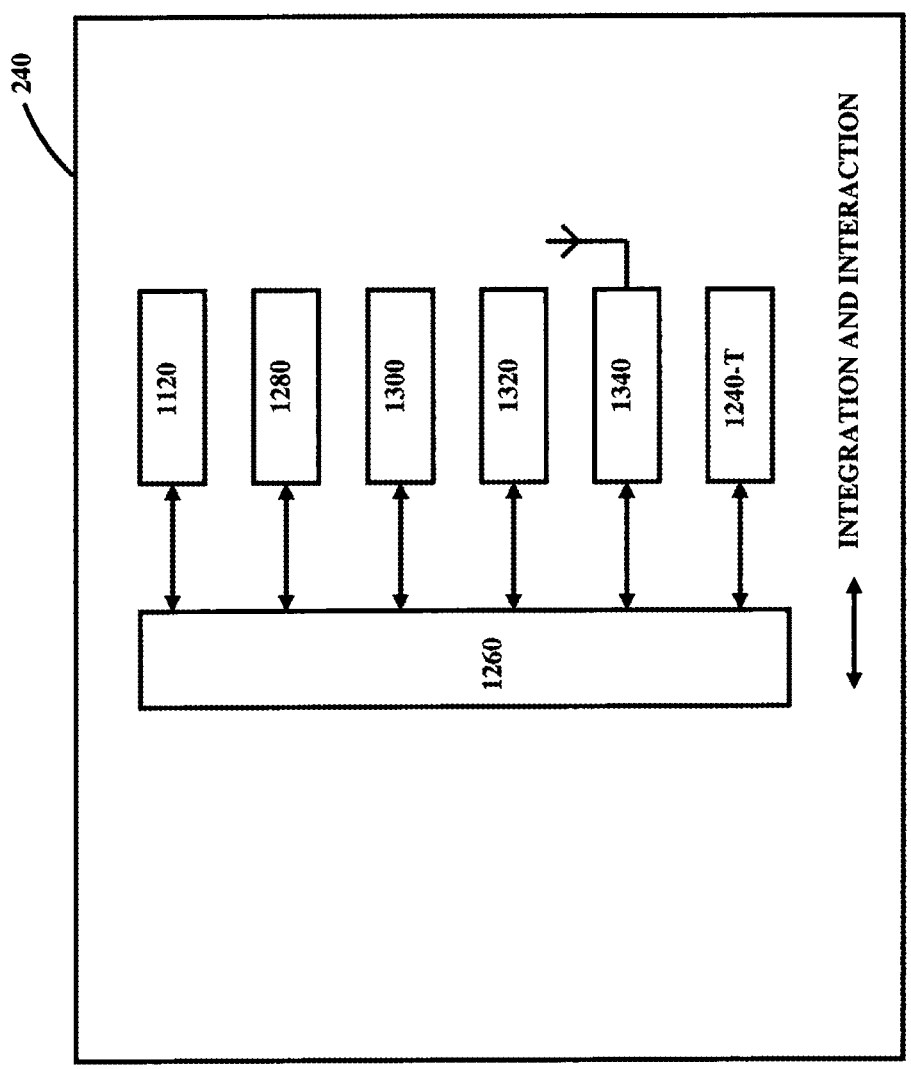
FIG. 4 illustrates a block diagram of an object, according to one embodiment of the present invention.

FIG. 4 illustrates a block diagram of the object 240. The object 240 has ultra-low electrical power consumption and miniature medium performance microprocessor (e.g., an Ambiq Micro or InAs-on-Insulator based microprocessor or a memristor) 1260, which can be electrically coupled with: (a) a sensor (e.g., a wireless sensor-a radio frequency identification) 1120, (b) an optional IP/micro IP/light weight IP address 1280, (c) a miniature memory/storage (e.g., a memristor) 1300, (d) an embedded tiny operating algorithm/ executable instructions 1320 (e.g., a Tiny OS), (e) a miniature low electrical power "object-specific" miniature wireless (or radio) transmitter (e.g., a radio frequency identification and/or a Wibree and/or a Bluetooth and/or a WiFi and/or a near-field communication) with a miniature antenna 1340 and (f) an "object-specific" electrical power provider component 1240-T (e.g., the solar cell 1240-A in a miniature form factor).

Furthermore, the object 240 can have an outer external case. The object 240 can also be a biological object on or within (e.g., implanted utilizing the outer external case, which is biocompatible) a human body.

The object 240 can utilize semiconductor fabrication, micro-electromechanical systems fabrication, plastic electronics fabrication, printed electronics fabrication, multichip module fabrication (packaging), three-dimensional fabrication (packaging) and microfluidic fabrication.

The array of objects 240s can connect to the node (e.g., the node with an internet connection) 260. The node 260 can map, sense, measure, collect, aggregate, compare information collected from the array of objects 240s. The node 260 can share/communicate information with the social wallet 100 and/or electronic social wallet electronic module 280 and/or mobile internet device 300.

The objects 240s and node 260 can self-register with a blockchain for integration. For example, when the object 240/node 260 detects something wrong, it can automatically request a smart repair contract. Additionally, the node 260 can be integrated with an automated agent/bot including a voice/text interface.

Furthermore, the electronic social wallet electronic module 280 and/or mobile internet device 300 can proximity contact or physically contact with the object 240 to communicate for relevant information.

Figure 5A:
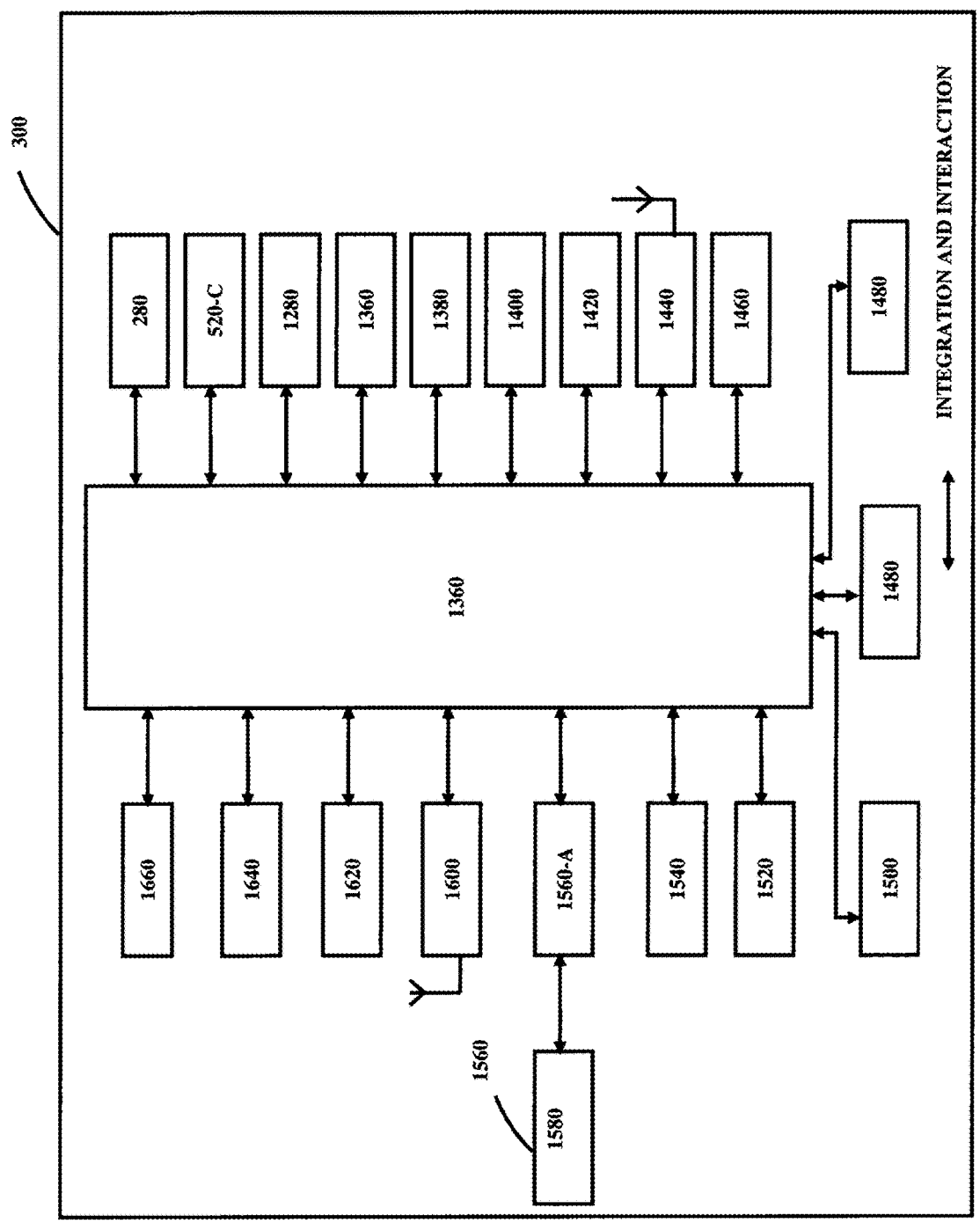
FIG. 5A illustrates a block diagram of the mobile internet device, according to one embodiment of the present invention.

FIG. 5A illustrates a block diagram of the mobile internet device 300. It has the high performance microprocessor (e.g., Intel's x86 based Medfield) 1360, which can be electrically coupled with (a) the social wallet electronic module 280 (in this case the social wallet electronic module 280 does not require the separate microcontroller 540 or the microprocessor 1360, but it shares the high performance microprocessor 1360 of the mobile internet device), (b) a general data storage electronic module 520-C, (c) the IP/micro IP/light weight IP address 1280, (d) a lab-on-chip electronic module (a biological diagnostics electronic module) 1360, (e) an embedded operating algorithm 1380 stored in a general data storage electronic module 520-C, (f) an internet security algorithm (internet firewall/spyware/user-specified security control and authentication) 1400, (g) a one-dimensional/two-dimensional barcode/quick response code reader 1420, (h) a miniature wireless (or radio) electronic module (e.g., a radio frequency identification/Bluetooth/WiFi/global positioning system location (GPS) with an antenna(s)) 1440 for an indoor/outdoor location measurement, (i) an electronic compass 1460, (j) two (2) cameras (a 180 degree rotating camera is preferred, instead of two cameras—one for video chat and one for photo taking) 1480, (k) a video conferencing (integrated with dynamic video compression algorithm) system-on-chip 1500, (l) a display component 1520, (m) a micro-projector 1540, (n) a sketch pad (with a write/erase option) electronic module 1560 with a stylus 1580, (o) a communication wireless (or radio) transceiver electronic module (e.g., WiMax/LTE) with an antenna(s) 1600, (p) a personal awareness assistant miniature electronic module 1620, (q) a voice-to-text-to-voice conversion algorithm 1640 and (r) an algorithm 1660

Furthermore, the mobile internet device 300 has the electrical power provider component. (e.g., battery/solar cell/micro fuel-cell/supercapacitor) 1240. It should be noted that the electrical power provider component 1240 can be enabled for wireless (e.g., near-field communication based) charging.

A multi-touch high definition liquid crystal display (integrated with an array of thin-film transistors on indium gallium zinc oxide) can be utilized as the display component 1520.

Organic light emitting (red, green and blue) diodes driven by an array of organic thin-film transistors on an organic substrate (e.g., plastic) can also be utilized as the rolled up/foldable/stretchable display component 1520. The rolled up/foldable/stretchable display component 1520 can minimize its size related distinction between a portable computer (e.g., a laptop) and the mobile internet device 300.

Additionally, the rolled up/foldable/stretchable display component 1520 can be constructed from a graphene sheet and/or an organic light-emitting diode connecting/coupling/interacting with a printed organic transistor and a rubbery conductor (e.g., a mixture of a carbon nanotube/gold conductor and a rubbery polymer) with a touch/multi-touch sensor.

Furthermore, the display component 1520 can enable a dual-view to show entirely two separate scenes simultaneously.

If both the display component 1520 and electrical power provider component are thinner, then the mobile internet device 300 would be thinner. A thinner organic battery component can be fabricated/constructed as follows: an organic battery utilizes push-pull organic molecules, wherein after an electron transfer process, two positively charged molecules are formed, which are repelled by each other like magnets. By installing a molecular switch an electron transfer process can proceed in an opposite direction. Thus, forward and backward switching of an electron flow can form a basis of an ultra-thin, light weight and electrical power efficient organic battery. Details on the thinner organic battery have been described/disclosed in U.S. Non-Provisional patent application Ser. No. 11/952,001, ENTITLED "DYNAMIC INTELLIGENT BIDIRECTIONAL OPTICAL AND WIRELESS ACCESS COMMUNICATION SYSTEM", filed on Dec. 6, 2007 (now U.S. Pat. No. 8,073,331, issued on Dec. 6, 2011).

Furthermore, the algorithm 1660 includes: (a) a physical search algorithm, (b) an algorithm-as-a-service, (c) an intelligent rendering algorithm (e.g., artificial intelligence, behavior modeling, data interpretation, data mining, fuzzy logic, machine vision, natural language processing, neural network, pattern recognition and reasoning modeling) and (d) a self-learning (including relearning) algorithm. It should be noted that the self-learning (including relearning) algorithm can include a self-learning artificial intelligence algorithm and/or a self-learning neural network algorithm In the context of the mobile internet device 300, data can be compared with respect to a set of parameters to learn or relearn continuously by analyzing patterns of data, where patterns of data can consist/utilize/couple with the algorithm 1660.

The algorithm 1660 of the mobile internet device 300 includes the intelligent rendering algorithm (e.g., artificial intelligence, behavior modeling, data interpretation, data mining, fuzzy logic, machine vision, natural language processing, neural network, pattern recognition and reasoning modeling). Additionally, the mobile internet device 300 can be integrated with an automated agent/bot (including a voice/text interface), enhanced by the algorithm 1660.

In the context of the social wallet 100, data can be compared with respect to a set of parameters to learn or relearn continuously by analyzing patterns of data, where patterns of data can consist/utilize/couple with the fuzzy logic algorithm 360, the intelligence rendering algorithm 400 and the self-learning (including relearning) algorithm 420. It should be noted that the self-learning (including relearning) algorithm 420 can include a self-learning artificial intelligence algorithm and/or a self-learning neural network algorithm Furthermore, this continually learned analysis along with the predictive algorithm 380 can enable the social wallet 100 to identify a set of users with particular parameters for a targeted advertisement.

The antenna for the communication wireless (or radio) transceiver 1600 of the mobile internet device 300 can be fabricated/constructed from metamaterial. Metamaterial is a material of designer crystal structure combining two materials (e.g., lead selenide and iron oxide).

Furthermore, the antenna can be integrated with/onto an outer external case of the mobile internet device 300.

The outer external case of the mobile internet device 300 can be fabricated/constructed from a nano-engineered aluminum/magnesium alloy and/or a liquid metal alloy and/or glass.

The outer external case of the mobile internet device 300 can also be fabricated/constructed from carbon fibers embedded with plastic. Carbon fibers can be inserted into an injection mold of a plastic film and bonded to the molten injection mold of the plastic film, thereby forming a composite material of the carbon fibers and plastic film.

Figure 5B:
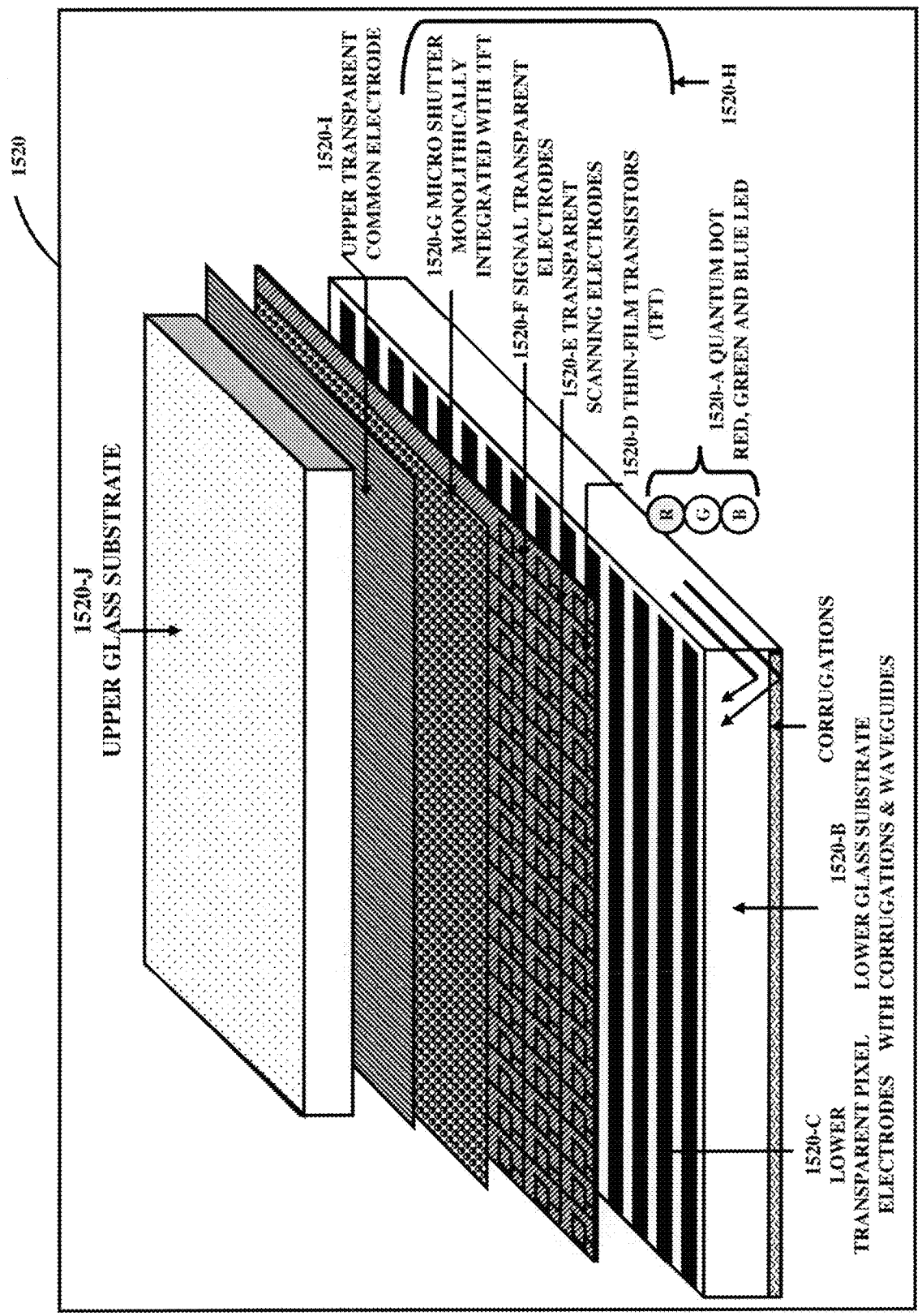
FIG. 5B illustrates a cross-section of a display component of the mobile internet device, according to one embodiment of the present invention.

FIG. 5B illustrates a cross-section of the display component 1520 of the mobile internet device 300, which utilizes highly efficient quantum dot light emitting diodes 1520-A (red, green and blue) incident at an angle with respect to the lower glass substrate 1520-B. The lower glass substrate 1520-B has built-in corrugations and waveguides to enable reflection of an incident light from the quantum dot light emitting diodes.

Table-3 below describes subcomponents required to fabricate/construct the display component 1520. The critical subcomponents are micro-electromechanical systems micro shutters, which are monolithically integrated with an array of thin-film transistors (TFTs) (e.g., fabricated/constructed on zinc oxide or zinc-indium-tin oxide or graphene oxide).

TABLE 3

FIG. 5B
Legend | Description
--- | ---
1520-A | Quantum Dot Light Emitting Diodes (Red, Green & Blue)
1520-B | Lower Glass Substrate With Built-In Corrugations & Waveguides
1520-C | Array of Transparent Lower Pixel Electrodes
1520-D | Array of Thin-Film Transistors
1520-E | Scanning Transparent Electrodes
1520-F | Signal Transparent Electrodes
1520-G | Micro-Electromechanical Systems Micro Shutters Monolithically Integrated With A Thin-Film Transistor
1520-H | Monolithic Integration of 1520-D, 1520-E, 1520-F & 1520-G
1520-I | Transparent Upper Common Electrode
1520-J | Upper Glass Substrate This can enable an efficient high brightness display component 1520 at lower electrical power consumption, eliminating two (2) polarizer filter films, color filter and liquid crystal. This is substantially compatible with standard display component manufacturing methods/processes.

Furthermore, a quantum dot white light emitting diode (with a specific thin-film color filter (to transmit only optically filtered red or green or blue light), preferably located below the upper glass substrate) can be used instead of a quantum dot red light emitting diode, a quantum dot green light emitting diode and a quantum dot blue light emitting diode.

The thin-film transistor 1520-D located at each pixel can control an image at each pixel of the display component 1520. However, the thin-film transistor 1520-D can also have a light sensing circuitry to sense the light reaching the pixel of the display component 1520 from its surroundings—thus enabling a possibility of new user experience with the display component 1520.

Figure 5C:
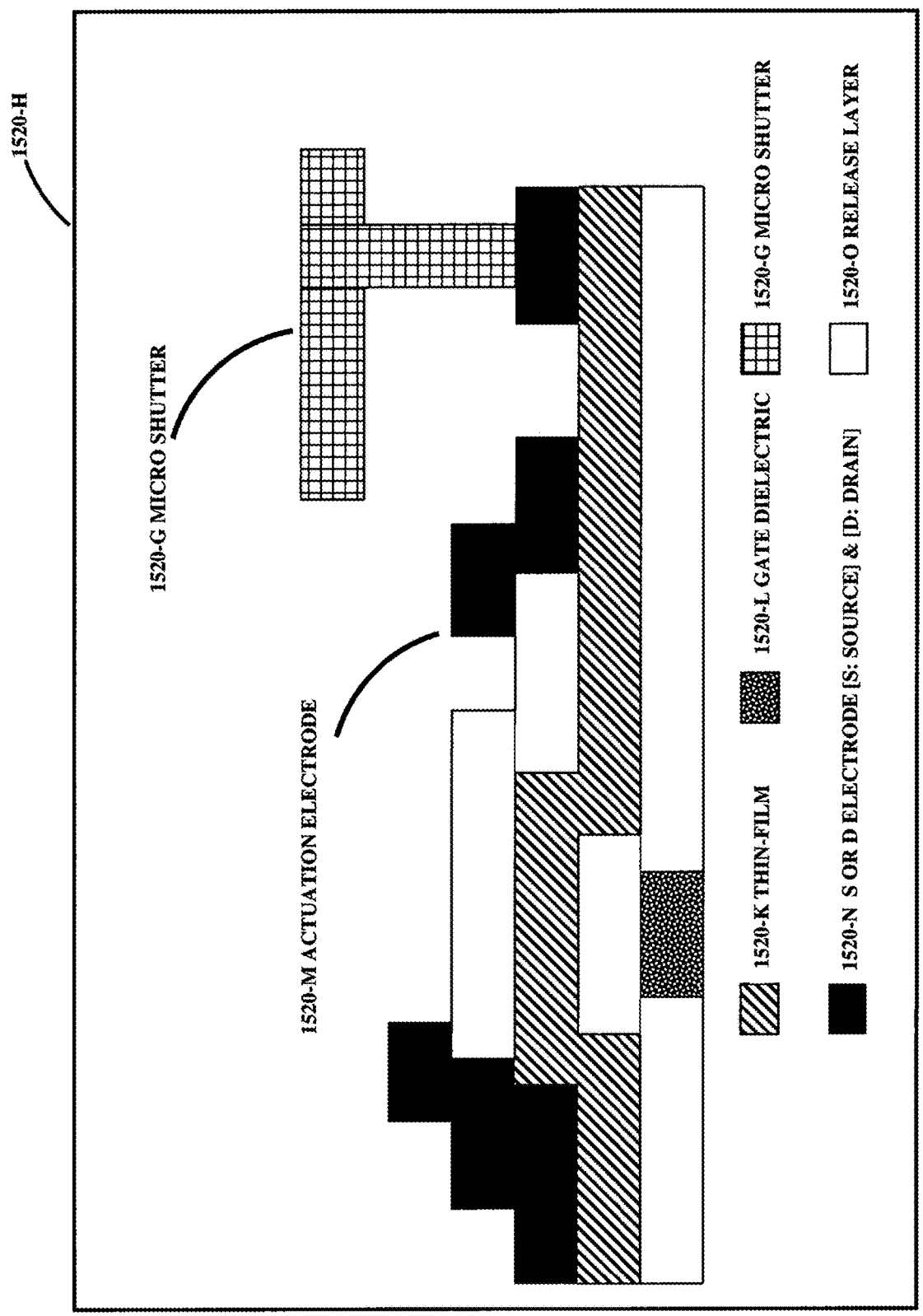
FIG. 5C illustrates a cross-section of a micro-electromechanical systems (MEMS) micro shutter, monolithically integrated with an array of thin-film transistors, according to one embodiment of the present invention.

FIG. 5C illustrates 1520-H: a micro-electromechanical systems micro shutter 1520-G, which can be monolithically integrated with an array of thin-film transistors 1520-D (e.g., fabricated/constructed on zinc oxide or zinc-indium-tin oxide or graphene oxide).

The Table-4 below describes subcomponents required to fabricate/construct the micro-electromechanical systems micro shutter 1520-G, which can be monolithically integrated with an array of thin-film transistors 1520-D (e.g., fabricated/constructed on zinc oxide or zinc-indium-tin oxide or graphene oxide).

TABLE 4

Figure 5D:
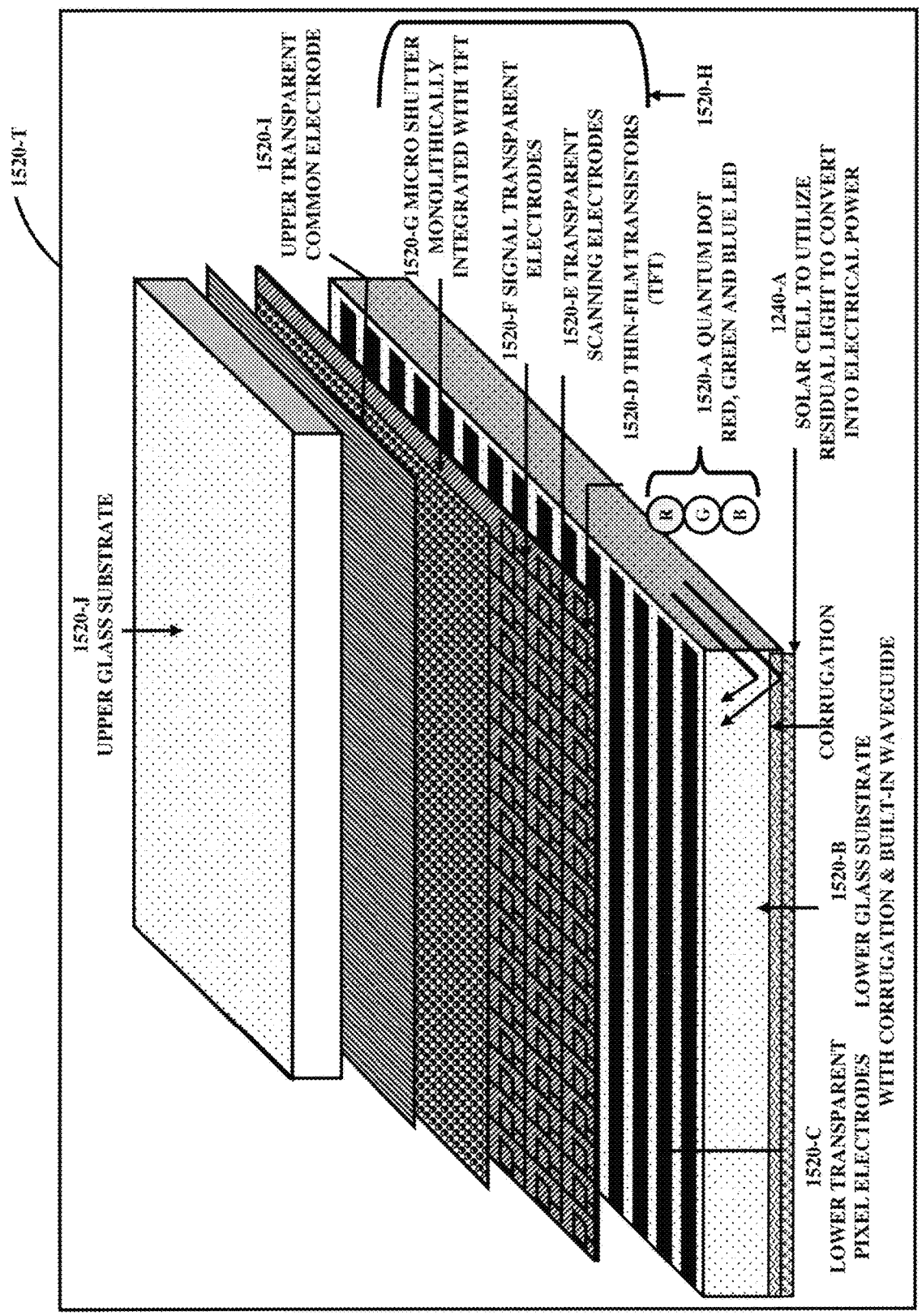
FIG. 5D illustrates a cross-section of the display component integrated with a solar cell of the mobile internet device, according to one embodiment of the present invention.

FIG. 5C Legend | Description
--- | ---
1520-K | Thin-Film
1520-L | Gate Dielectric
1520-G | Micro Shutter
1520-N | Source Electrode Or Drain Electrode
1520-M | Actuation Electrode
1520-O | Release Layer FIG. 5D illustrates a cross-section of another display component 1520-T integrated with the solar cell 1240-A.

Figure 5E:
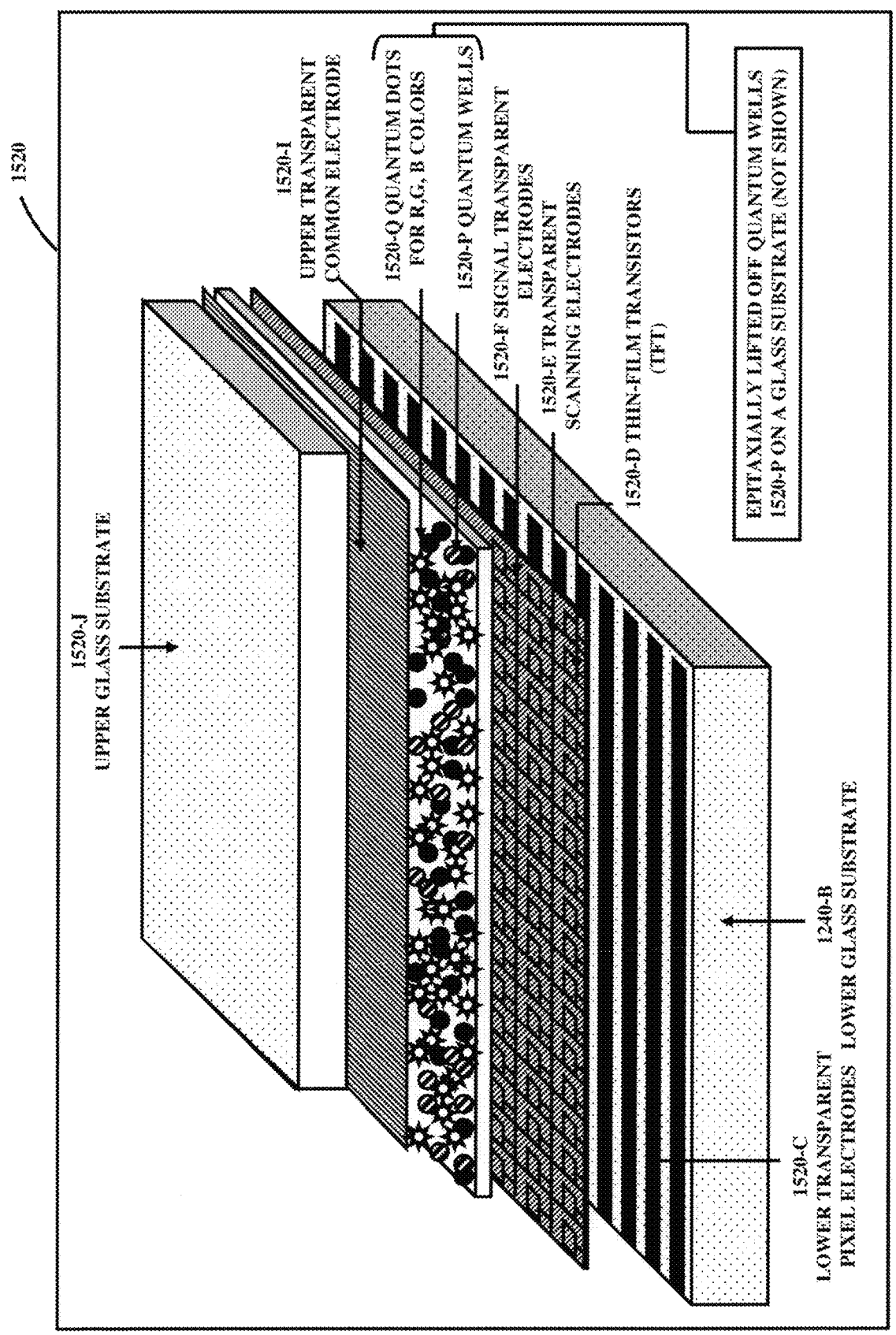
FIGS. 5E and 5F illustrate cross-sections of the display component of the mobile internet device, according to one embodiment of the present invention.

FIG. 5E illustrates a cross-section of another enabling configuration of the display component 1520 of the mobile internet device 300. Along with an array of thin-film transistors 1520-D, the critical element of this configuration is lifted semiconductor quantum-wells layers 1520-P on a glass substrate (e.g. the glass substrate 1240-B). Furthermore, the semiconductor quantum-wells layers 1520-P has both p-metal and n-metal contacts.

The semiconductor quantum-well layers 1520-P can be electrically excited by current from a battery. The released energy can be non-radiatively transferred to nanocrystal quantum dots (of various diameters/sizes) 1520-Q to produce red, green and blue light from an adjacent layer of nanocrystal quantum dots 1520-Q to enable an efficient color display component 1520.

Figure 5F:
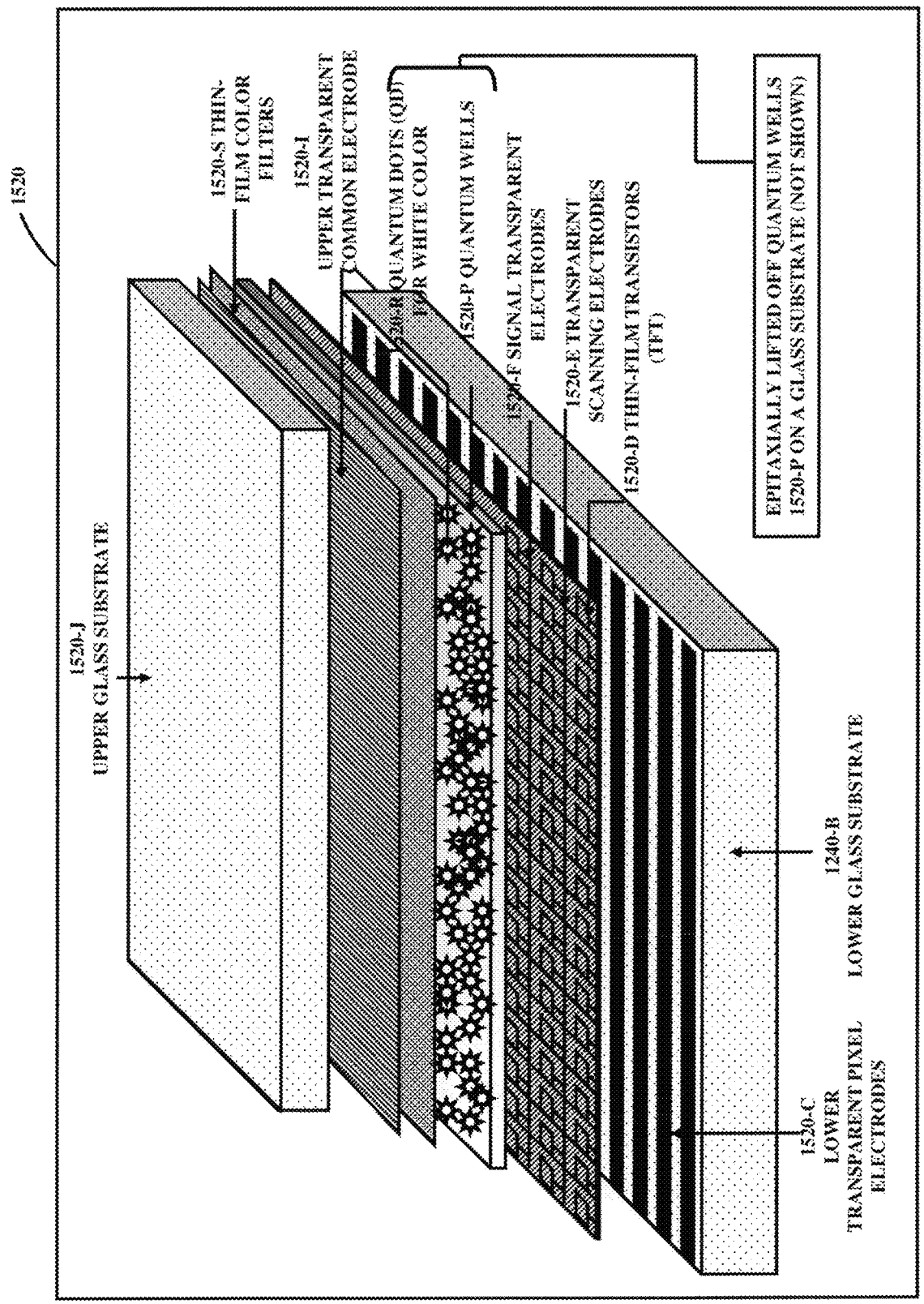

FIG. 5F illustrates a cross-section of another enabling configuration of the display component 1520 of the mobile internet device 300. Along with an array of thin-film transistors 1520-D the critical element of this configuration is epitaxially lifted semiconductor quantum-well layers 1520-P on a glass substrate (e.g., the glass substrate 1240-B). Furthermore, the semiconductor quantum-well layers 1520-P has both p-metal and n-metal contacts.

The semiconductor quantum-well layers 1520-P can be electrically excited by current from a battery. The released energy can be non-radiatively transferred to uniformly sized nanocrystal quantum dots 1520-R to produce white light emission from an adjacent layer of uniformly sized nanocrystal quantum dots 520-R. The white light can be filtered by an array of thin-film color filters 1520-S to enable an efficient color display component 1520. Details of a quantum dot display have been described/disclosed in U.S. Non-Provisional patent application Ser. No. 12/931,384 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Jan. 31, 2011 (now U.S. Pat. No. 8,548,334, issued on Oct. 1, 2013) (which claims benefit of priority to U.S. provisional application Ser. No. 61/404,504 entitled "DYNAMIC INTELLIGENT BIDIRECTIONAL OPTICAL ACCESS COMMUNICATION SYSTEM WITH OBJECT/INTELLIGENT APPLIANCE-TO-OBJECT/INTELLIGENT APPLIANCE INTERACTION", filed on Oct. 5, 2010). Details of various embodiments of the display/holographic display as the display component 1520 of the mobile wearable internet device 300 have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 (which claims benefit of priority to: U.S. Provisional Patent Application No. 62/230,249 entitled "SYSTEM AND METHOD OF AMBIENT/PERVASIVE USER/HEALTHCARE EXPERIENCE", filed on Jun. 1, 2015).

Figure 6:
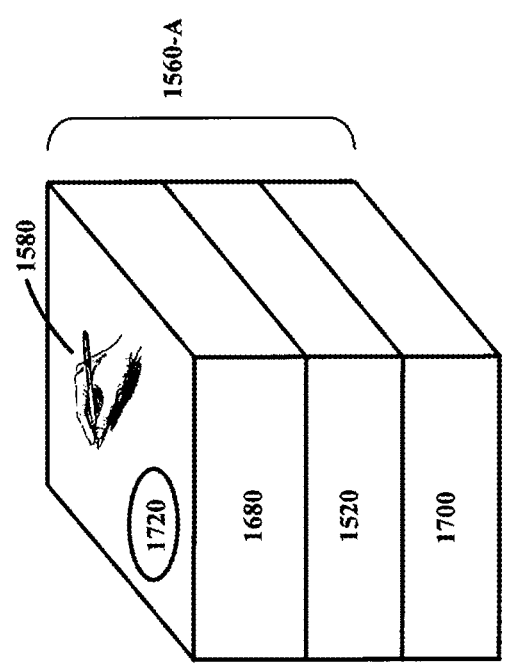
FIG. 6 illustrates a block diagram of a sketch pad electronic module, according to one embodiment of the present invention.

FIG. 6 illustrates a block diagram of the sketch pad (with write/erase options) electronic module 1560 with the stylus 1580. The sketch pad electronic module 1560 is a multilayer device, having a transparent (e.g., indium tin oxide or graphene) input matrix 1680, below the transparent input matrix 1680, there is the display component (e.g., a liquid crystal or graphene based display component) 1520 and below which there is an electronic (scan, drive and display memory) circuitry 1700. 1560-A is an integrated electronic device, excluding the stylus 1580.

The stylus 1580 can be formed in the shape of a pencil from silicon rubber impregnated with metal particles.

As the stylus 1580 writes over the transparent input matrix 1680, it can capacitively couple with the transparent input matrix 1680. Thus, if there is a change in the capacitance, the change in the capacitance can be sensed by the electronic circuitry 1700. The electronic circuitry 1700 can be electrically coupled with a switch 1720. Utilizing the switch 1720, the sketch pad electronic module 1560 can be operated in both write and erase modes.

Figure 7:
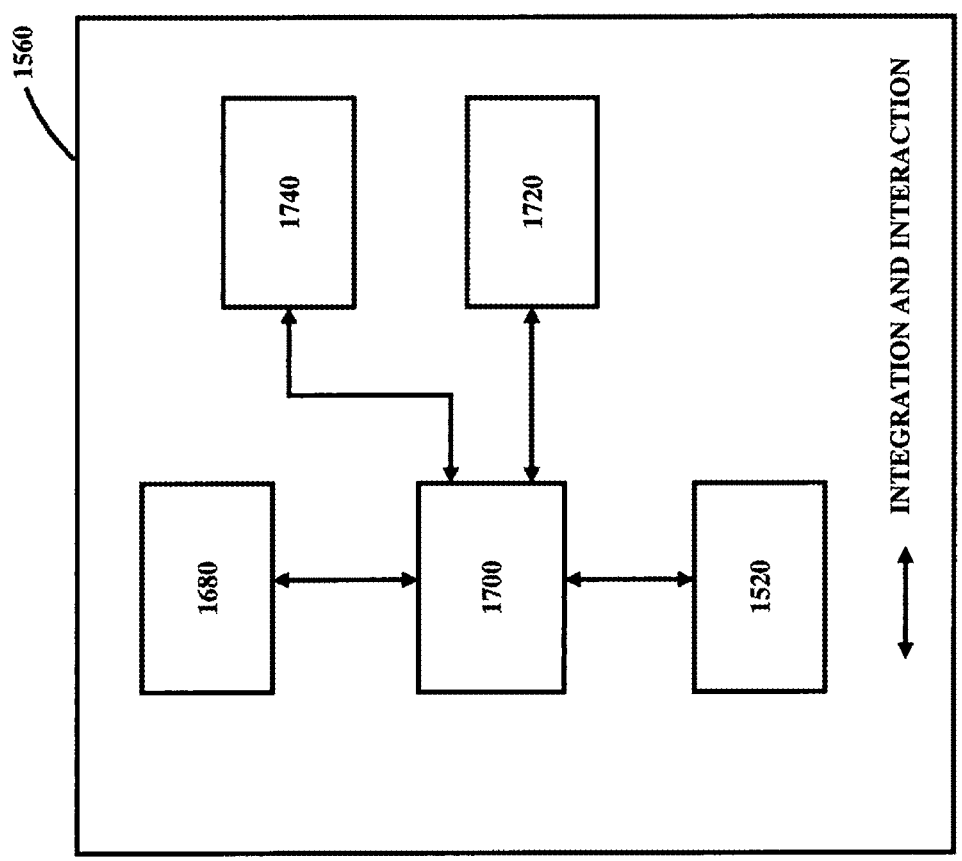
FIG. 7 illustrates a block diagram of the sketch pad electronic module, according to one embodiment of the present invention.

FIG. 7 illustrates a block diagram of the sketch pad electronic module 1560, where the electrical coupling between the transparent input matrix 1680, display component 1520, electronic circuitry 1700 and switch 1720 are described. Furthermore, a hand-writing recognition algorithm and/or a pattern recognition algorithm 1740 can enhance the performance of the sketch pad electronic module 1560.

Figure 8A:
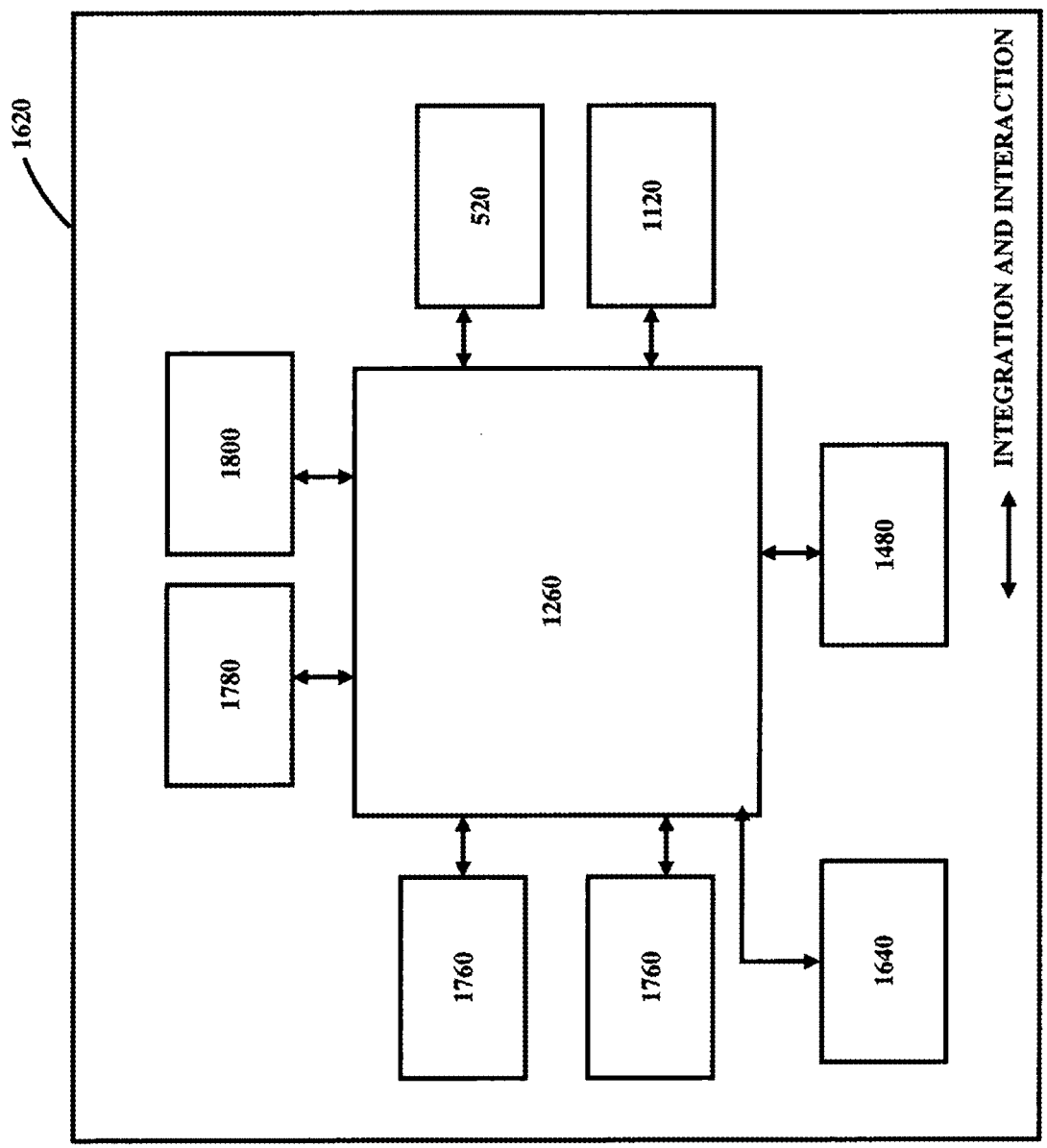
FIG. 8A illustrates a block diagram of a personal awareness assistant miniature electronic module, according to one embodiment of the present invention.

FIG. 8A illustrates a block diagram of the personal awareness assistant miniature electronic module 1620, which integrates: the storage/memory 520 (however, the storage/memory 520 can also be replaced by the general storage electronic module 520-C), the sensor 1120, the medium performance microprocessor 1260, the camera 1480, the voice-to-text-to-voice conversion algorithm 1640, two (2) microphones 1760, a scrolling audio recording buffer 1780 and a voice recognition algorithm 1800.

The personal awareness assistant miniature electronic module 1620 can be always on. It can passively listen to what the user 160 says and can respond to a particular context and situation. For example: the user 160 can hear about a product and the user 160 can create a reminder by speaking to the personal awareness assistant miniature electronic module 1620. The user 160 can transmit that information from the personal awareness assistant miniature electronic module 1620 to the social wallet 100 via the electronic social wallet electronic module 280 and/or mobile internet device 300 for further processing and/or fulfillment. After processing the information from the personal awareness assistant miniature electronic module 1620, the social wallet 100 can then deliver a real time location based coupon(s) to the mobile internet device 300, by measuring the user's 160 location information by utilizing an indoor/outdoor location measurement miniature electronic module 1440 of the mobile internet device 300.

Optionally the personal awareness assistant miniature electronic module 1620 can be a standalone miniature electronic module (but it can be plugged or integrated with the social wallet electronic module 280/mobile internet device 300).

For example, when the user 160 is introduced to someone, the personal awareness assistant miniature electronic module 1620 can automatically recognize and may take a low-resolution photo. Once the mobile internet device 300 collects information, it can automatically categorize the information into a pre-designated database with audio, digital image, time/date stamp and global positioning system location. Because the data is stored contextually, the information retrieval can be straightforward. In response to a simple voice command inquiry, such as "whom did I meet on Apr. 15, 2009 at 12 PM"?, the personal awareness assistant miniature electronic module 1620 can bring up the appropriate information about that specific person. Thus, the mobile internet appliance is context-aware.

Furthermore, the voice recognition algorithm 1800 can enhance the capability of the personal awareness assistant miniature electronic module 1620.

Additionally, a face recognition algorithm can enhance the capability of the personal awareness assistant miniature electronic module 1620.

Figure 8B:
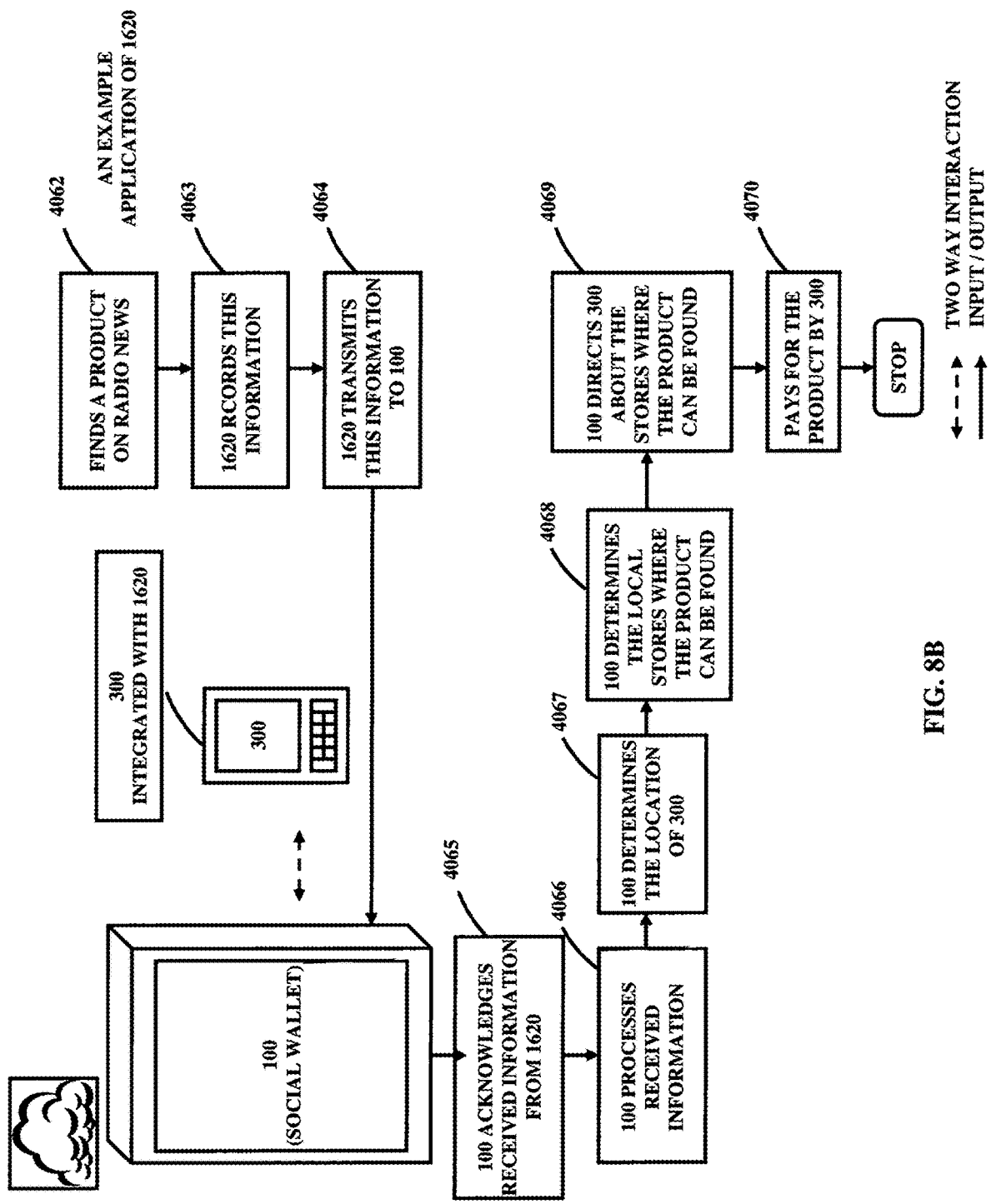
FIG. 8B illustrates an application of the personal awareness assistant miniature electronic module, according to one embodiment of the present invention.

FIG. 8B illustrates an application of the personal awareness assistant miniature electronic module 1620 of the mobile internet device 300. In step 4062, the user finds a product (e.g., on the radio news). In step 4063, the personal awareness assistant miniature electronic module 1620 records that product information with the user's consent. In step 4064, the personal awareness assistant miniature electronic module 1620 transmits the product information to the social wallet 100. In step 4065, the social wallet 100 acknowledges the received (product) information from the personal awareness assistant miniature electronic module 1620. In step 4066, the social wallet 100 processes the received (product) information from the personal awareness assistant miniature electronic module 1620. In step 4067, the social wallet 100 determines the location of the mobile internet device 300 in real time. In step 4068, the social wallet 100 determines the local stores, where the product can be found. In step 4069, the social wallet 100 directs (turn by turn) the mobile internet device 300 in real time regarding the location of a specific or closest store, where the product can be found. In step 4070, the user 160 pays for the product by the mobile internet device 300 (the mobile internet device 300 can be integrated with the social wallet electronic module 280). Furthermore, the social wallet electronic module 280 is integrated with the near-field communication miniature electronic module 620.

As the social wallet 100 can learn or relearn the user's preferences, the unified algorithm 320 can render intelligence based on the user's preferences utilizing the intelligence rendering algorithm 400 and the self-learning (including relearning) algorithm 420.

Similarly, the mobile internet device 300 can also learn or relearn the user's preferences utilizing the algorithm 1660. The algorithm 1660 includes: (a) a physical search algorithm, (b) an algorithm-as-a-service, (c) an intelligent rendering algorithm (e.g., artificial intelligence, behavior modeling, data interpretation, data mining, fuzzy logic, machine vision, natural language processing, neural network, pattern recognition and reasoning modeling) and (d) a self-learning (including relearning) algorithm. It should be noted that the self-learning (including relearning) algorithm can include a self-learning artificial intelligence algorithm and/or a self-learning neural network algorithm.

The personal awareness assistant miniature electronic module 1620 is context-aware. Thus, the mobile internet device 300 is also context-aware.

Figure 9:
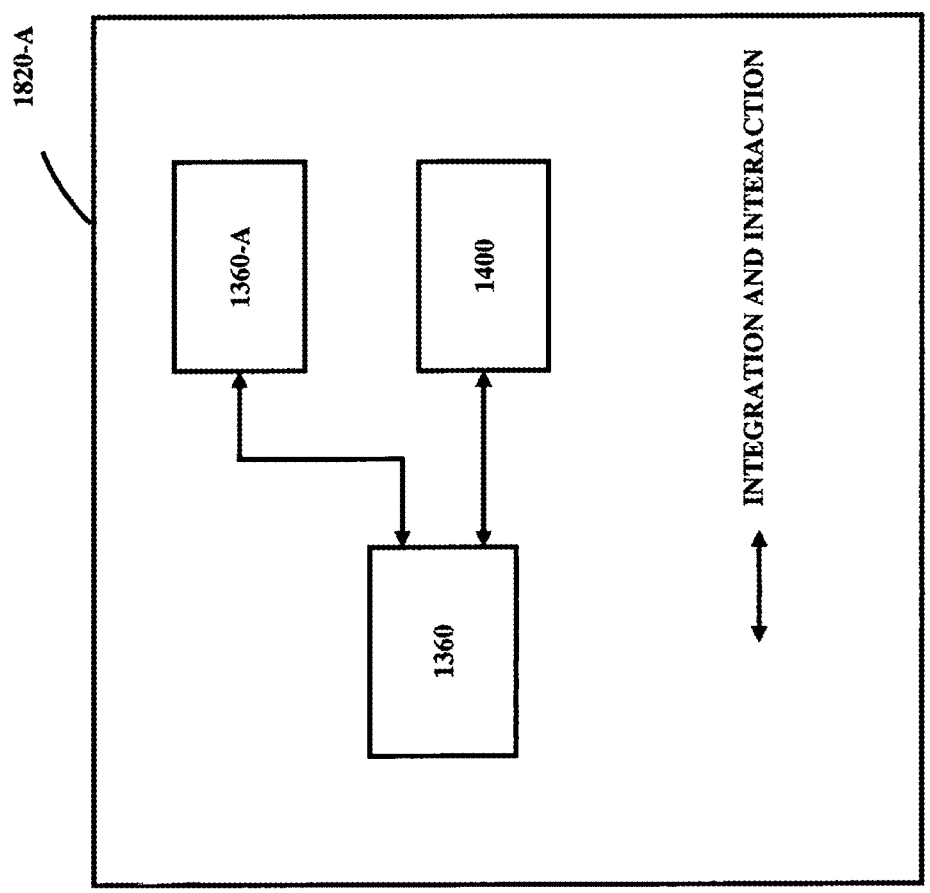
FIG. 9 illustrates a block diagram of a first system-on-chip for the mobile internet device, according to one embodiment of the present invention.

FIG. 9 illustrates a block diagram of a first system-on-chip 1820-A, integrating a microprocessor 1360, a graphics processor unit (GPU) 1360-A and an internet security algorithm 1400.

Figure 10:
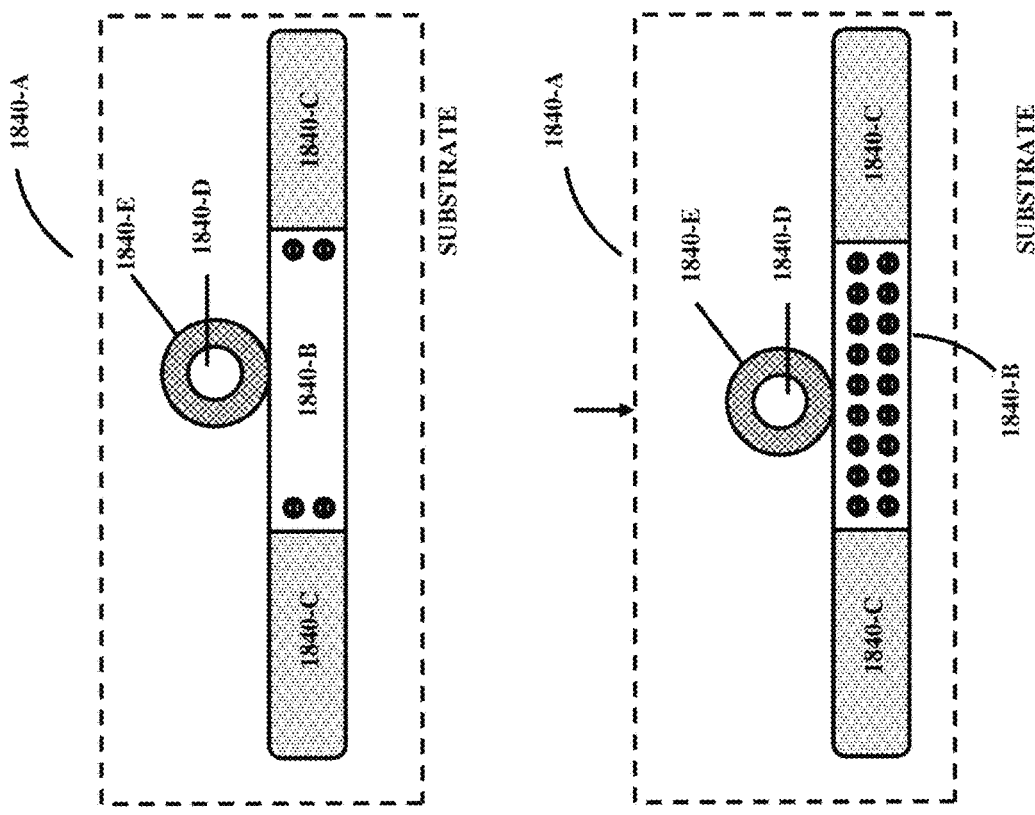
FIG. 10 illustrates a configuration of a nano-transistor, according to one embodiment of the present invention.
Figure 10:
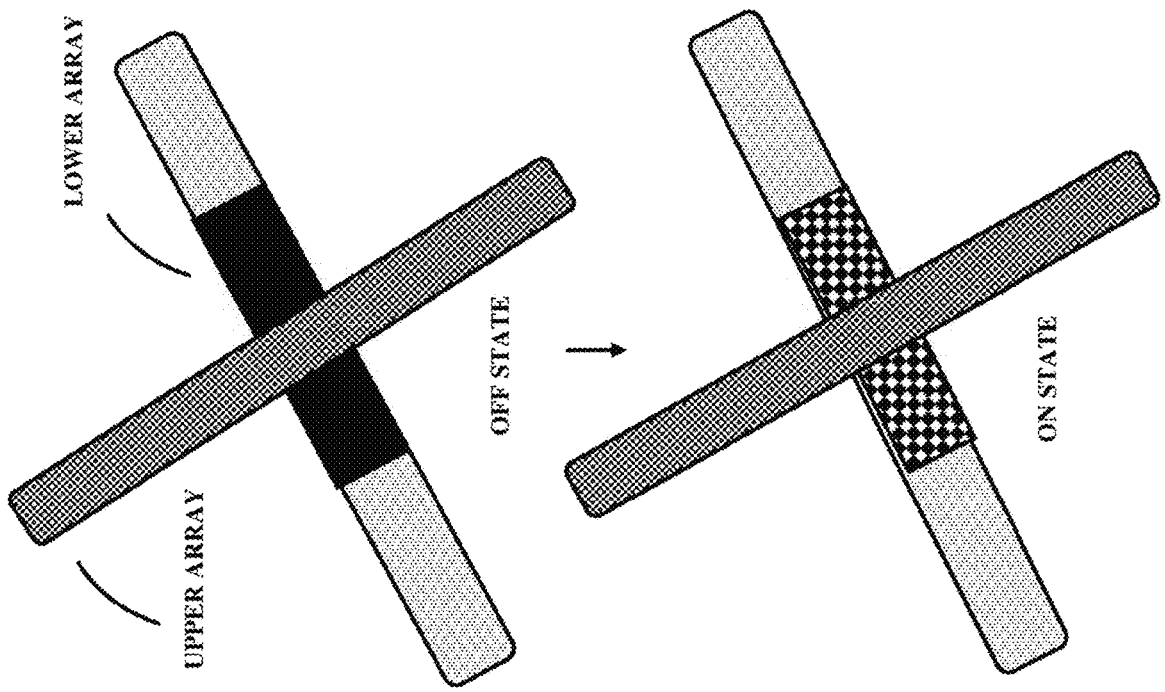

FIG. 10 illustrates a block diagram configuration of a nano-transistor 1840-A. A lower nanowire array of a switchable active material (e.g., silicon or germanium) 1840-B sandwiched between contacts (e.g., nickel silicide for silicon or nickel germanide for germanium) 1840-C can be fabricated/constructed. An upper array of gate metal 1840-D enclosed within an insulating shell 1840-E can be fabricated/constructed. Voltage applied via the gate metal 1840-D can switch the active material 1840-B from an off state to an on state.

Figure 11:
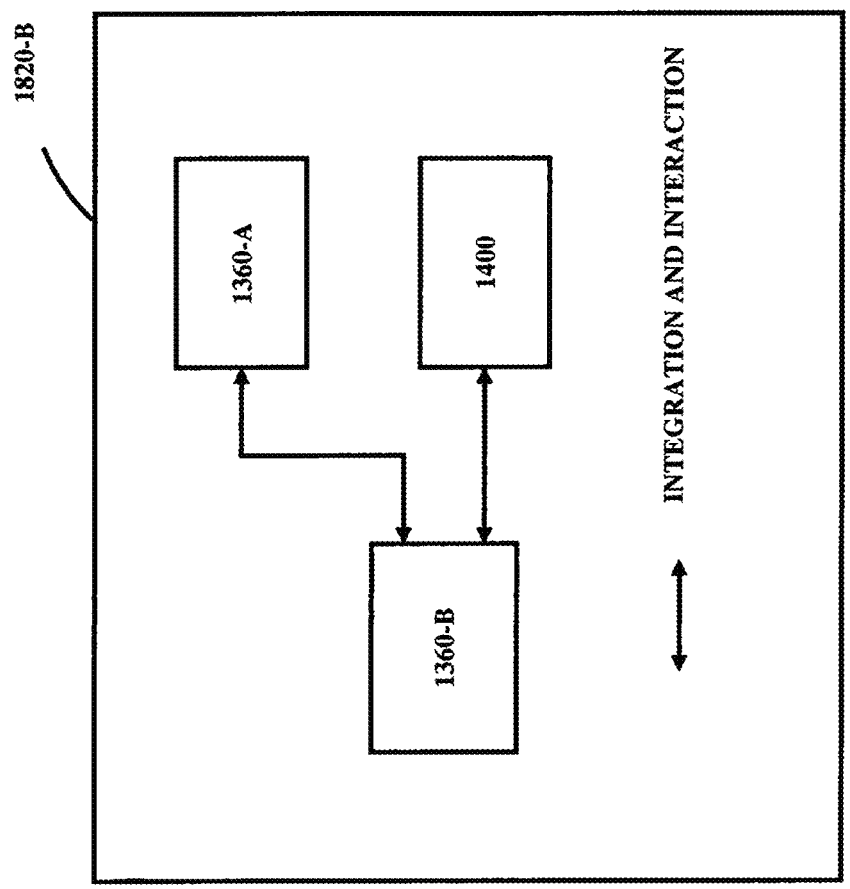
FIG. 11 illustrates a block diagram of a second system-on-chip (where a microprocessor is based on nano-transistors) for the mobile internet device, according to another embodiment of the present invention.

FIG. 11 illustrates a block diagram configuration of a second system-on-chip 1820-B, which integrates a microprocessor 1360-B, (where the microprocessor 1360-B is based on nano-transistors 1840-A), the graphics processor unit 1360-A and the internet security algorithm 1400.

Molybdenite ($MoS_2$) is a two-dimensional crystal with a natural bandgap. It is suitable for production of digital integrated circuits. A reduction in bandgap and/or increase in mobility of molybdenite can be achieved by an addition of lithium (Li) ions.

Graphene is also a two-dimensional crystal with a higher carrier mobility, as well as lower noise. It has the ideal properties to be an excellent component of integrated circuits. Graphene epitaxially grown on silicon carbide (SiC) may be suitable for production of integrated circuits.

A graphene variant called graphane has hydrogen atoms attached to the carbon lattice in insulating layers.

Graphyne is a one-atom-thick sheet of carbon that resembles graphene, except in its two-dimensional framework of atomic bonds, which contains triple bonds in addition to double bonds. Graphyne has a graphene-like electronic structure resulting in effectively massless electrons due to Dirac Cones. All electrons are travelling at roughly the same speed (about 0.3% of the speed of light). This uniformity leads to conductivity greater than copper. Graphyne has a capability of self-modulating its electronic properties, which means that it could be used as a semiconductor practically as-is, without requiring any non-carbon dopant atoms to be added as a source of electrons, as non-carbon dopants may be required for graphene. Furthermore, graphyne crystal structure allows electrons to flow in just one direction.

A first lower parallel array of nanoscaled metal (platinum) wires can be fabricated/constructed onto a substrate. A titanium oxide-titanium dioxide thin film can be deposited on the first lower parallel array of nanoscaled metal wires. A second upper parallel array of nanoscaled metal (platinum) wires can be fabricated/constructed on top of the titanium oxide-titanium dioxide thin film. The second upper parallel array is typically fabricated/constructed perpendicular to the first lower parallel array.

A memristor of a titanium oxide-titanium dioxide oxide junction, can be formed when the first lower parallel array of nanoscaled metal (platinum) wires cross the second upper parallel array of nanoscaled metal (platinum) wires. A memristor is less than 50 microns×50 microns in size. A memristor is a two-terminal nanoscaled non-linear passive switching element, whose resistance changes depending on the amount, direction and duration of voltage applied on it. But whatever its past state or resistance was, it freezes at that state, until another voltage is applied to change it. It has a variable resistance and can retain the resistance even when the electrical power is switched off. It is similar to a transistor, used to store data in a flash memory. Since a memristor is a two-terminal microscaled/nanoscaled passive switching element, it can be built on top of transistors to electrically power it up.

Phase-change memory (e.g., germanium-antimony-tellurium) has been used in optical information technologies (e.g., a DVD) and non-volatile memory applications. Furthermore, a phase-change memory material based switching element can be used instead of a memristor. The phase-change memory material based switching element exploits a unique switching behavior of a phase-change material between amorphous (high resistivity) and crystalline (low resistivity) material states with the application of electrical pulses by titanium nitride top electrode and titanium nitride-tungsten bottom electrode to generate the required joule heating for the phase transformation.

Furthermore, a dense local network of switching elements 1840s (e.g., based on memristors and/or phase-change memory material based switching elements) can be monolithically integrated with transistors fabricated/constructed on a semiconductor (e.g., silicon or germanium or silicon-germanium) and/or nano-transistors fabricated/constructed on a semiconductor (e.g., silicon or germanium or silicon-germanium) and/or transistors fabricated/constructed on two-dimensional crystal.

Figure 12:
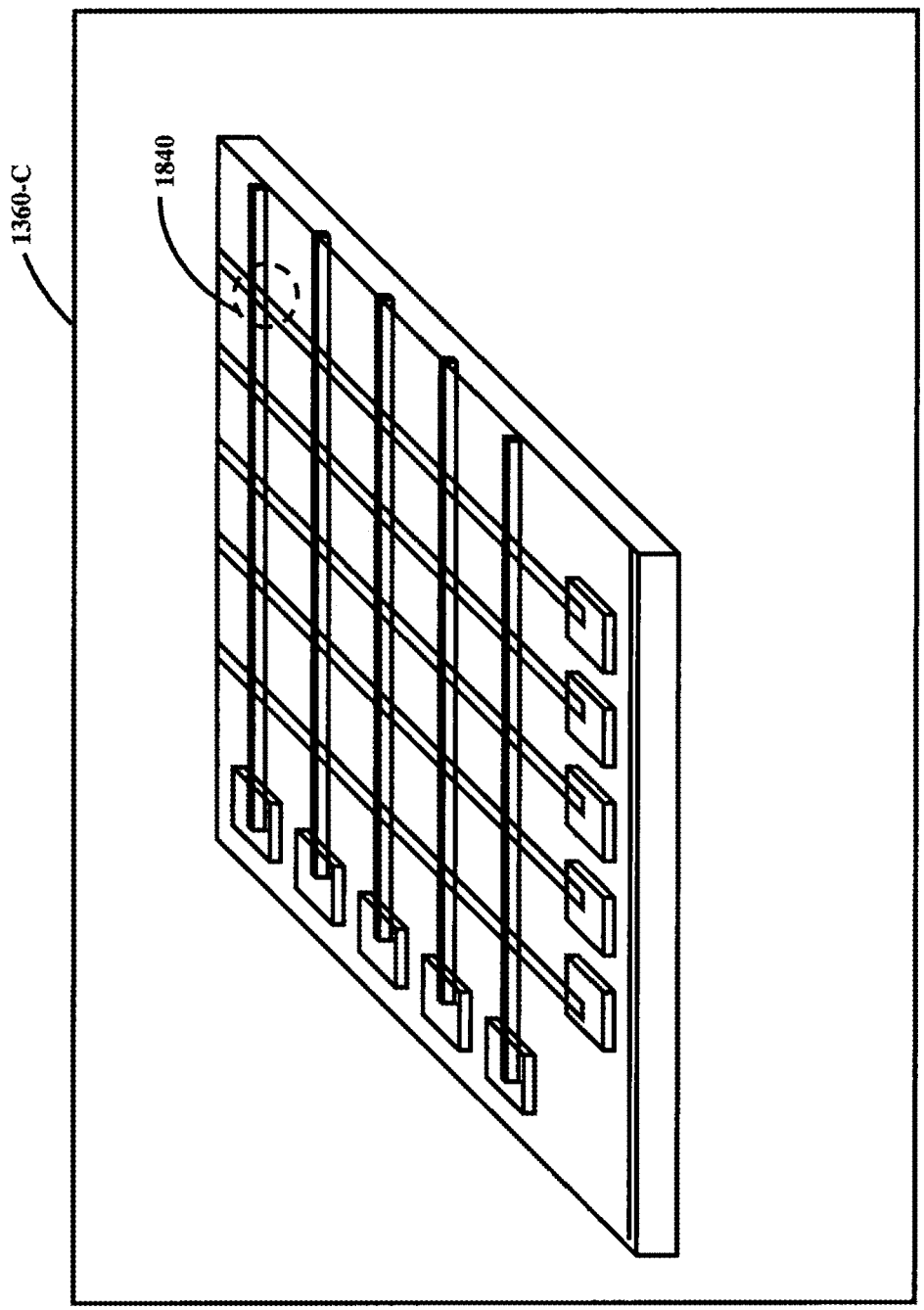
FIG. 12 illustrates a block diagram configuration of a memristor (or a phase change material based switching element), according to one embodiment of the present invention.

FIG. 12 illustrates the switching element 1840 based on the memristor and/or phase-change memory material.

Thus, transistors (fabricated/constructed on a semiconductor and/or two-dimensional crystal) with integrated switching elements 1840 can be utilized to fabricate/construct a reconfigurable (and with lower electrical power consumption) advanced microprocessor 1360-C.

Figure 13:
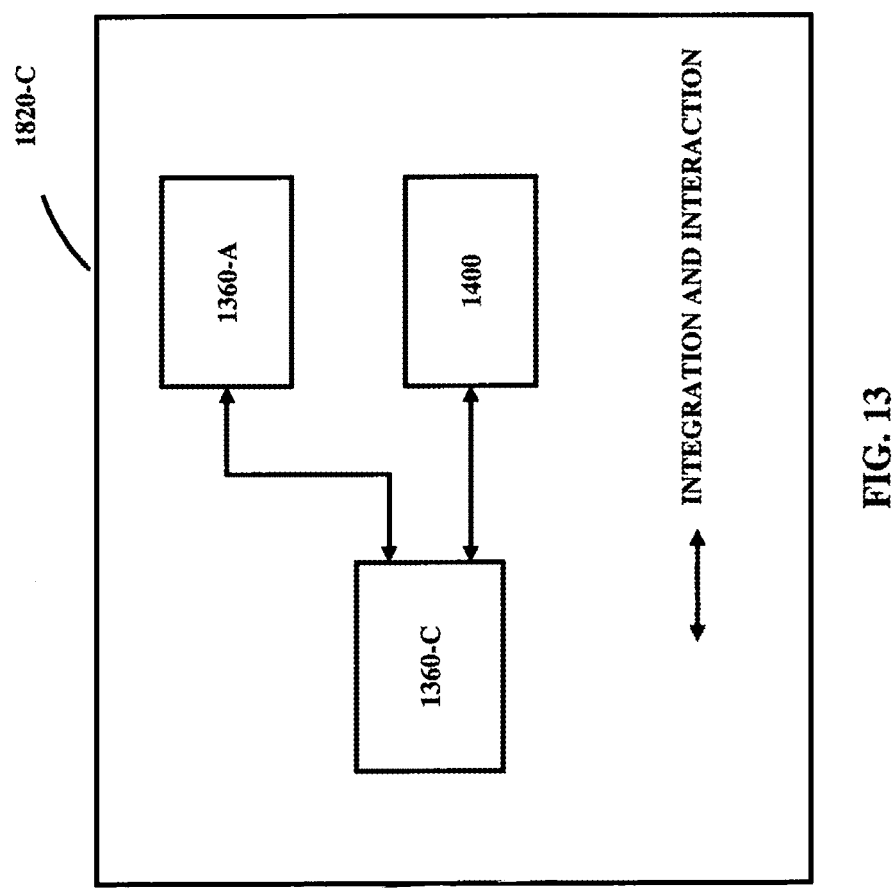
FIG. 13 illustrates a block diagram of a third system-on-chip, (where a microprocessor is based on memristors (or phase change material based switching elements)) for the mobile internet device, according to another embodiment of the present invention.

FIG. 13 illustrates a block diagram configuration of a third system-on-chip 1820-C, which integrates an advanced microprocessor 1360-C, the graphics processor unit 1360-A and the internet security algorithm 1400.

In a human brain, neurons are connected to each other through programmable junctions called synapses. The synaptic weight modulates how signals are transmitted between neurons and can in turn be precisely adjusted by an ionic flow through the synapse.

The switching element 1840 is a non-linear resistive device with an inherent memory and similar to a synapse. It is a two-terminal device whose conductance can be modulated by an external stimulus with the ability to store (memorize) the new information. The switching element 1840 can bring data close to computation without a lot of electrical power consumption, as a biological neural system does.

Figure 14:
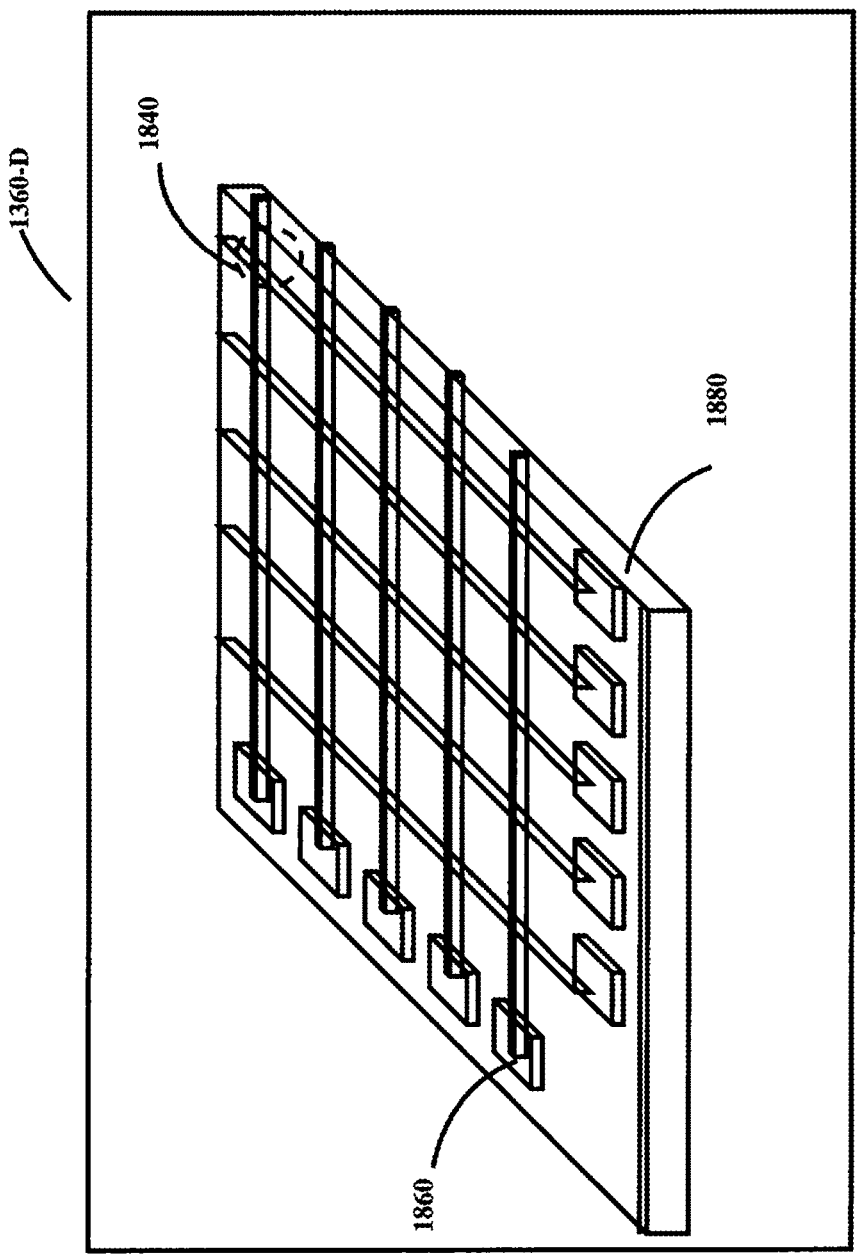
FIG. 14 illustrates a block diagram configuration of a memristor (or a phase change material based switching element) with pre-neurons and post-neurons.

FIG. 14 illustrates an embodiment of a neural network microprocessor 1360-D. 1360-D integrates the switching element 1840 based synapses, complementary metal-oxide semiconductor (CMOS) pre-neurons 1860 (fabricated/constructed on a semiconductor and/or two-dimensional crystal) and complementary metal-oxide semiconductor post-neurons 1880 (fabricated/constructed on a semiconductor and/or two-dimensional crystal).

Figure 15:
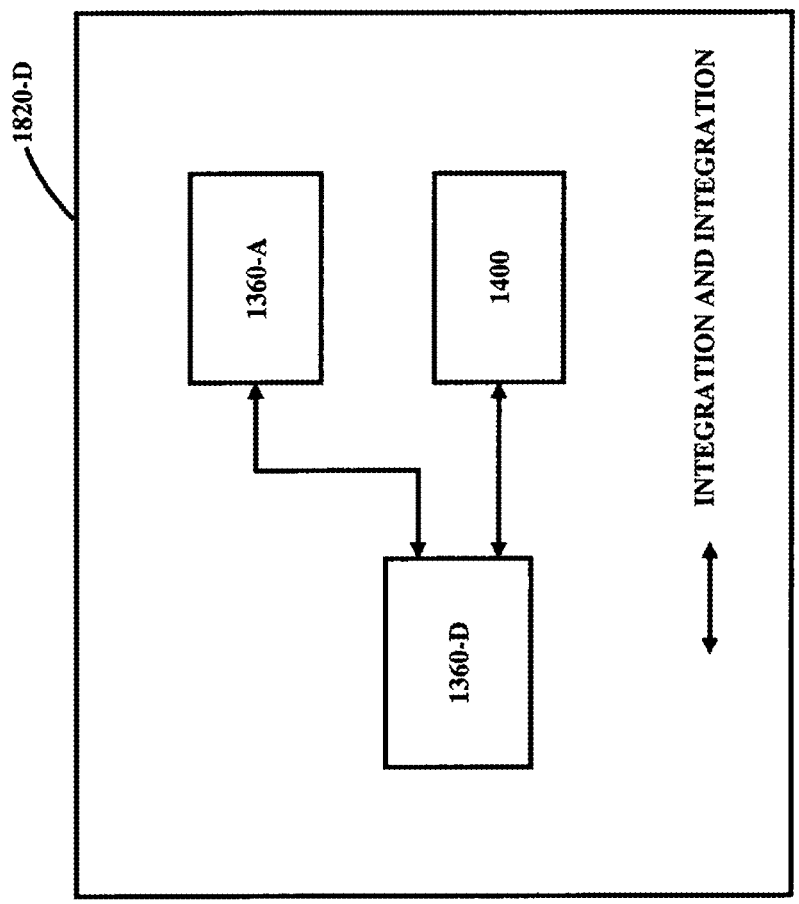
FIG. 15 illustrates a block diagram of a fourth system-on-chip (where a microprocessor is based on a neural network) for the mobile internet device, according to another embodiment of the present invention.

FIG. 15 illustrates a block diagram configuration of a fourth system-on-chip 1820-D, which integrates an advanced microprocessor (based on a neural network) 1360-D, the graphics processor unit 1360-A and the internet security algorithm 1400.

Figure 16:
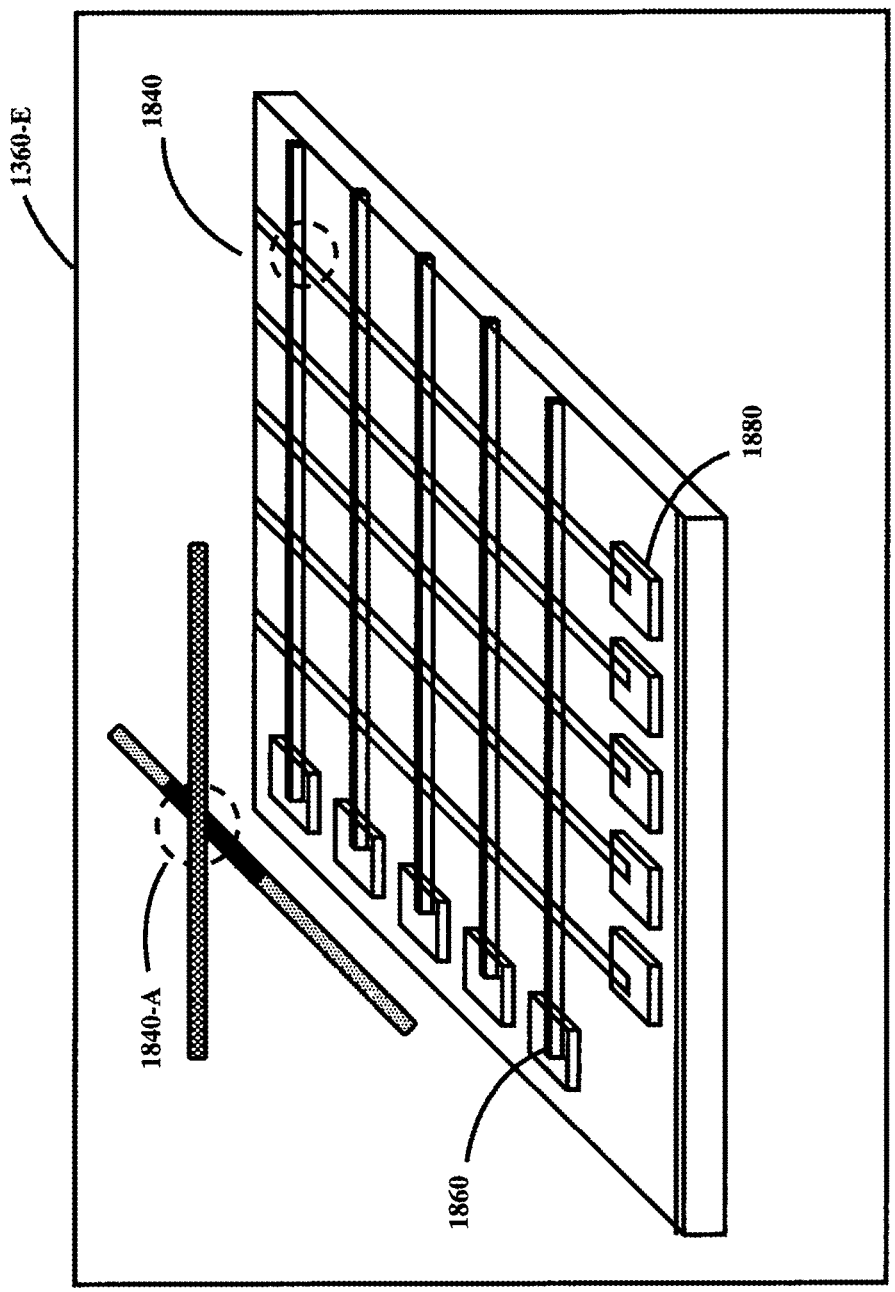
FIG. 16 illustrates a block diagram configuration of the memristors (or the phase change material based switching elements) with pre-neurons, post-neurons and nano-transistors, according to one embodiment of the present invention.

FIG. 16 illustrates another embodiment of an advanced microprocessor 1360-E (based on a neural network and nano-transistors 1840-A). 1360-E integrates the switching element 1840 based synapses, complementary metal-oxide semiconductor pre-neurons 1860 (fabricated/constructed on a semiconductor and/or two-dimensional crystal), complementary metal-oxide semiconductor post-neurons 1880 (fabricated/constructed on a semiconductor and/or two-dimensional crystal) and nano-transistors 1840-A.

Figure 17:
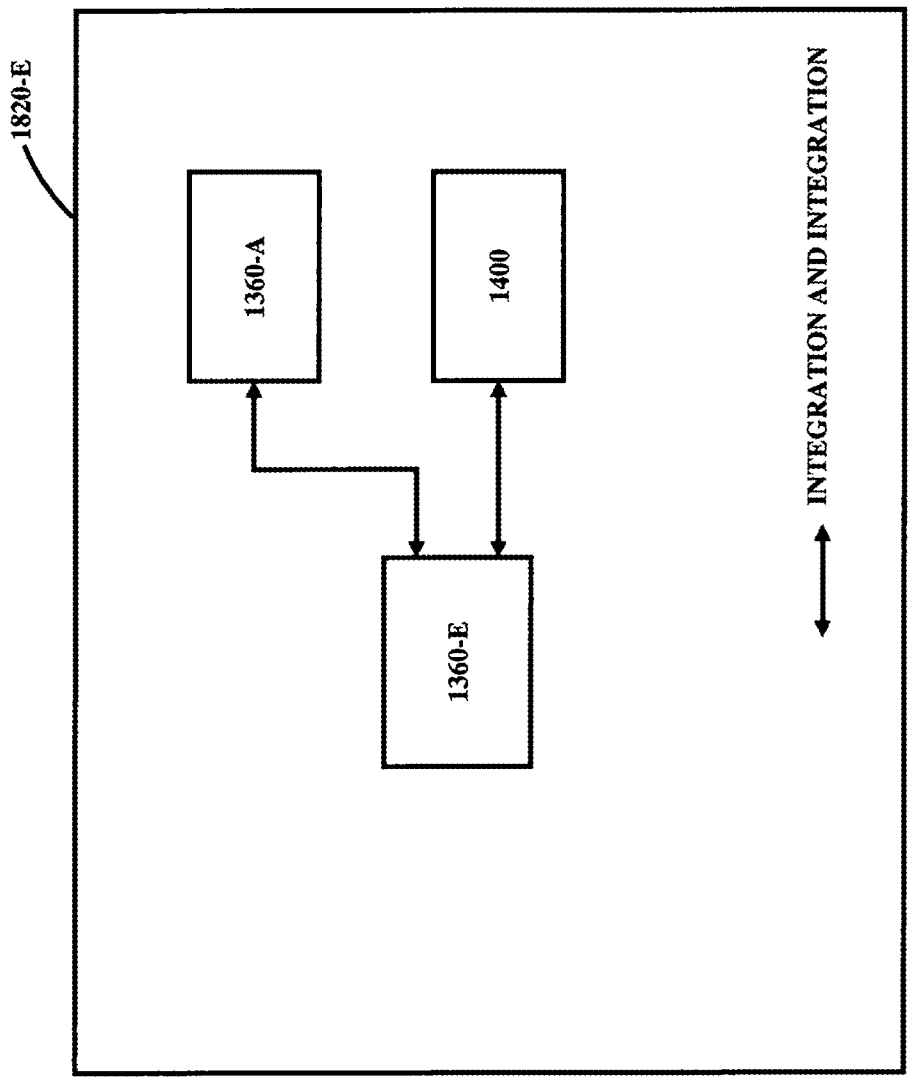
FIG. 17 illustrates a block diagram of a fifth system-on-chip (where a microprocessor is based on the neural network and nano-transistors) for the mobile internet device, according to another embodiment of the present invention.

FIG. 17 illustrates a block diagram configuration of a fifth system-on-chip 1820-E, which integrates an advanced microprocessor (based on a neural network and nano-transistors 1840-A) 1360-E, the graphics processor unit 1360-A and the internet security algorithm 1400.

A quantum dot memory (e.g., an array of silicon/silicon-germanium quantum dots embedded in epitaxial rare-earth oxide gadolinium oxide ($Gd_2O_3$) grown on a silicon substrate of (111) crystal orientation) can be fabricated/constructed with the system-on-chip 1820-A/B/C/D/E.

Additionally, a cross-point memory can be fabricated/constructed in multiple layers to form three-dimensionally. The three-dimensional cross-point memory can be fabricated/constructed directly on top of the system-on-chip 1820-A/B/C/D/E. Furthermore, the optical interconnect (optical layers) can also be integrated with the system-on-chip 1820-A/B/C/D/E. Details on memristors and an optical interconnect have been described/disclosed in U.S. Non-Provisional patent application Ser. No. 14/999,601 entitled "SYSTEM AND METHOD OF AMBIENT/PERVASIVE USER/HEALTHCARE EXPERIENCE", filed on Jun. 1, 2016 (which claims benefit of priority to: U.S. Provisional Patent Application No. 62/230,249 entitled "SYSTEM AND METHOD OF AMBIENT/PERVASIVE USER/HEALTH-CARE EXPERIENCE", filed on Jun. 1, 2015).

The system-on-chips 1820-A/B/C/D/Es, optically interconnected can enable the learning (relearning) computer to store and process massive datasets. Furthermore, the system-on-chips 1820-A/B/C/D/Es, optically interconnected and a neural network based algorithm(s) can enable for supervised, unsupervised and semi-supervised learning. The advanced microprocessors 1360-D and 1360-E can have Cog Ex machines/Machine OS, as an operating algorithm/system.

Figure 18A:
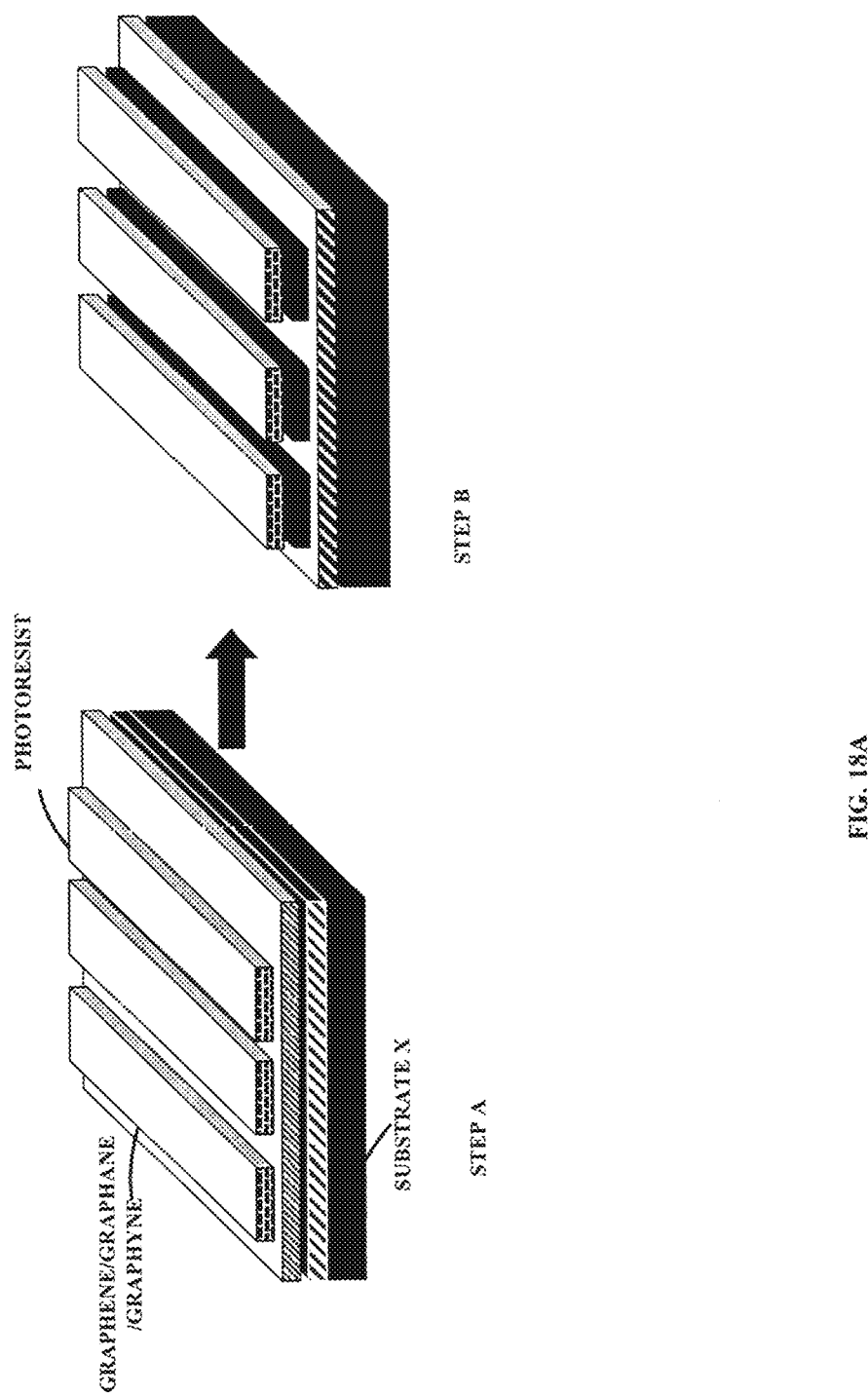
FIGS. 18 (A, B and C) illustrates process steps for integrating one or two two-dimensional crystals on a semiconductor substrate, according to one embodiment of the present invention.
Figure 18C:
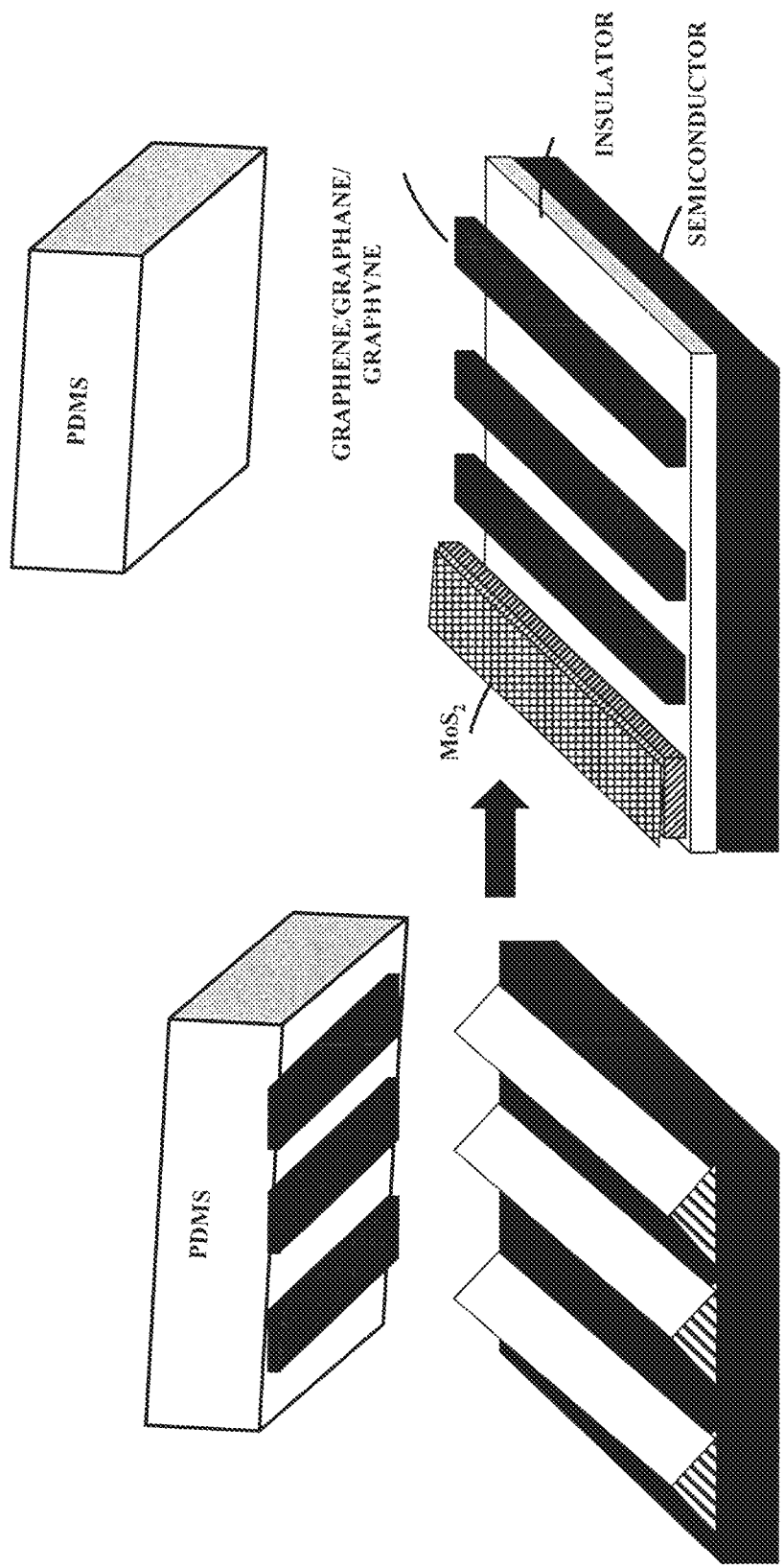

FIGS. 18 (A, B and C) illustrates a block diagram of process flow for integrating two (2) two-dimensional crystals on an insulator on a semiconductor substrate (e.g., silicon or germanium or silicon-germanium). Graphene/graphane/graphyne is grown on a substrate X (e.g., graphene can be epitaxially grown on silicon carbide substrate).

Graphene/graphane/graphyne can be patterned with a photoresist and reactive ion beam (RIE) etching. Graphene/graphane/graphyne can be bonded and detached by poly (dimethylsiloxane) (PDMS) onto an insulator on a semiconductor substrate. Thus, the above semiconductor fabrication process/method enables integration of one or two two-dimensional crystals on an insulator on a semiconductor substrate for further circuit fabrication.

For efficient thermal management of the system-on-chip 1820-A/B/C/D/E for the mobile internet device 300, thermal resistance must be minimized at all material interfaces and materials with closely matching thermal expansion coefficients must be used.

Figure 19:
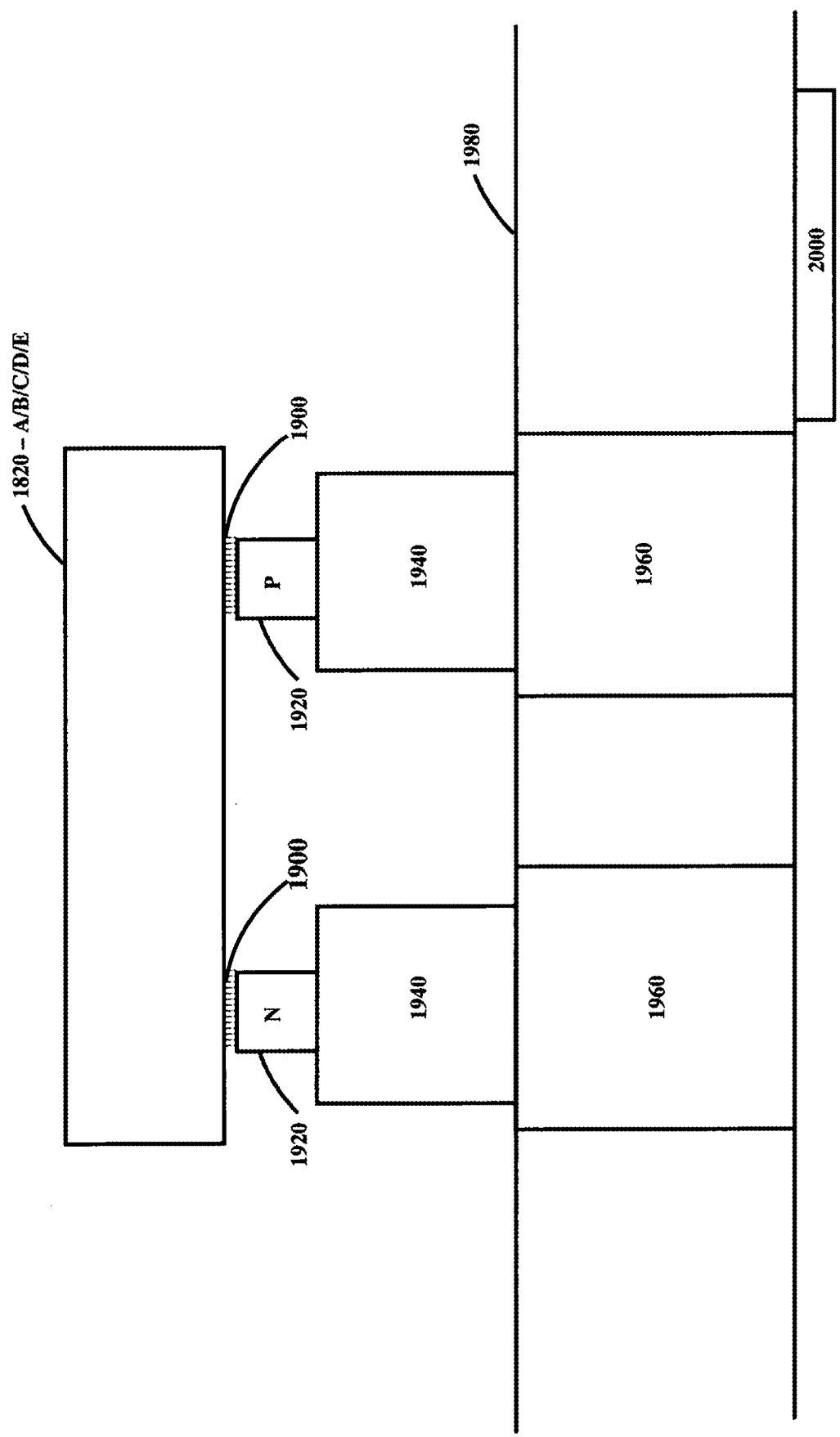
FIG. 19 illustrates a block diagram for attaching the above system-on-chip on a printed circuit board, according to one embodiment of the present invention.

FIG. 19 illustrates that the circuit side of the system-on-chip 1820-A/B/C/D/E can be flip-attached or flip-bonded on an array of thermoelectric films (both n-type and p-type) 1920s with a built-in nano-structured surface 1900 for active cooling.

About ten times (10×) heat transfer can be realized by creating a nano-structured surface (e.g., zinc oxide/graphene nano-structured surface) 1900 on the thermoelectric film 1920. However, significant thermoelectric efficiency can be gained by fabricating a quantum wire/quantum dot based thermoelectric film 1920, transitioning from a two-dimensional superlattice.

Furthermore, the thermoelectric film can be attached or bonded on a thermal pillar (e.g., copper material) 1940. The thermal pillar 1940 is about 250 microns in diameter and 50 microns in height. The thermal pillar (e.g., copper material) 1940 can be attached or bonded on a thermal via 1960 on a printed circuit board 1980 with a cooling module 2000.

Figure 20A:
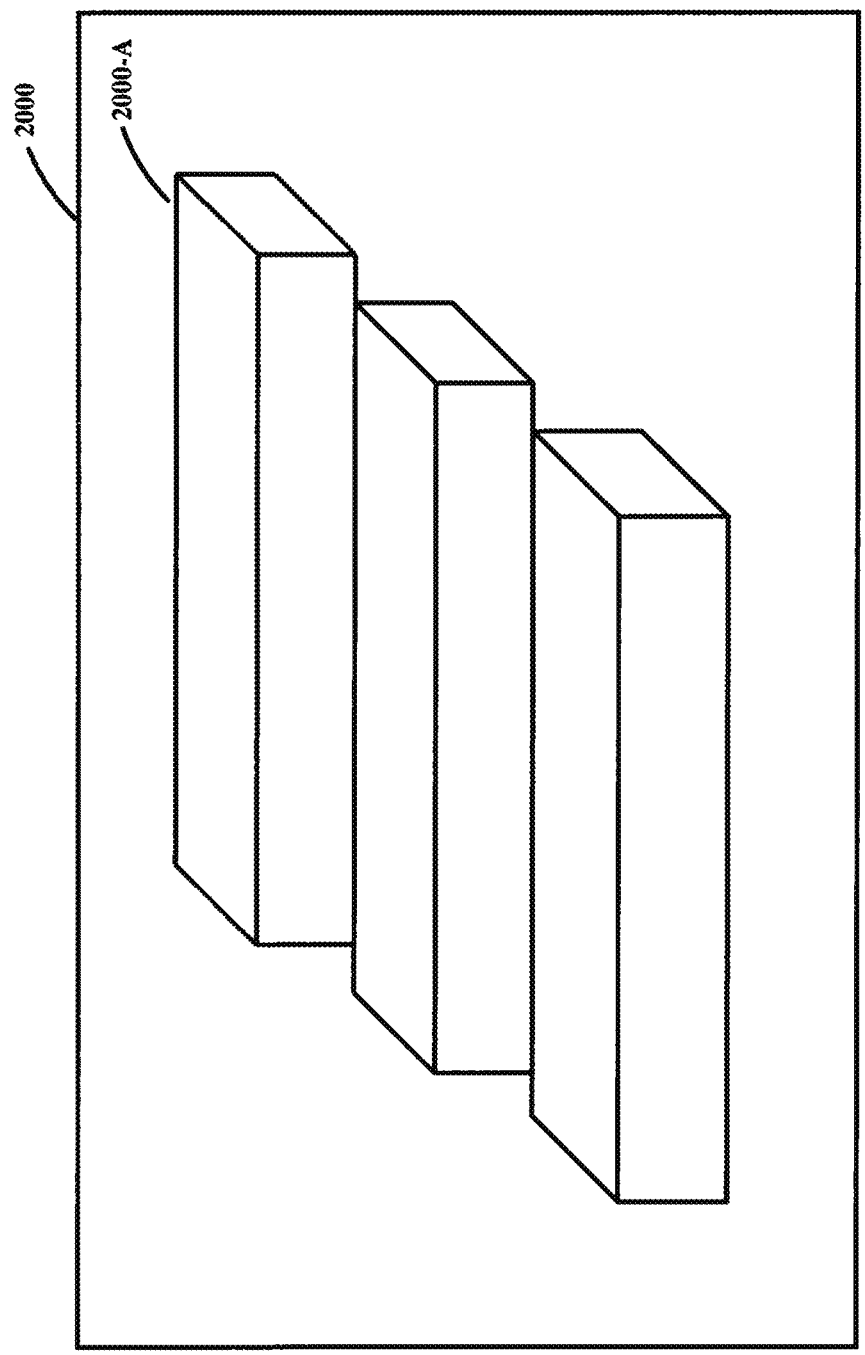
FIGS. 20 (A, B and C) illustrates a block diagram of a cooling module for the above system-on-chip on the printed circuit board, according to one embodiment of the present invention.

FIG. 20A illustrates the cooling module 2000, which can be attached or bonded with the printed circuit board 1980 to disperse the heat from the system-on-chip 1820-A/B/C/D/E. The cooling module 2000 consists of an array of mini cooling modules 2000-As.

Figure 20B:
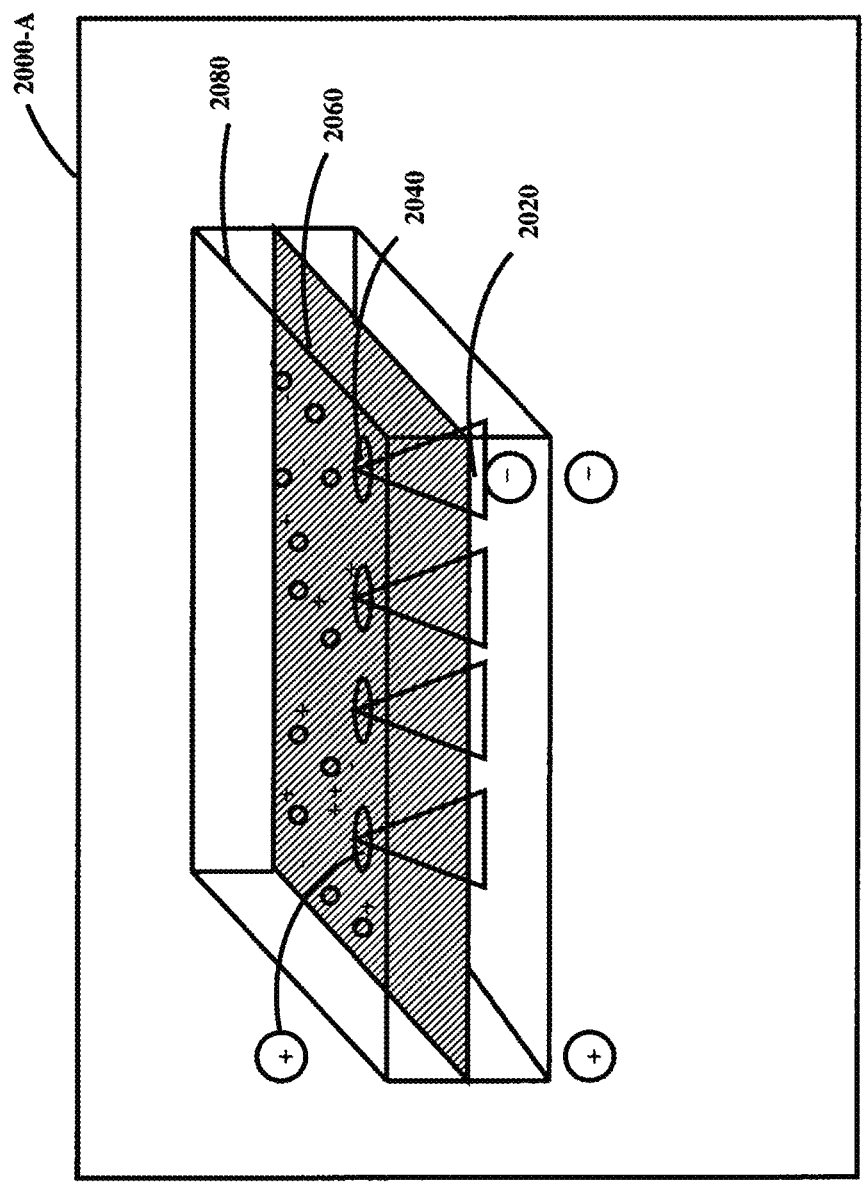

FIG. 20B illustrates the mini cooling module 2000-A. The mini cooling module 2000-A has an array of negative voltage biased tips (e.g., tips fabricated/constructed from boron nanotube/carbon nanotube/amorphous diamond/tungsten) 2020s, which is placed just below a hole (e.g., about 100 microns in diameter) 2040 of positive voltage biased surface (e.g., tungsten/two-dimensional crystal material (e.g., graphene)) 2060. Electrons emitted from the negative voltage biased array of tips 2020s can escape through the hole 2040 and ionize the gas molecules within the boundaries of a heat sink (e.g., the heat sink can be fabricated/constructed from materials such as aluminum/silicon/copper/carbon nanotube-copper composite/two-dimensional crystal material (e.g., graphene)/diamond) 2080. By switching the voltage polarity of the heat sink 2080, a moving ionized gas cloud can disperse the heat from the printed circuit board 1980.

However, it is desirable that an array of tips 2020s emits electrons at a much lower voltage (e.g., 10 volts).

FIG. 20C illustrates an array of nano-sized tungsten tips 2020s, which can be fabricated/constructed on tungsten substrate 2040-A. The tungsten tips 2020s can be surrounded by an insulator 2040-B. The nano-sized tungsten tip 2020 can be decorated with a monolayer of material 2020-A (e.g., diamond deposited by low temperature electron cyclotron resonance-chemical vapor deposition (ECR-CVD) or gold deposited by RF magnetron sputtering) to enable electrons to emit at a much lower voltage (e.g., at 10 volts) through the hole 2040, where the hole 2040 can be fabricated/constructed from a tungsten material.

To achieve faster connectivity between the system-on-chip 1820-A/B/C/D/E, an optical interconnection is preferable to an electrical interconnection.

FIG. 21A illustrates a block diagram of an interconnection between the system-on-chip 820-A/B/C/D/E (via optics) on the printed circuit board 1980.

The Table-5 below describes subcomponents required to fabricate/construct the interconnection between the system-on-chip 1820-A/B/C/D/E (via optics) on the printed circuit board 1980.

TABLE 5

| FIG. 21A Legend | Description |
| --- | --- |
| 1820-A/B/C/D/E | System-On-Chip |
| 2100 | Complementary Metal-Oxide Semiconductor Serializer |
| 2120 | Complementary Metal-Oxide Semiconductor Driver |
| 2140 | Directly Modulated Vertical Cavity Laser |
| 2140-A | Vertical Cavity Laser Integrated With Electro-Optical Modulator |
| 2160 | Two-Dimensional Photonic Crystal Wavelength Division Multiplexer On Silicon-On-Insulator (SOI) |
| 2180 | Silicon-On-Insulator Waveguide |
| 2200 | Reconfigurable Optical Switch On Silicon-On-Insulator |
| 2220 | Silicon-On-Insulator Two-Dimensional Photonic Crystal Wavelength Division Demultiplexer |
| 2240 | Photodetector |
| 2260 | Complementary Metal-Oxide Semiconductor Amplifier |
| 2280 | Complementary Metal-Oxide Semiconductor Deserializer |
| 1820-A/B/C/D/E | System-On-Chip |

Electrical outputs from the system-on-chip (e.g., 1820-A/B/C/D/E) are serialized by a complementary metal-oxide semiconductor serializer 2100. The outputs of a complementary metal-oxide semiconductor serializer 2100 can be utilized as inputs to an array of complementary metal-oxide semiconductor drivers 2120s. Correspondingly, the array of complementary metal-oxide semiconductor drivers 2120s can activate an array of directly modulated (in intensity) vertical cavity surface emitting lasers 2140s or an array of vertical cavity surface emitting lasers, which are monolithically integrated with electro-optic modulators 2140-As.

The modulated wavelengths of the directly modulated vertical cavity surface emitting lasers 2140s or vertical cavity surface emitting lasers with monolithically integrated with electro-optic modulator 2140-As can be combined on wavelengths (or colors) by a silicon-on-insulator two-dimensional photonic crystal wavelength division multiplexer 2160.

The wavelengths can be propagated by a silicon-on-insulator waveguide 2180 and if necessary, can be reconfigured by a reconfigurable optical switch 2200 on silicon-on-insulator.

The outputs of the silicon-on-insulator waveguide 2180 or reconfigurable optical switch 2200 on silicon-on-insulator can be decombined on wavelengths by a silicon-on-insulator two-dimensional photonic crystal wavelength division demultiplexer 2220.

Furthermore, the wavelengths outputs (of the silicon-on-insulator two-dimensional photonic crystal wavelength division demultiplexer 2220) can be received by an array of photodetectors (e.g., P-i-N photodetectors) 2240s, an array of complementary metal-oxide semiconductor amplifiers 2260s, then as electrical inputs to a complementary metal-oxide semiconductor deserializer 2280 and finally as electrical inputs to another system-on-chip (e.g., 1820-A/B/C/D/E).

Figure 21B:
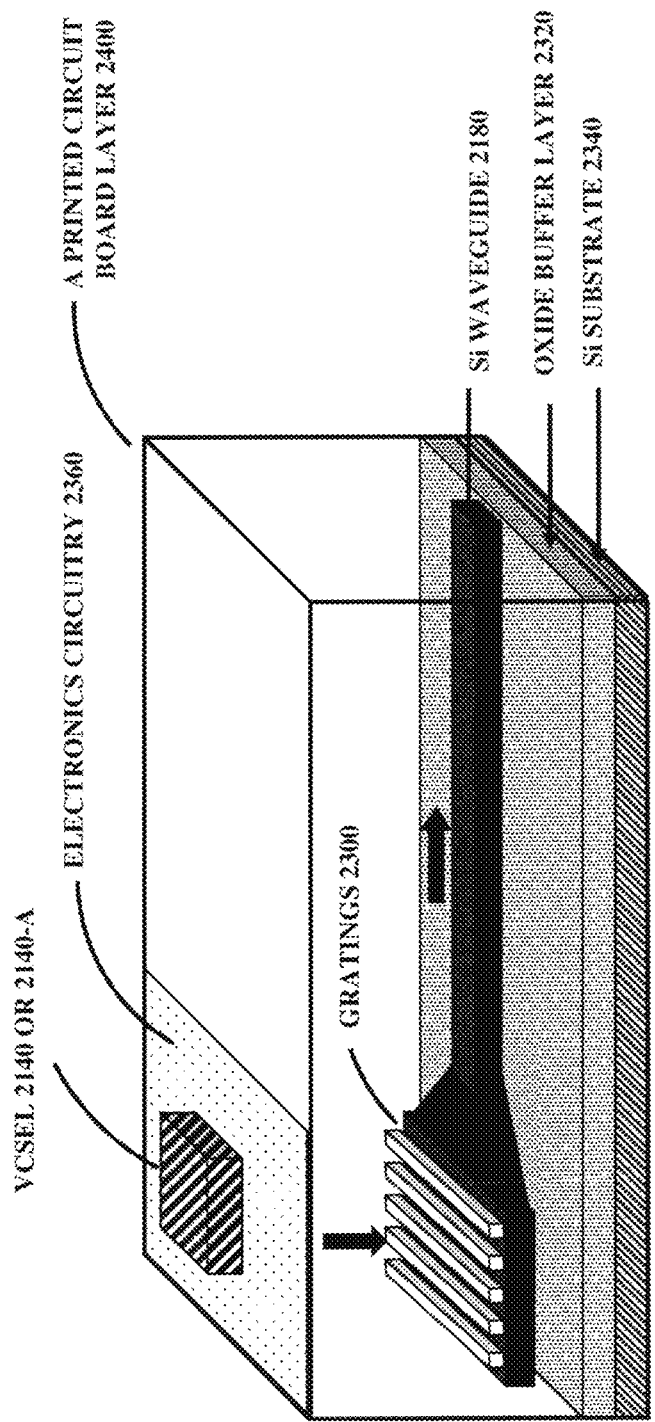
FIGS. 21 (A, B and C) illustrates a block diagram of an interconnection between the above system-on-chips (via wavelength division multiplexing) on the printed circuit board, according to one embodiment of the present invention.
FIG. 21D illustrates a cross section of a vertical cavity surface emitting laser, monolithically integrated with a modulator, according to one embodiment of the present invention.

FIG. 21B illustrates details of the silicon-on-insulator waveguide 2180, silicon-on-insulator vertical coupler gratings 2300 and directly modulated vertical cavity surface emitting laser 2140 or the vertical cavity surface emitting laser with monolithically integrated electro-optic modulator 2140-A.

Figure 21C:
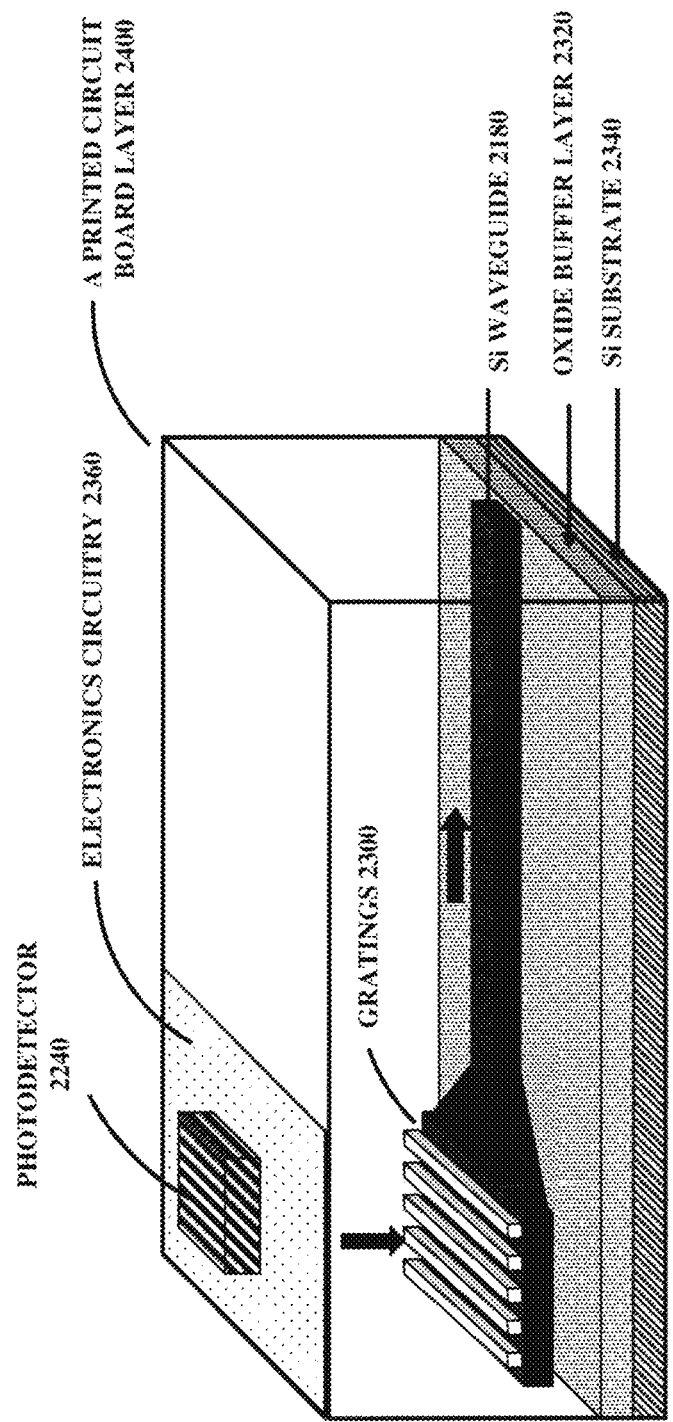

FIG. 21C illustrates details of the silicon-on-insulator waveguide 2180, silicon-on-insulator vertical coupler gratings 2300 and photodiode 2240. The shape of the silicon-on-insulator waveguide 2180 (fabricated/constructed on an oxide buffer layer 2320 on the silicon substrate 2340) can be adiabatically tapered at proximity of the silicon-on-insulator vertical coupler gratings 2300. The silicon-on-insulator vertical coupler gratings 2300 can be shaped linear or curved.

Furthermore, the silicon-on-insulator two-dimensional photonic crystal wavelength division multiplexer 2160, silicon-on-insulator waveguide 2180, reconfigurable optical switch 2200 on silicon-on-insulator and silicon-on-insulator two-dimensional photonic crystal wavelength division demultiplexer 2220 can be embedded within an etched area of polymer layers of the printed circuit board 1980. An optical mode match between the silicon-on-insulator waveguide 2180 and a polymer waveguide (utilizing a polymer layer of the printed circuit board 1980) can be fabricated/constructed. Also, the etched area can be buried within the printed circuit board 1980. Alternatively, a polymer (e.g., polyimide) waveguide of the printed circuit board 1980 can be utilized instead of the silicon-on-insulator waveguide 2180.

Figure 21D:
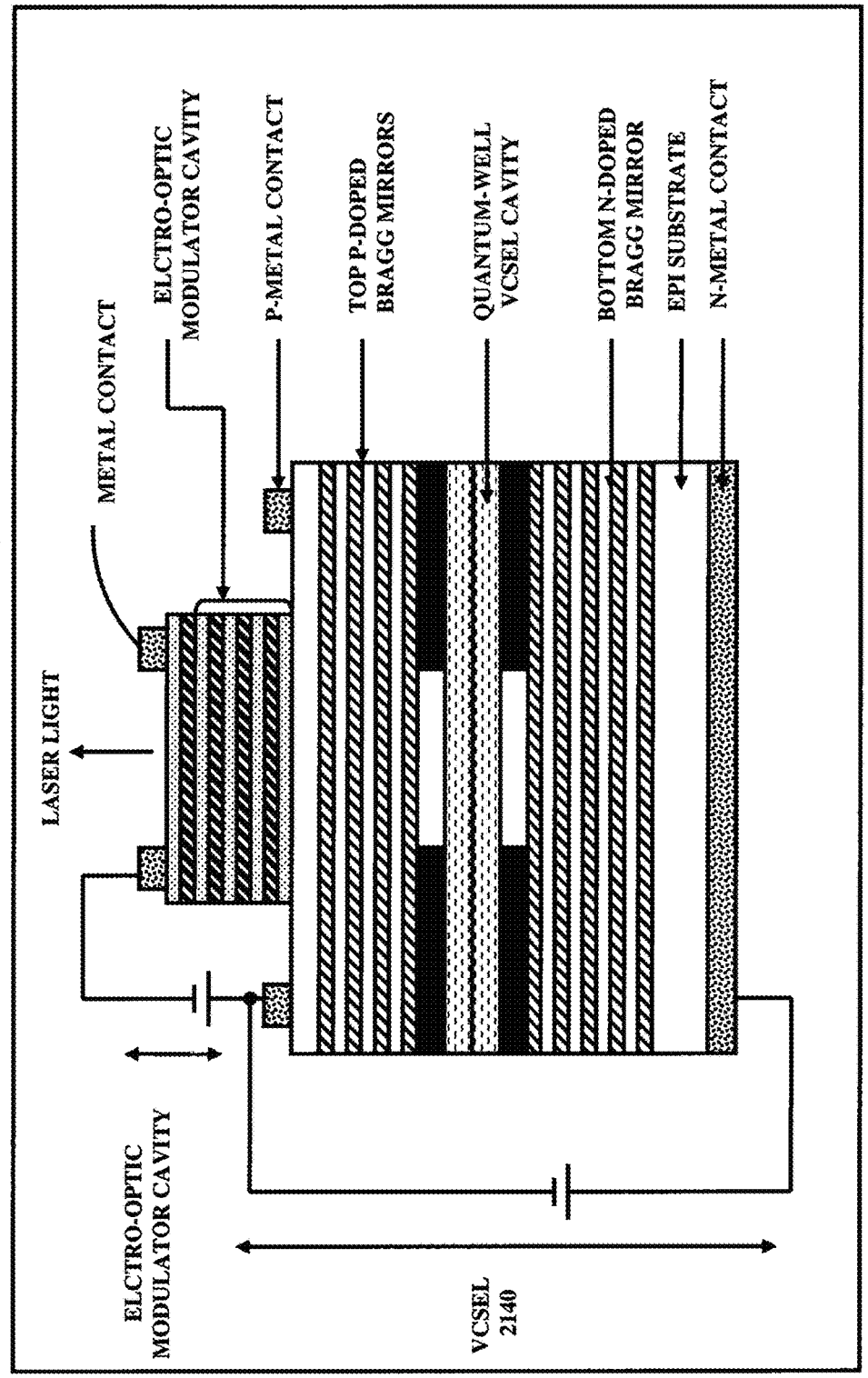

FIG. 21D illustrates a cross section of 2140-A: a vertical cavity surface emitting laser, which can be monolithically integrated with an electro-optic modulator. Similarly, a micro-electromechanical systems tunable vertical cavity surface emitting laser (preferably a quantum dot vertical cavity surface emitting laser) can also be monolithically integrated with an electro-optic modulator.

In the above disclosed specifications "/" has been used to indicate an "or".

Any example in the above disclosed specifications is by way of an example only and not by way of any limitation.

The above disclosed specifications are the preferred best mode embodiments of the present invention. However, they are not intended to be limiting only to the preferred best mode embodiments of the present invention. Numerous variations and/or modifications are possible within the scope of the present invention. Accordingly, the disclosed preferred best mode embodiments are to be construed as illustrative only. Those who are skilled in the art can make various variations and/or modifications without departing from the scope and spirit of this invention. The inventors of the present invention are not required to describe each and every conceivable and possible future embodiment in the preferred best mode embodiments of the present invention.

See SRI Int'l v. Matsushita Elec. Corp. of America, 775F.2d 1107, 1121, 227 U.S.P.Q. (BNA) 577, 585 (Fed. Cir. 1985) (enbanc). The scope and spirit of this invention shall be defined by the claims and the equivalents of the claims only. The exclusive use of all variations and/or modifications within the scope of the claims is reserved. Unless a claim term is specifically defined in the preferred best mode embodiments, then a claim term has ordinary meaning, as understood by a person with an ordinary skill in the art (e.g., a BS with 3 years of experience in the art), at the time of the present invention. As noted long ago: "Specifications teach. Claims claim". See Rexnord Corp. v. Laitram Corp., 274 F.3d 1336, 1344 (Fed. Cir. 2001). The rights of claims (and rights of the equivalents of the claims under the Doctrine of Equivalents-meeting the "Triple Identity Test" (a) performing substantially the same function, (b) in substantially the same way and (c) yielding substantially the same result. See Crown Packaging Tech., Inc. v. Rexam Beverage Can Co., 559 F.3d 1308, 1312 (Fed. Cir. 2009)). Claims of the present invention are not narrowed or limited by the selective import of the specifications (of the preferred embodiments of the present invention) into the claims. The term "means" was not used nor intended nor implied in the disclosed preferred best mode embodiments of the present invention. Thus, the inventor has not limited the scope of the claims as mean plus function. Furthermore, the scope and spirit of the present invention shall be defined by the claims and the equivalents of the claims only. Additionally, "apparatus claims are not necessarily indefinite for using functional language . . . [f]unctional language may also be employed to limit the claims without using the means-plus-function format." See Microprocessor Enhancement Corp. v. Texas Instruments Inc.

We claim:

1. A computer implemented method comprising:
 (a) accessing, by a mobile internet device or a mobile wearable internet device of a first user, via a wired network or a wireless network, a web portal enabled by a learning or relearning classical computer or a learning or relearning quantum computer,
 wherein the web portal comprises: at least a first user profile associated with the first user and a second user profile associated with a second user,
 wherein the learning or relearning classical computer is one or more cloud computers, premise computers, or mobile computers,
 wherein the learning or relearning classical computer comprises: one or more first microprocessors or one or more first neural network based microprocessors, executing computer readable instructions and one or more machine learning algorithms, stored on a non-transitory computer readable medium to implement the web portal,
 wherein the learning or relearning quantum computer comprises: one or more quantum bits (qubits) executing quantum computer enhanced algorithms or machine learning algorithms to implement the web portal,
 wherein the mobile internet device or the mobile wearable internet device of the first user comprises: a wired connector or a wireless transceiver,
 wherein the mobile internet device or the mobile wearable internet device of the first user further comprises: a second microprocessor or a second neural network based microprocessor,
 wherein the mobile internet device or the mobile wearable internet device of the first user is physically or wirelessly communicatively coupled to a social wallet electronic module of the first user, wherein the social wallet electronic module of the first user electrically couples with the second microprocessor, the second neural network based microprocessor of the mobile internet device or the mobile wearable internet device of the first user, wherein the social wallet electronic module of the first user comprises: a third microprocessor or a microcontroller, wherein the social wallet electronic module of the first user further comprises: a near-field communication (NFC) component and a biometric sensor, wherein said accessing the web portal comprises:

obtaining a first biometric scan of the first user from the biometric sensor of the social wallet electronic module of the first user, storing the first biometric scan of the first user, obtaining a second biometric scan of the first user from the biometric sensor of the social wallet electronic module of the first user, wherein the second biometric scan of the first user is a current biometric scan of the first user, comparing the first biometric scan of the first user with the second biometric scan of the first user to authenticate the first user or the social wallet electronic module of the first user;

(b) in response to at least (a), listing or linking, by the first user, a product or a service for purchase on the first user profile in the web portal;

(c) in response to at least (a) and (b), automatically determining, by the web portal, that the first user is interested in purchasing the product or the service;

(d) in response to at least (a), (b) and (c), automatically determining, by the web portal, a near real time location of the first user, wherein the near real time location of the first user is detected by a location measurement module of the mobile internet device or the mobile wearable internet device of the first user, wherein the location measurement module is selected from a group consisting of: a radio frequency identification (RFID) module, a Bluetooth module, a WiFi module and a global positioning system (GPS) module;

(e) in response to at least (a), (b), (c) and (d), automatically querying, by the web portal, queried sellers offering to sell the product or the service;

(f) in response to at least (a), (b), (c), (d) and (e), automatically selecting, by the web portal, one of the queried sellers, as a selected seller of the product or the service to purchase the product or the service from, based on a distance from the near real time location of the first user;

(g) in response to at least (a), (b), (c), (d), (e) and (f), automatically connecting, by the web portal, the first user with the selected seller;

(h) in response to at least (a), (b), (c), (d), (e), (f) and (g), automatically forwarding, by the web portal, to the mobile internet device or the mobile wearable internet device of the first user, in near real time, one or more sale offers to purchase the product or the service, from the selected seller;

(i) in response to at least (a), (b), (c), (d), (e), (f), (g) and (h), automatically accepting, by the web portal, like votes and dislike votes for the queried seller from the first user, the second user and a plurality of third users;

(j) in response to at least (a), (b), (c), (d), (e), (f), (g), (h) and (i), automatically determining a number of the like votes and a number of the dislike votes;

(k) in response to at least (a), (b), (c), (d), (e), (f), (g), (h), (i) and (j), automatically determining a seller score for the queried seller based on the number of the like votes and the number of the dislike votes by an algebraic equation, a statistical method, or an algorithm based on quorum sensing;

(l) in response to at least (a), (b), (c), (d), (e), (f), (g), (h), (i), (j) and (k), automatically displaying the seller score for the queried seller;

(m) in response to at least (a), (b), (c), (d), (e), (f), (g), (h), (i), (j), (k) and (l) automatically sending, by the web portal, to the mobile internet device or the mobile wearable internet device of the first user, a coupon for purchasing an additional product or service from the queried sellers; and (n) in response to at least (a), (b), (c), (d), (e), (f), (g), (h), (i), (j), (k), (l) and (m), automatically accepting, by the web portal, payment by the first user for the product or the service, using the web portal, the first user profile, or the near-field communication (NFC) component of the social wallet electronic module of the first user, based on one or more forwarded sale offers, wherein the said method steps in (a), (b), (c), (d), (e), (f), (g), (h), (i), (j), (k), (l), (m) and (n) are, at least an ordered combination or in an ordered sequence.

2. The method according to claim 1, wherein the web portal is coupled with one or more automated agents or bots.

3. The method according to claim 1, wherein the product, the service, or a service contract is coupled with a blockchain.

4. The method according to claim 1, wherein the web portal is receiving a first input data from one or more first sensors or a second input data from the first user, the second user and the plurality of third users.

5. The method according to claim 1, wherein the web portal is receiving a third input data from a near-field communication (NFC) tag, a quick response (QR) code, or an object, wherein the object comprises: a second sensor and a wireless transmitter.

6. The method according to claim 1, further comprising: the first user paying for the product or the service by transferring a currency or a check from the first user to the selected seller, to the second user, or to the plurality of third users.

7. A computer implemented method comprising:

(a) accessing, by a mobile internet device or a mobile wearable internet device of a first user, via a wired network or a wireless network, a web portal enabled by a learning or relearning classical computer or a learning or relearning quantum computer, wherein the web portal is receiving an input data from one or more sensors or the web portal is coupled with one or more automated agents or bots, wherein the web portal comprises: at least a first user profile associated with the first user and a second user profile associated with a second user, wherein the learning or relearning classical computer is one or more cloud computers, premise computers, or mobile computers, wherein the learning or relearning classical computer comprises: one or more first microprocessors or one or more first neural network based microprocessors, executing computer readable instructions and one or more machine learning algorithms, stored on a non-transitory computer readable medium to implement the web portal, wherein the learning or relearning quantum computer comprises: one or more quantum bits (qubits) executing quantum computer enhanced algorithms or machine learning algorithms to implement the web portal, wherein the mobile internet device or the mobile wearable internet device of the first user comprises: a wired connector or a wireless transceiver, wherein the mobile internet device or the mobile wearable internet device of the first user further comprises: a second microprocessor or a second neural network based microprocessor, wherein the mobile internet device or the mobile wearable internet device of the first user is physically or wirelessly communicatively coupled to a social wallet electronic module of the first user, wherein the social wallet electronic module of the first user electrically couples with the second microprocessor or the second neural network based microprocessor of the mobile internet device or the mobile wearable internet device of the first user, wherein the social wallet electronic module of the first user comprises: a third microprocessor or a microcontroller, wherein the social wallet electronic module of the first user further comprises: a near-field communication (NFC) component and a biometric sensor, wherein said accessing the web portal comprises:

obtaining a first biometric scan of the first user from the biometric sensor of the social wallet electronic module of the first user, storing the first biometric scan of the first user, obtaining a second biometric scan of the first user from the biometric sensor of the social wallet electronic module of the first user, wherein the second biometric scan of the first user is a current biometric scan of the first user, comparing the first biometric scan of the first user with the second biometric scan of the first user to authenticate the first user or the social wallet electronic module of the first user;

(b) in response to at least (a), listing or linking, by the first user, a product or a service for purchase on the first user profile in the web portal;

(c) in response to at least (a) and (b), automatically determining, by the web portal, that the first user is interested in purchasing the product or the service;

(d) in response to at least (a), (b) and (c), automatically determining, by the web portal, a near real time location of the first user, wherein the near real time location of the first user is detected by a location measurement module of the mobile internet device or the mobile wearable internet device of the first user, wherein the location measurement module is selected from a group consisting of: a radio frequency identification (RFID) module, a Bluetooth module, a WiFi module and a global positioning system (GPS) module;

(e) in response to at least (a), (b), (c) and (d), automatically querying, by the web portal, queried sellers offering to sell the product or the service;

(f) in response to at least (a), (b), (c), (d) and (e), automatically selecting, by the web portal, one of the queried sellers, as a selected seller of the product or the service to purchase the product or the service from, based on a distance from the near real time location of the first user;

(g) in response to at least (a), (b), (c), (d), (e) and (f), automatically connecting, by the web portal, the first user with the selected seller;

(h) in response to at least (a), (b), (c), (d), (e), (f) and (g), automatically forwarding, by the web portal, to the mobile internet device or the mobile wearable internet device of the first user, in near real time, one or more sale offers to purchase the product or the service, from the selected seller;

(i) in response to at least (a), (b), (c), (d), (e), (f), (g) and (h), automatically accepting, by the web portal, like votes and dislike votes for the queried seller from the first user, the second user and a plurality of third users;

(j) in response to at least (a), (b), (c), (d), (e), (f), (g), (h) and (i), automatically determining a number of the like votes and a number of the dislike votes;

(k) in response to at least (a), (b), (c), (d), (e), (f), (g), (h), (i) and (j), automatically determining a seller score for the queried seller based on the number of the like votes and the number of the dislike votes by an algebraic equation, a statistical method, or an algorithm based on quorum sensing;

(l) in response to at least (a), (b), (c), (d), (e), (f), (g), (h), (i), (j) and (k), automatically displaying the seller score for the queried seller;

(m) in response to at least (a), (b), (c), (d), (e), (f), (g), (h), (i), (j), (k) and (l) automatically sending, by the web portal, to the mobile internet device or the mobile wearable internet device of the first user, a coupon for purchasing an additional product or service from the queried sellers; and (n) in response to at least (a), (b), (c), (d), (e), (f), (g), (h), (i), (j), (k), (l) and (m), automatically accepting, by the web portal, payment by the first user for the product or the service, using the web portal, the first user profile, or the near-field communication (NFC) component of the social wallet electronic module of the first user, based on one or more forwarded sale offers, wherein the said method steps in (a), (b), (c), (d), (e), (f), (g), (h), (i), (j), (k), (l), (m) and (n) are, at least an ordered combination or in an ordered sequence.

8. The method according to claim 7, wherein the product, the service, or a service contract is coupled with a blockchain.

9. A system comprising:

a learning or relearning classical computer or learning or relearning quantum computer physically or wirelessly communicatively coupled to a mobile internet device or a mobile wearable internet device of a first user, wherein the learning or relearning classical computer comprises: one or more first microprocessors or one or more first neural network based microprocessors, executing computer readable instructions and one or more machine learning algorithms, stored on a first non-transitory computer readable medium to implement a web portal, wherein the learning or relearning quantum computer comprises: one or more quantum bits (qubits) executing quantum computer enhanced algorithms or machine learning algorithms to implement the web portal, wherein the web portal comprises: at least a first user profile associated with the first user and a second user profile associated with a second user, wherein the mobile internet device or the mobile wearable internet device of the first user comprises:
a second microprocessor or a second neural network based microprocessor,
a second non-transitory computer readable medium,
a display component selected from the group consisting of: a multi-touch display component, a display component with a built-in light sensing circuit, a display component with a built-in solar cell, a quantum dot display component and a stretchable display component,
a camera,
a wireless transceiver,
a location measurement module, wherein the location measurement module is selected from a group consisting of: a radio frequency identification (RFID) module, a Bluetooth module, a WiFi module and a global positioning system (GPS) module,
a social wallet electronic module comprising: a biometric sensor and a near-field communication (NFC) component,
wherein the first non-transitory computer readable medium further stores computer readable instructions, a first set of instructions, a second set of instructions, a third set of instructions, a fourth set of instructions, a fifth set of instructions, a sixth set of instructions, a seventh set of instructions, an eighth set of instructions, a ninth set of instructions, a tenth set of instructions, an eleventh set of instructions, a twelfth set of instructions, a thirteen set of instructions and a fourteen set of instructions,
wherein the second microprocessor or the second neural network based microprocessor communicates with the first non-transitory computer readable medium or the second non-transitory computer readable medium,
wherein the second microprocessor or the second neural network based microprocessor is configured to execute, in communication with the first non-transitory computer readable medium or the second non-transitory computer readable medium,
(a) the first set of instructions to access, by the mobile internet device or the mobile wearable internet device of the first user, via a wired network or wireless network, the web portal enabled by the learning or relearning computer,
wherein said accessing the web portal comprises:
obtaining a first biometric scan of the first user from the biometric sensor of the social wallet electronic module of the first user,
storing the first biometric scan of the first user,
obtaining a second biometric scan of the first user from the biometric sensor of the social wallet electronic module of the first user, wherein the second biometric scan of the user is a current biometric scan of the first user,
comparing the first biometric scan of the first user with the second biometric scan of the first user to authenticate the first user or the social wallet electronic module of the first user;
(b) in response to at least (a), the second set of instructions to list or link a product or a service for purchase on the first user profile in the web portal;
(c) in response to at least (a) and (b), the third set of instructions to automatically determine, by the web portal, that the first user is interested in purchasing the product or the service;
(d) in response to at least (a), (b) and (c), the fourth set of instructions to automatically determine, by the web portal, a near real time location of the first user, wherein the near real time location of the first user is detected by the location measurement module of the mobile internet device or the mobile wearable internet device of the first user;
(e) in response to at least, (a), (b), (c) and (d), the fifth set of instructions to automatically query, by the web portal, queried sellers offering to sell the product or the service;
(f) in response to at least, (a), (b), (c), (d) and (e), the sixth set of instructions to automatically select, one of the queried sellers as a selected seller of the product or the service to purchase the product or the service from, based on a distance from the near real time location of the first user;
(g) in response to at least, (a), (b), (c), (d), (e) and (f), the seventh set of instructions to automatically to connect the first user with the selected seller;
(h) in response to at least (a), (b), (c), (d), (e), (f) and (g), the eighth set of instructions to automatically forward, by the web portal, to the mobile internet device or the mobile wearable internet device of the first user in near real time, one or more sale offers to purchase the product or the service from the selected seller;
(i) in response to at least (a), (b), (c), (d), (e), (f), (g) and (h), the ninth set of instructions to automatically accept, by the web portal, like votes and dislike votes for the queried sellers from the first user, the second user and a plurality of third users;
(j) in response to at least (a), (b), (c), (d), (e), (f), (g), (h) and (i) the tenth set of instructions to automatically to determine a number of the like votes and a number of the dislike votes;
(k) in response to at least (a), (b), (c), (d), (e), (f), (g), (h), (i) and (j) the eleventh set of instructions to automatically to determine a seller score for the queried sellers based on the number of the like votes and the number of the dislike votes by an algebraic equation, a statistical method, or an algorithm based on quorum sensing;
(l) in response to at least (a), (b), (c), (d), (e), (f), (g), (h), (i), (j) and (k) the twelfth set of instructions to automatically to display, the seller score of the queried sellers;
(m) in response to at least (a), (b), (c), (d), (e), (f), (g), (h), (i), (j), (k) and (l) the thirteenth set of instructions to automatically send, by the web portal, to the mobile internet device or the mobile wearable internet device of the first user, a coupon for purchasing an additional product or service from one or more the queried sellers; and
(n) in response to at least (a), (b), (c), (d), (e), (f), (g), (h), (i), (j), (k), (l) and (m) the fourteenth set of instructions to automatically accept, by the web portal, payment by the first user for the product or the service, using the web portal, the first user profile, or the near-field communication (NFC) component of the social wallet electronic module of the first user, based on one or more of the forwarded sale offers,
wherein the said first set of instructions, the second set of instructions, the third set of instructions, the fourth set of instructions, the fifth set of instructions, the sixth set of instructions, the seventh set of instructions, the eighth set of instructions, the ninth set of instructions, the tenth set of instructions, the eleventh set of instructions, the twelfth set of instructions, the thirteen set of instructions and the fourteen set of instructions are, at least an ordered combination or in an ordered sequence.

10. The system according to claim 9, wherein the mobile internet device or the mobile wearable internet device is further receiving a first input data from one or more first sensors, one or more first sensors coupled with a blockchain, a second input data from a near-field communication (NFC) tag, a quick response (QR) code, or an object, wherein the object comprises: a second sensor and a first wireless transmitter.

11. The system according to claim 9, wherein the mobile internet device or the mobile wearable internet device further comprises: an algorithm selected from the group consisting of: a fuzzy logic algorithm, an intelligence rendering algorithm and a self-learning algorithm, wherein the fuzzy logic algorithm, the intelligence rendering algorithm, or the self-learning algorithm is stored in the second non-transitory computer readable medium.

12. The system according to claim 9, wherein the mobile internet device or the mobile wearable internet device further comprises: a search algorithm for a physical item, wherein the search algorithm for a physical item is stored in the second non-transitory computer readable medium.

13. The system according to claim 9, wherein the mobile internet device or the mobile wearable internet device further comprises: an algorithm selected from the group consisting of: a voice-to-text-to-voice conversion algorithm, a voice recognition algorithm, a hand-writing recognition algorithm, a facial recognition algorithm and a biometric recognition algorithm, wherein the voice-to-text-to-voice conversion algorithm or the voice recognition algorithm or the hand-writing recognition algorithm or the facial recognition algorithm or the biometric recognition algorithm is stored in the second non-transitory computer readable medium.

14. The system according to claim 9, wherein the mobile internet device or the mobile wearable internet device further comprises: a component selected from the group consisting of: a barcode reader and a radio frequency identification (RFID) reader.

15. The system according to claim 9, wherein the mobile internet device or the mobile wearable internet device further comprises: a component selected from the group consisting of: a DASH7 transceiver and a millimeter wave transceiver.

16. The system according to claim 9, wherein the mobile internet device or the mobile wearable internet device further comprises: a component selected from the group consisting of: a software-defined radio and a tunable antenna.

17. The system according to claim 9, wherein the mobile internet device or the mobile wearable internet device further comprises: a video compression module selected from the group consisting of: a video compression component and a video compression algorithm, wherein the video compression algorithm is stored in the second non-transitory computer readable medium.

18. The system according to claim 9, wherein the mobile internet device or the mobile wearable internet device further comprises: a sketch pad electronic module and a stylus, wherein the sketch pad electronic module comprises: an electronic circuitry for capacitive coupling, a transparent input matrix component and a write-erase switch.

19. The system according to claim 9, wherein the mobile internet device or the mobile wearable internet device further comprises: a personal awareness assistant electronic module, wherein the personal awareness electronic module comprises: a microphone or an audio recorder.

20. The system according to claim 19, wherein the personal awareness assistant electronic module categorizes information or data received by the personal awareness assistant electronic module into a database.

21. The system according to claim 9, wherein the mobile internet device or the mobile wearable internet device is further enabling a service by an object, wherein the object comprises: a second sensor and a first wireless transmitter.

22. The system according to claim 9, wherein the web portal is coupled with one or more automated agents or bots.

23. The system according to claim 9, wherein the mobile internet device or the mobile wearable internet device is further coupled with one or more automated agents or bots.

24. The system according to claim 9, wherein the mobile internet device or the mobile wearable internet device is further sensor aware or context aware.

* * * * *